United States Patent
Nugiel et al.

(10) Patent No.: US 6,593,356 B2
(45) Date of Patent: *Jul. 15, 2003

(54) ACYLSEMICARBAZIDES AS CYCLIN DEPENDENT KINASE INHIBITORS USEFUL AS ANTI-CANCER AND ANTI-PROLIFERATIVE AGENTS

(75) Inventors: David Nugiel, Cherry Hill, NJ (US); David Carini, Wilmington, DE (US); Susan DiMeo, Wilmington, DE (US); Anup Vidwans, Avondale, PA (US); Eddy Yue, Landenberg, PA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/906,963

(22) Filed: Jul. 16, 2001

(65) Prior Publication Data

US 2003/0073686 A1 Apr. 17, 2003

Related U.S. Application Data

(63) Continuation-in-part of application No. 09/692,023, filed on Oct. 19, 2000, now Pat. No. 6,291,504.
(60) Provisional application No. 60/160,713, filed on Oct. 20, 1999.

(51) Int. Cl.$^7$ ...................... A61K 31/416; A61P 35/00; C07D 231/54
(52) U.S. Cl. ..................... 514/403; 548/359.1
(58) Field of Search ........... 548/359.1; 514/403

(56) References Cited

U.S. PATENT DOCUMENTS 6,291,504 B1 * 9/2001 Nugiel et al. ............... 514/403
6,407,103 B2 * 6/2002 Nugiel et al. ............ 514/232.8
6,413,957 B1 * 7/2002 Nugiel et al. ............ 514/232.8

FOREIGN PATENT DOCUMENTS

WO     WO 9954308     10/1999

* cited by examiner

*Primary Examiner*—Robert W. Ramsuer
(74) *Attorney, Agent, or Firm*—Elliott Korsen; Rena Patel; Jing Belfield

(57) ABSTRACT

The present invention relates to the synthesis of a new class of indeno[1,2-c]pyrazol-4-ones of formula (I):

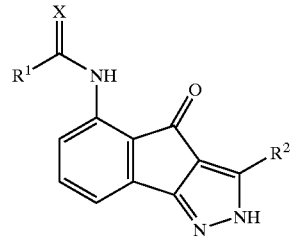

(I)

that are potent inhibitors of the class of enzymes known as cyclin dependent kinases, which relate to the catalytic subunits cdk1–7 and their regulatory subunits know as cyclins A–G.

This invention also provides a novel method of treating cancer or other proliferative diseases by administering a therapeutically effective amount of one of these compounds or a pharmaceutically acceptable salt form thereof. Alternatively, one can treat cancer or other proliferative diseases by administering a therapeutically effective combination of one of the compounds of the present invention and one or more other known anti-cancer or anti-proliferative agents.

4 Claims, No Drawings

ACYLSEMICARBAZIDES AS CYCLIN DEPENDENT KINASE INHIBITORS USEFUL AS ANTI-CANCER AND ANTI-PROLIFERATIVE AGENTS

CROSS REFERENCE TO RELATED APPLICATIONS

This application is a continuation-in-part application of U.S. Ser. No. 09/692,023, Filed Oct. 19, 2000, entitled "ACYLSEMICARBAZIDES AND THEIR USES", now U.S. Pat. No. 6,291,504, which is a non-provisional filing of provisional application 60/160,713, filed Oct. 20, 1999, entitled "ACYLSEMICARBAZIDES AS CYCLIN DEPENDENT KINASE INHIBITORS USEFUL AS ANTI-CANCER AND ANTI-PROLIFERATIVE AGENTS" which applications are herein incorporated by reference in their entirety as though set forth in full.

FIELD OF THE INVENTION

This invention relates generally to novel 5-substituted-indeno[1,2-c]pyrazol-4-ones which are useful as cyclin dependent kinase (cdk) inhibitors, pharmaceutical compositions comprising the same, methods for using the same for treating proliferative diseases, and intermediates and processes for making the same.

BACKGROUND OF THE INVENTION

One of the most important and fundamental processes in biology is the division of cells mediated by the cell cycle. This process ensures the controlled production of subsequent generations of cells with defined biological function. It is a highly regulated phenomenon and responds to a diverse set of cellular signals both within the cell and from external sources. A complex network of tumor promoting and suppressing gene products are key components of this cellular signaling process. Over expression of the tumor promoting components or the subsequent loss of the tumor suppressing products will lead to unregulated cellular proliferation and the generation of tumors (Pardee, Science 246:603–608, 1989).

Cyclin dependent kinases (cdks) play a key role in regulating the cell cycle machinery. These complexes consist of two components: a catalytic subunit (the kinase) and a regulatory subunit (the cyclin). To date, six kinase subunits (cdk 1–7) have been identified along with several regulatory subunits (cyclins A–H). Each kinase associates with a specific regulatory partner and together make up the active catalytic moiety. Each transition of the cell cycle is regulated by a particular cdk complex: G1/S by cdk2/cyclin E, cdk4/cyclin D1 and cdk6/cyclinD/2; S/G2 by cdk2/cyclin A and cdk1/cyclin A; G2/M by cdk1/B. The coordinated activity of these kinases guides the individual cells through the replication process and ensures the vitality of each subsequent generation (Sherr, Cell 73:1059–1065, 1993; Draetta, Trends Biochem. Sci. 15:378–382, 1990)

An increasing body of evidence has shown a link between tumor development and cdk related malfunctions. Over expression of the cyclin regulatory proteins and subsequent kinase hyperactivity have been linked to several types of cancers (Jiang, Proc. Natl. Acad. Sci. USA 90:9026–9030, 1993; Wang, Nature 343:555–557, 1990). More recently, endogenous, highly specific protein inhibitors of cdks were found to have a major affect on cellular proliferation (Kamb et al, Science 264:436–440, 1994; Beach, Nature 336:701–704, 1993). These inhibitors include p16$^{INK4}$ (an inhibitor of cdk4/D1), p21$^{CIP1}$ (a general cdk inhibitor), and p27$^{KIP1}$ (a specific cdk2/E inhibitor). A recent crystal structure of p27 bound to cdk2/A revealed how these proteins effectively inhibit the kinase activity through multiple interactions with the cdk complex (Pavletich, Nature 382:325–331, 1996). These proteins help to regulate the cell cycle through specific interactions with their corresponding cdk complexes. Cells deficient in these inhibitors are prone to unregulated growth and tumor formation.

This body of evidence has led to an intense search for small molecule inhibitors of the cdk family as an approach to cancer chemotherapy.

A series of indeno[1,2-c]pyrazoles having anticancer activity are described in JP 60130521 and JP 62099361 with the following generic structure:

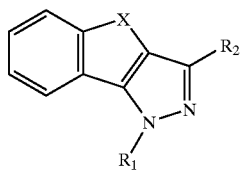

A series of indeno[1,2-c]pyrazoles having herbicidal activity are described in GB 2223946 with the following generic structure:

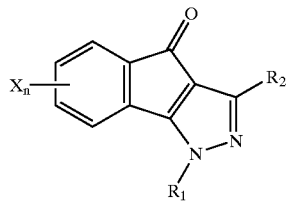

A series of 1-(6'-substituted-4'-methylquinol-2'-yl)-3-methylindeno[1,2-c]pyrazoles having CNS activity are described by Quraishi, Farmaco 44:753–8, 1989 with the following generic structure:

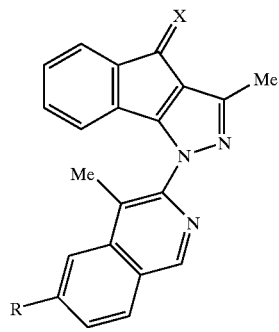

There is a continuing unmet need for cdk inhibitors with which to treat proliferative diseases.

SUMMARY OF THE INVENTION

The present invention describes a novel class of indeno[1,2-c]pyrazol-4-ones or pharmaceutically acceptable salt forms thereof that are potent inhibitors of the class of enzymes known as cyclin dependent kinases, which relate to the catalytic subunits cdk 1–7 and their regulatory subunits know as cyclins A–H.

The present invention is also directed to a novel method of treating cancer or other proliferative diseases by administering a therapeutically effective amount of one of these compounds or a pharmaceutically acceptable salt form thereof.

A novel method of treating cancer or other proliferative diseases, which comprises administering a therapeutically effective combination of one of the compounds of the present invention and one or more other known anti-cancer or anti-proliferative agents is also described herein.

The present invention also describes compounds of formula (I):

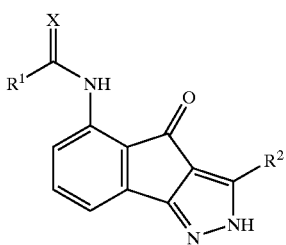

(I)

wherein $R_1$, $R_2$ and X are defined below or pharmaceutically acceptable salts thereof as cyclin dependent kinase inhibitors.

DETAILED DESCRIPTION OF PREFERRED EMBODIMENTS

The invention pertains to novel cyclin dependent kinase inhibitors (cdks) and specifically, but not exclusively, as inhibitors of cdk/cyclin complexes. The inhibitors of this invention are indeno[1,2-c]pyrazol-4-one analogs. Certain analogs were selective for their activity against cdks and their cyclin bound complexes and were less active against other known serine/threonine kinases such as Protein Kinase A (PKA) and Protein Kinase C (PKC). In addition, these inhibitors were less active against tyrosine kinases such as c-Abl.

As described herein, the inhibitors of this invention are capable of inhibiting the cell-cycle machinery and consequently would be useful in modulating cell-cycle progression, which would ultimately control cell growth and differentiation. Such compounds would be useful for treating subjects having disorders associated with excessive cell proliferation, such as the treatment of cancer, psoriasis, immunological disorders involving unwanted leukocyte proliferation, in the treatment of restinosis and other smooth muscle cell disorders, and the like.

The present invention, in a first embodiment, describes a novel compound of formula (I):

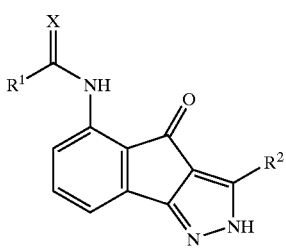

(I)

or a stereoisomer or pharmaceutically acceptable salt form thereof, wherein:

X is selected from the group: O, S, and NR;

R is selected from the group: H, $C_{1-4}$ alkyl, and $NR^5R^{5a}$;

$R^1$ is selected from the group: H, $C_{1-10}$ alkyl substituted with 0–3 $R^c$, $C_{2-10}$ alkenyl substituted with 0–3 $R^c$, $C_{2-10}$ alkynyl substituted with 0–3 $R^c$, $C_{1-10}$ alkoxy, —$NHR^4$, $C_{3-10}$ carbocycle substituted with 0–5 $R^a$, and 3–10 membered heterocycle containing from 1–4 heteroatoms selected from O, N, and S and substituted with 0–5 $R^b$;

$R^2$ is selected from the group: H, $C_{1-10}$ alkyl substituted with 0–3 $R^c$, $C_{2-10}$ alkenyl substituted with 0–3 $R^c$, $C_{2-10}$ alkynyl substituted with 0–3 $R^c$, —$(CF_2)_mCF_3$, $C_{3-10}$ carbocycle substituted with 0–5 $R^a$, and 3–10 membered heterocycle containing from 1–4 heteroatoms selected from O, N, and S and substituted with 0–5 $R^b$;

$R^3$ is selected from the group: H, halo, —CN, $NO_2$, $C_{1-4}$ haloalkyl, $NR^5R^{5a}$, $NR^5NR^5R^{5a}$, $NR^5C(O)OR^5$, $NR^5C(O)R^5$, =O, $OR^5$, $COR^5$, $CO_2R^5$, $CONR^5R^{5a}$, $NHC(O)NR^5R^{5a}$, $NHC(S)NR^5R^{5a}$, $SO_2NR^5R^{5a}$, $SO_2R^{5b}$, $C_{1-4}$ alkyl, phenyl, benzyl, $C_{1-4}$ alkyl substituted with 1–3 $R^c$, $C_{5-10}$ alkyl substituted with $C_{2-10}$ alkenyl optionally substituted with 0–3 $R^6$, $C_{2-10}$ alkynyl substituted with 0–3 $R^6$, —$(CF_2)_mCF_3$, $C_{3-10}$ carbocycle substituted with 0–5 $R^6$, and 5–10 membered heterocycle containing from 1–4 heteroatoms selected from O, N, and S, substituted with 0–3 $R^6$; and provided that if $R^3$ is phenyl, it is substituted with 1–5 $R^a$;

$R^4$ is independently at each occurrence selected from the group: H, —CN, $C_{1-4}$ alkyl, $C_{1-4}$ haloalkyl, $NR^3R^{3a}$, $NR^3C(O)OR^3$, $NR^3C(O)R^3$, $OR^3$, $COR^3$, $CO_2R^3$, $CONR^3R^{3a}$, $NHC(O)NR^3R^{3a}$, $NHC(S)NR^3R^{3a}$, $SO_2NR^3R^{3a}$, $SO_2R^{3b}$, $C_{3-10}$ carbocycle substituted with 0–5 $R^a$, and 5–10 membered heterocycle containing from 1–4 heteroatoms selected from O, N, and S, substituted with 0–3 $R^3$;

provided that at least one $R^3$ is present and that this $R^3$ is selected from the group: $C_{1-4}$ alkyl substituted with 1–3 $R^6$, $C_{5-10}$ alkyl substituted with $C_{2-10}$ alkenyl optionally substituted with 0–3 $R^6$, $C_{2-10}$ alkynyl substituted with 0–3 $R^6$, —$(CF_2)_mCF_3$, $C_{3-10}$ carbocycle substituted with 0–5 $R^6$, and 5–10 membered heterocycle containing from 1–4 heteroatoms selected from O, N, and S, substituted with 0–3 $R^6$;

$R^a$ is independently at each occurrence selected from the group: halo, —CN, $N_3$, $NO_2$, $C_{1-4}$ alkyl, $C_{1-4}$ haloalkyl, $NR^3R^{3a}$, =O, $OR^3$, $COR^3$, $CO_2R^3$, $CONR^3R^{3a}$, $NHC(O)NR^3R^{3a}$, $NHC(S)NR^3R^{3a}$, $NR^3C(O)OR^3$, $NR^3C(O)R^3$, $SO_2NR^3R^{3a}$, $SO_2R^{3b}$, and 5–10 membered heterocycle containing from 1–4 heteroatoms selected from O, N, and S;

alternatively, when two $R^2$, are present on adjacent carbon atoms they combine to form —$OCH_2O$— or —$OCH_2CH_2O$—;

$R^b$ is independently at each occurrence selected from the group: halo, —CN, $NO_2$, $C_{1-4}$ alkyl, $C_{1-4}$ haloalkyl, $NR^3R^{3a}$, $NR^3C(O)OR^3$, $NR^3C(O)R^3$, $OR^3$, $COR^3$, $CO_2R^3$, $CONR^3R^{3a}$, $NHC(O)NR^3R^{3a}$, $NHC(S)NR^3R^{3a}$, $SO_2NR^3R^{3a}$, and $SO_2R^{3b}$;

$R^c$ is independently at each occurrence selected from the group: halo, —CN, $NO_2$, $C_{1-4}$ alkyl, $C_{1-4}$ haloalkyl, $NR^3R^{3a}$, $NR^5NR^5R^{5a}$, $NR^3C(O)OR^3$, $NR^3C(O)R^3$, =O, $OR^3$, $COR^3$, $CO_2R^3$, $CONR^3R^{3a}$, $NHC(O)NR^3R^{3a}$, $NHC(S)NR^3R^{3a}$, $SO_2NR^3R^{3a}$, $SO_2R^{3b}$, $C_{3-10}$ carbocycle substituted with 0–5 $R^a$, and 5–10 membered heterocycle containing from 1–4 heteroatoms selected from O, N, and S, substituted with 0–3 $R^3$;

$R^{3a}$ is selected from the group: H, $C_{1-4}$ alkyl, phenyl, and benzyl;

alternatively, $R^3$ and $R^{3a}$, together with the nitrogen atom to which they are attached, form a heterocycle having 4–8 atoms in the ring containing an additional 0–1 N, S, or O atom and substituted with 0–3 $R^{3c}$;

$R^{3b}$ is selected from the group: H, $C_{1-4}$ alkyl, phenyl, and benzyl;

$R^{3c}$ is independently at each occurrence selected from the group: halo, —CN, $N_3$, $NO_2$, $C_{1-4}$ alkyl, $C_{1-4}$ haloalkyl, $NR^3R^{3b}$, =O, $OR^3$, $COR^3$, $CO_2R^3$, $CONR^3R^{3b}$, NHC(O)$NR^3R^{3b}$, NHC(S)$NR^3R^{3b}$, $NR^3C(O)OR^3$, $NR^3C(O)R^3$, $SO_2NR^3R^{3b}$, $SO_2R^{3b}$, and 5–10 membered heterocycle containing from 1–4 heteroatoms selected from O, N, and S;

$R^5$ is independently selected from the group: H, $C_{1-4}$ alkyl, phenyl and benzyl;

$R^{5a}$ is independently selected from the group: H, $C_{1-4}$ alkyl, phenyl and benzyl;

$R^{5b}$ is independently selected from the group: H, $C_{1-4}$ alkyl, phenyl and benzyl;

$R^6$ is independently at each occurrence selected from the group: halo, —CN, $NO_2$, $C_{1-4}$ alkyl, $C_{1-4}$ haloalkyl, $NR^5R^5$, $NR^5NR^5R^{5a}$, $NR^5C(O)OR^5$, $NR^5C(O)R^5$, =O, $OR^5$, $COR^5$, $CO_2R^5$, $CONR^5R^{5a}$, NHC(O)$NR^5R^{5a}$, NHC(S)$NR^5R^{5a}$, $SO_2NR^5R^{5a}$, $SO_2R^{5b}$, $C_{3-10}$ carbocycle substituted with 0–5 $R^5$, and 5–10 membered heterocycle containing from 1–4 heteroatoms selected from O, N, and S, substituted with 0–3 $R^5$; and m is selected from 0, 1, 2, and 3.

In another embodiment of the present invention, the compounds of formula (I) are selected from:

3-(4-methoxyphenyl)-5-(2-benzoylhydrazinecarboxamido)indeno[1,2-c]pyrazol-4-one;

3-(4-methoxyphenyl)-5-(2-isonicotinoylhydrazinecarboxamido)indeno[1,2-c]pyrazol-4-one;

3-(4-methoxyphenyl)-5-(2-nictinoylhydrazinecarboxamido)indeno[1,2-c]pyrazol-4-one;

3-(4-methoxyphenyl)-5-(2-(3,4-dihydroxybenzoyl)hydrazinecarboxamido)indeno[1,2-c]pyrazol-4-one;

3-(4-methoxyphenyl)-5(2-(4-hydroxybenzoyl)hydrazinecarboxamido)indeno[1,2-c]pyrazol-4-one;

3-(4-methoxyphenyl)-5-(2-(3-aminobenzoyl)hydrazinecarboxamido)indeno[1,2-c]pyrazol-4-one;

3-(4-methoxyphenyl)-5-(2-(4-aminobenzoyl)hydrazinecarboxamido)indeno[1,2-c]pyrazol-4-one;

3-(4-methoxyphenyl)-5-(2-(2-aminobenzoyl)hydrazinecarboxamido)indeno[1,2-c]pyrazol-4-one;

3-(4-methoxyphenyl)-5-(2-(4-N,N-dimethylaminobenzoyl)hydrazinecarboxamido)indeno[1,2-c]pyrazol-4-one;

3-(4-methoxyphenyl)-5-(2-phenethylacetylhydrazinecarboxamido)indeno[1,2-c]pyrazol-4-one;

3-(4-methoxyphenyl)-5-(2-(2-hydroxybenzoyl)hydrazinecarboxamido)indeno[1,2-c]pyrazol-4-one; and 3-(4-methoxyphenyl)-5-(2-methoxycarbonylhydrazinecarboxamido)indeno[1,2-c]pyrazol-4-one;

1-[3-(4-methoxy-phenyl)-4-oxo-2,4-dihydro-indeno[1,2-c]pyrazol-5-yl]-3-morpholin-4-yl-urea;

[3-(4-methoxy-phenyl)-4-oxo-2,4-dihydro-indeno[1,2-c]pyrazol-5-yl]-urea;

1-(2-amino-cyclohexyl)-3-[3-(4-methoxy-phenyl)-4-oxo-2,4-dihydro-indeno[1,2-c]pyrazol-5-yl]-urea;

2-(4-aminomethyl-piperidin-1-yl)-N-[3-(4-methoxy-phenyl)-4-oxo-2,4-dihydro-indeno[1,2-c]pyrazol-5-yl]-acetamide;

1-[3-(4-methoxy-phenyl)-4-oxo-2,4-dihydro-indeno[1,2-c]pyrazol-5-yl]-3-morpholin-4-yl-urea.

or pharmaceutically acceptable salt form thereof.

Another embodiment of the present invention is a pharmaceutical composition comprising: a pharmaceutically acceptable carrier and a therapeutically effective amount of a compound of formula (I).

Another embodiment of the present invention is a method of treating cancer and proliferative diseases comprising: administering to a host in need of such treatment a therapeutically effective amount of a compound of formula (I), or a pharmaceutically effective salt form thereof.

DEFINITIONS

As used herein, the following terms and expressions have the indicated meanings. The compounds of the present invention may contain an asymmetrically substituted carbon atom, and may be isolated in optically active or racemic forms. It is well known in the art how to prepare optically active forms, such as by resolution of racemic forms or by synthesis from optically active starting materials. All chiral, diastereomeric, racemic forms and all geometric isomeric forms of a structure are intended, unless the specific stereochemistry or isomer form is specifically indicated.

The term "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. In addition, the term is intended to include both unsubstituted and substituted alkyl groups, the latter referring to alkyl moieties having one or more hydrogen substituents replaced by, but not limited to halogen, hydroxyl, carbonyl, alkoxy, ester, ether, cyano, phosphoryl, amino, imino, amido, sulfhydryl, alkythio, thioester, sulfonyl, nitro, heterocyclo, aryl or heteroaryl. It will also be understood by those skilled in the art that the substituted moieties themselves can be substituted as well when appropriate.

The terms "halo" or "halogen" as used herein refer to fluoro, chloro, bromo and iodo. The term "aryl" is intended to mean an aromatic moiety containing the specified number of carbon atoms, such as, but not limited to phenyl, indanyl or naphthyl. The terms "cycloalkyl" and "bicycloalkyl" are intended to mean any stable ring system, which may be saturated or partially unsaturated. Examples of such include, but are not limited to, cyclopropyl, cyclopentyl, cyclohexyl, norbornyl, bicyclo[2.2.2]nonane, adamantly, or tetrahydronaphthyl (tetralin).

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin),

[2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 18th ed., Mack Publishing Company, Easton, Pa., 1990, p. 1445, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Prodrugs", as the term is used herein, are intended to include any covalently bonded carriers which release an active parent drug of the present invention in vivo when such prodrug is administered to a mammalian subject. Since prodrugs are known to enhance numerous desirable qualities of pharmaceuticals (i.e., solubility, bioavailability, manufacturing, etc.) the compounds of the present invention may be delivered in prodrug form. Thus, the present invention is intended to cover prodrugs of the presently claimed compounds, methods of delivering the same, and compositions containing the same. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfydryl group, respectively. Examples of prodrugs include, but are not limited to, acetate, formate, and benzoate derivatives of alcohol and amine functional groups in the compounds of the present invention.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

As used herein, the term "anti cancer" or "anti-proliferative" agent includes, but is not limited to, altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, topotecan, irinotecan, 9-amino camptothecan, 9-nitro camptothecan, GS-211, etoposide, teniposide, vinblastine, vincristine, vinorelbine, procarbazine, asparaginase, pegaspargase, octreotide, estramustine, hydroxyurea.

SYNTHESIS

The compounds of the present invention can be synthesized using the methods described below, together with synthetic methods known in the art of synthetic organic chemistry, or variations thereon as appreciated by those skilled in the art. Preferred methods include, but are not limited to, those methods described below. Each of the references cited below are hereby incorporated herein by reference.

SCHEME 1

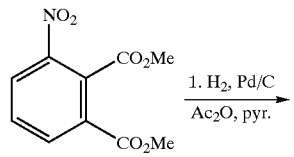

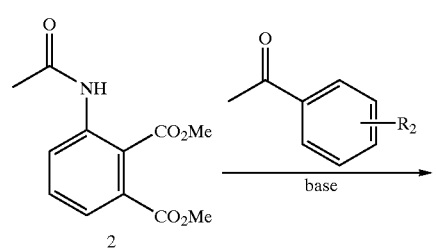

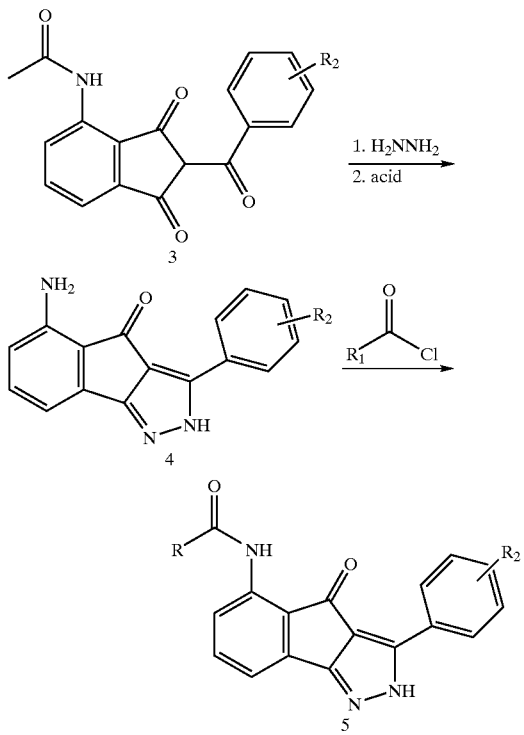

An approach to preparing indeno[1,2-c]pyrazol-4-ones is presented in Scheme 1 and can be used to prepare compounds of the present invention. The nitro group of dimethyl 3-nitrophthalate was reduced to the amine using catalytic hydrogenation. The aniline was acylated using acetic anhydride and pyridine as a base. A mixture of the resulting acetamide 2 and an acetophenone were treated with a strong base in an appropriate solvent at elevated temperature to give the desired triketone 3. Additional means of preparing triketones are known to one skilled in the art as described in Kilgore et al, Industrial and Engineering Chemistry 34:494–497, 1946, the contents of which are hereby incorporated herein by reference. The triketone was treated with hydrazine at elevated temperature in an appropriate solvent to give the indeno[1,2-c]pyrazol-4-one ring system. Additional means of preparing indeno[1,2-c]pyrazol-4-ones are known to one skilled in the art as described in Lemke et al., J. Heterocyclic Chem. 19:1335–1340, 1982; Mosher and Soeder, J. Heterocyclic Chem. 8:855–59, 1971; Hrnciar and Svanygova Collect. Czech. Chem. Commun. 59:2734–40, 1994 the contents of which are hereby incorporated herein by reference. The amide was deacylated by heating with a strong acid in an appropriate solvent to give aniline 4. This aniline was acylated under standard conditions using an acid chloride in an appropriate solvent to give the desired product 5.

SCHEME 2

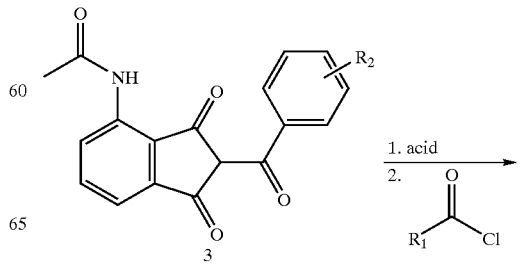

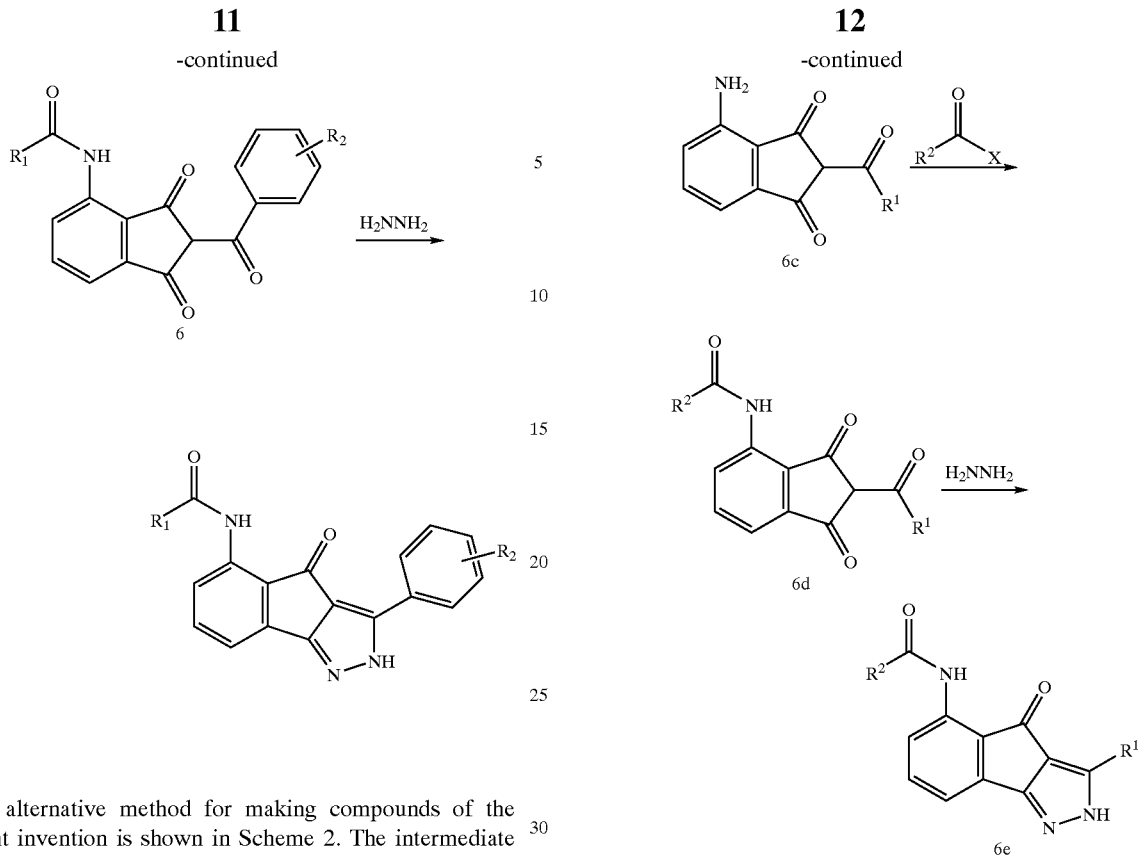

An alternative method for making compounds of the present invention is shown in Scheme 2. The intermediate triketone 3 can be deacylated with strong acid and reacylated with an appropriate acid chloride using methods known to those skilled in the art. Subsequently, triketone 6 can the be converted to the indeno[1,2-c]pyrazol-4-one ring system using the same conditions described previously in Scheme 1.

SCHEME 3

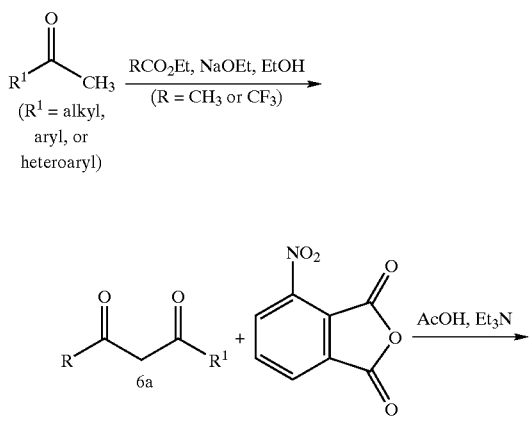

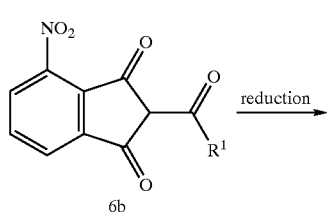

Another method for preparing the triketones 6 of Scheme 2 employs the condensation of a 1,3-diketone 6a with 3-nitrophthalic anhydride as described in Rotberg and Oshkaya, Zh. Organ. Khim. 8:84–87, 1972; Zh. Organ. Khim. 9:2548–2550, 1973, the contents of which are hereby incorporated herein by reference. The 1,3-diketones, when not commercially available can be readily prepared by one skilled in the art by the acetylation or trifluoroacetylation of the requisite methyl ketone, $R^1COCH_3$. Reduction of the nitro derivative 6b to the aniline 6c can be accomplished in a variety of ways including catalyic hydrogenation, treatment with zinc or iron under acidic conditions, or treatment with other reducing agents such as sodium dithionite or stannous chloride. Subsequently the aniline 6c can be converted to the indeno[1,2-c]pyrazol-4-ones of this invention by acylation followed by treatment with hydrazine as described previously in Scheme 2.

SCHEME 4

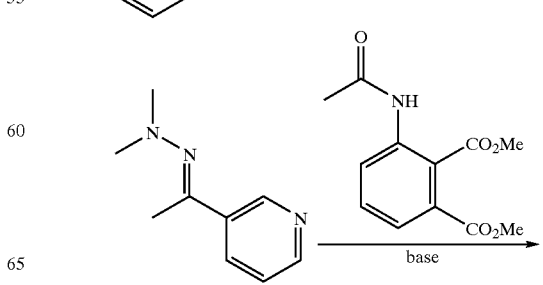

-continued

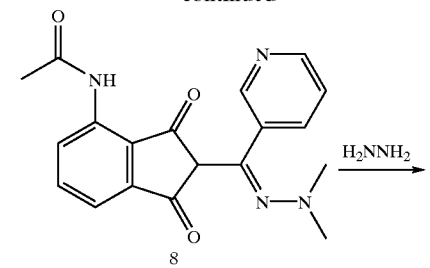
8

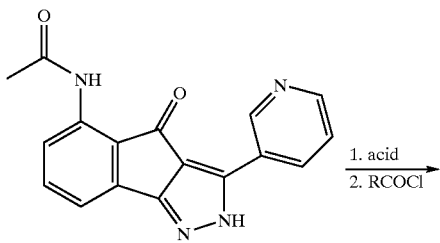
9

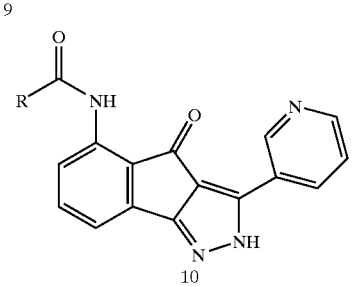
10

Another method for making the indeno[1,2-c]pyrazol-4-one ring system is shown in Scheme 4. Dimethyl hydrazine was reacted with 3-acetylpyridine with no solvent to give the hydrazone 7. This was treated in a similar fashion as described in Scheme 1 to give the desired intermediate 8. Additional means of preparing similar intermediates are known to one skilled in the art as described in Rappoport, J. Org. Chem. 49:2948–2953, 1984, the contents of which are hereby incorporated herein by reference. This intermediate was carried through the sequence in a similar fashion as described in Scheme 1.

SCHEME 5

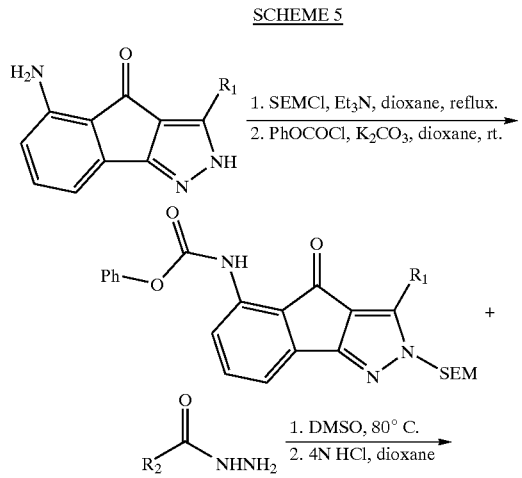

-continued

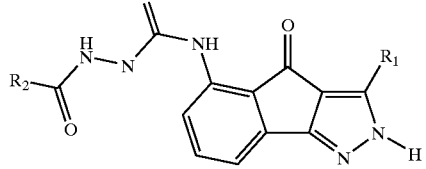

Another approach to preparing indeno[1,2-c]pyrazol-4-ones is presented in Scheme 5 and can be used to prepare compounds of the present invention. Treating the intermediate 5-aminoindeno[1,2-c]pyrazol-4-one with 2-(trimethylsilyl) ethoxymethylmethyl chloride (SEMCl) and a suitable base in an inert solvent under reflux gives the SEM protected intermediate. The aniline is converted to the carbamate with phenylchloroformate using methods known to those skilled in the art. This intermediate is reacted with carbaztes in DMSO at elevated temperatures and then the SEM group is removed by treating with acid in a polar protic solvent to give the desired acylsemicarbazide-containing indenopyrazole analogs.

Other features of the invention will become apparent during the following descriptions of exemplary embodiments which are given for illustration of the invention and are not intended to be limiting thereof.

EXAMPLES

Abbreviations used in the Examples are defined as follows: "°C." for degrees Celsius, "CIMS" for chemical ionization mass spectroscopy, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "p-TsOH" for para-toluenesulphonic acid, "DMF" for dimethylformamide, and "TFA" for trifluoroacetic acid.

Example I

Preparation of 3-(4-methoxyphenyl)-5-(acetamido) indeno[1,2-c]pyrazol-4-one

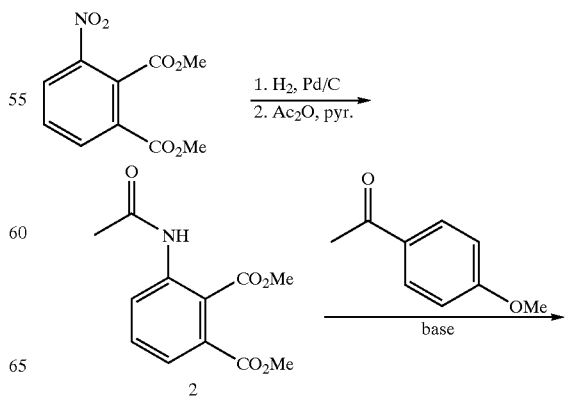
2

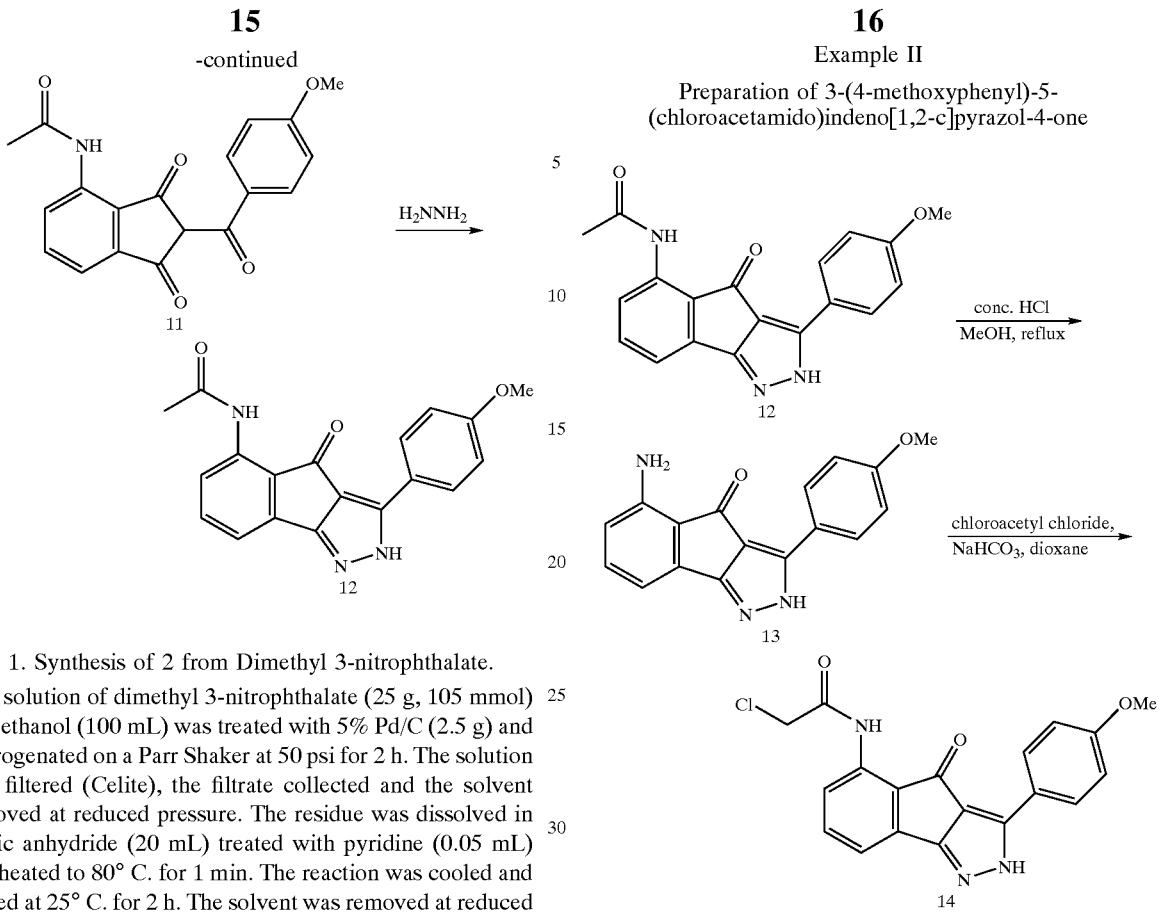

Step 1. Synthesis of 2 from Dimethyl 3-nitrophthalate.

A solution of dimethyl 3-nitrophthalate (25 g, 105 mmol) in methanol (100 mL) was treated with 5% Pd/C (2.5 g) and hydrogenated on a Parr Shaker at 50 psi for 2 h. The solution was filtered (Celite), the filtrate collected and the solvent removed at reduced pressure. The residue was dissolved in acetic anhydride (20 mL) treated with pyridine (0.05 mL) and heated to 80° C. for 1 min. The reaction was cooled and stirred at 25° C. for 2 h. The solvent was removed at reduced pressure and the residue recrystallized from ethanol to give the product as a white solid (21 g, 79%). mp 104–105° C.; CIMS m/e calc'd for $C_{12}H_{14}NO_5$: 252.0872, found 252.0888; Analysis calc'd for $C_{12}H_{13}NO_5$: C, 57.37; H, 5.22; N, 5.58; found: C, 57.67; H, 5.29; N, 5.77.

Step 2. Synthesis of Triketone 11 from 2.

A solution of 2 (1 g, 4.0 mmol) in dry DMF (2 mL) was treated with sodium hydride (0.15 g, 60% suspension in oil, 0.4 mmol) in one portion. After 1 h, 4-methoxyacetophenone (0.6 g, 4.0 mmol) was added in one portion and the reaction heated to 90° C. A second portion of sodium hydride (0.15 g, 60% suspension in oil, 0.4 mmol) was added and the exothermic reaction turns deep red. After 20 min, the reaction was cooled to 25° C. diluted with water (20 mL), extracted with EtOAc (10 mL) and the aqueous phase separated. The aqueous phase was acidified with 2 N HCl to pH 2 and the crude product collected. Recrystalization with ethanol gave the desired product as a yellow solid (0.4 g, 30%). mp 174–175° C.; CIMS m/e calc'd for $C_{19}H_{16}NO_5$: 338.1028, found 338.1022; Analysis calc'd for $C_{19}H_{15}NO_5$: C, 67.65; H, 4.48; N, 4.15; found: C, 67.87; H, 4.29; N, 3.99.

Step 3. Synthesis of 12 from 11.

A solution of 11 (0.2 g, 0.6 mmol) in EtOH (5 mL) was treated with hydrazine hydrate (0.1 mL, 1.8 mmol) and p-TsOH (3 mg). The reaction was heated to reflux and stirred for 2 h. The reaction was cooled to 25° C. and the product collected as a yellow solid (0.1 g, 50%). mp 268° C.; CIMS m/e calc'd for $C_{19}H_{16}N_3O_3$: 334.1192, found: 334.1168; Analysis calc'd for $C_{19}H_{15}N_3O_3$: C, 68.46; H, 4.54; N, 12.61; found: C, 68.81; H, 4.39; N, 12.45.

Example II

Preparation of 3-(4-methoxyphenyl)-5-(chloroacetamido)indeno[1,2-c]pyrazol-4-one Step 1. Synthesis of 13 from 12.

A suspension of 12 (1.0 g, 3.0 mmol) in MeOH (10 mL) was treated with conc. HCl (1 mL) and heated to reflux. After 2 h, the reaction was cooled and the product was collected as a greenish solid (0.7 g, 81%). mp 273° C.; CIMS m/e calc'd for $C_{17}H_{13}N_3O_2$:292.1086, found: 292.1080; Analysis calc'd for $C_{17}H_{14}N_3O_2$: C, 69.85; H, 4.83; N, 14.37; found: C, 69.99; H, 4.59; N, 14.44.

Step 2. Synthesis of 14 from 13.

A suspension of 13 (20 mg, 0.07 mmol) in dioxane (2 mL) was treated with aqueous sat. NaHCO$_3$ (1 mL) and chloroacetyl chloride (30 mL, 0.21 mmol). The reaction was heated to 50° C. and stirred for 2 h. The reaction was cooled, poured into water (2 mL), extracted with EtOAc (10 mL), the organic layer separated, dried (MgSO$_4$) and the solvent removed at reduced pressure. The solid residue was recrystallized from EtOH to give the product as a yellow solid (9 mg, 35%). mp 274° C.; CIMS m/e calc'd for $C_{19}H_{15}N_3O_3Cl$: 368.0802, found: 368.0818.

Example III

Preparation of 3-(4-methoxyphenyl)-5-(cyclopropylamido)indeno[1,2-c]pyrazol-4-one Prepared in a similar fashion as described for example II using cyclopropylacetyl chloride as the starting material. mp 289° C.; CIMS m/e calc'd for $C_{21}H_{18}N_3O_3$: 360.1348, found: 360.1330.

Example IV

Preparation of 3-(4-methoxyphenyl)-5-(isopropylamido)indeno[1,2-c]pyrazol-4-one

Prepared in a similar fashion as described for example II using isopropylacetyl chloride as the starting material. mp 288° C.; CIMS m/e calc'd for $C_{21}H_{20}N_3O_3$: 362.1505, found: 362.1535.

Example V

Preparation of 3-(4-methoxyphenyl)-5-(ethylamido)indeno[1,2-c]pyrazol-4-one Prepared in a similar fashion as described for example II using propionyl chloride as the starting material. mp 287° C.; CIMS m/e calc'd for $C_{20}H_{18}N_3O_3$: 348.1348, found: 348.1313.

Example VI

Preparation of 3-(4-methoxyphenyl)-5-(cyclopentylamido)indeno[1,2-c]pyrazol-4-one Prepared in a similar fashion as described for example II using cyclopentylacetyl chloride as the starting material. mp 267° C.; CIMS m/e calc'd for $C_{23}H_{22}N_3O_3$: 388.1661, found: 388.1626.

Example VII

Preparation of 3-(4-methoxyphenyl)-5-(cyclobutylamido)indeno[1,2-c]pyrazol-4-one Prepared in a similar fashion as described for example II using cyclobutylacetyl chloride as the starting material. mp 297° C.; CIMS m/e calc'd for $C_{22}H_{20}N_3O_3$: 374.1505, found: 374.1530.

Example VIII

Preparation of 3-(4-methoxyphenyl)-5-(phenylacetamido)indeno[1,2-c]pyrazol-4-one Prepared in a similar fashion as described for example II using phenylacetyl chloride as the starting material. mp 280° C.; CIMS m/e calc'd for $C_{25}H_{20}N_3O_3$: 410.1505, found: 410.1533.

Example IX

Preparation of 3-(4-methoxyphenyl)-5-(butylamido)indeno[1,2-c]pyrazol-4-one Prepared in a similar fashion as described for example II using butyryl chloride as the starting material. mp 282° C.; CIMS m/e calc'd for $C_{21}H_{20}N_3O_3$: 362.1505, found: 362.1500.

Example X

Preparation of 3-(4-methoxyphenyl)-5-((4-chlorophenyl)acetamido)indeno[1,2-c]pyrazol-4-one Prepared in a similar fashion as described for example II using 4-chlorophenylacetyl chloride as the starting material. mp 238° C.; CIMS m/e calc'd for $C_{25}H_{19}N_3O_3Cl$: 444.1115, found: 444.1110.

Example XI

Preparation of 3-(4-methoxyphenyl)-5-((3-methoxyphenyl)acetamido)indeno[1,2-c]pyrazol-4-one Prepared in a similar fashion as described for example II using 3-methoxyphenylacetyl chloride as the starting material. mp >300° C.; CIMS m/e calc'd for $C_{26}H_{22}N_3O_4$: 440.1610, found: 440.1620.

Example XII

Preparation of 3-(4-methoxyphenyl)-5-((4-methoxyphenyl)acetamido)indeno[1,2-c]pyrazol-4-one Prepared in a similar fashion as described for example II using 4-methoxyphenylacetyl chloride as the starting material. mp 280° C.; CIMS m/e calc'd for $C_{26}H_{22}N_3O_4$: 440.1610, found: 440.1630.

Example XIII

Preparation of 3-(4-methoxyphenyl)-5-((3,4-dimethoxyphenyl)acetamido)indeno[1,2-c]pyrazol-4-one Prepared in a similar fashion as described for example II using 3,4-dimethoxyphenylacetyl chloride as the starting material. mp >300° C.; CIMS m/e calc'd for $C_{27}H_{24}N_3O_5$: 470.1716, found: 470.1731.

Example XIV

Preparation of 3-(4-methoxyphenyl)-5-((2,5-dimethoxyphenyl)acetamido)indeno[1,2-c]pyrazol-4-one Prepared in a similar fashion as described for example II using 2,5-dimethoxyphenylacetyl chloride as the starting material. mp 226° C.; CIMS m/e calc'd for $C_{27}H_{24}N_3O_5$: 470.1716, found: 470.1739.

Example XV

Preparation of 3-(2-methoxyphenyl)-5-(acetamido)indeno[1,2-c]pyrazol-4-one

Prepared in a similar fashion as described for example I using 2-methoxyacetophenone as the starting material. mp 276° C.; CIMS m/e calc'd for $C_{19}H_{16}N_3O_3$: 334.1192, found: 334.1169.

Example XVI

Preparation of 3-(3,4-dimethoxyphenyl)-5-(acetamido)indeno[1,2-c]pyrazol-4-one Prepared in a similar fashion as described for example I using 3,4-dimethoxyacetophenone as the starting material. mp >300° C.; CIMS m/e calc'd for $C_{20}H_{18}N_3O_4$: 364.1297, found: 364.1288.

Example XVII

Preparation of 3-(4-methoxyphenyl)-5-((3,4-ethylenedioxyphenyl)acetamido)indeno[1,2-c]pyrazol-4-one

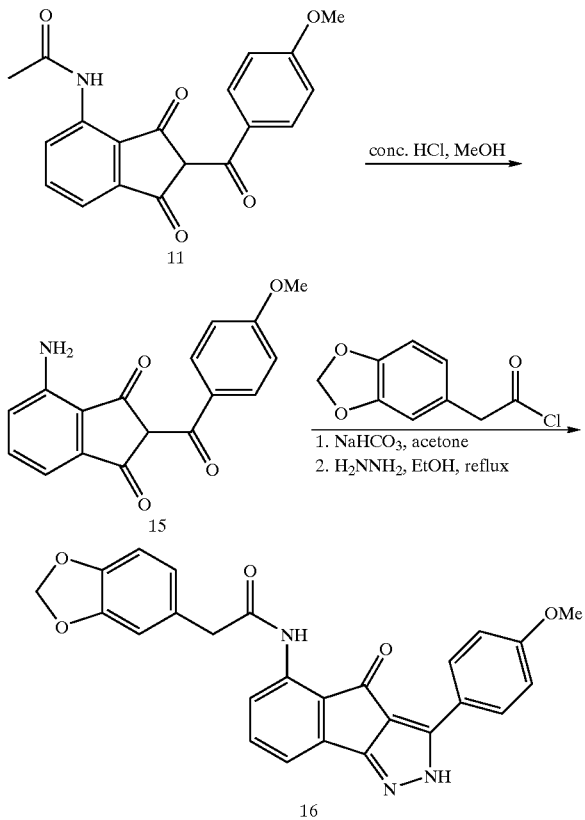

Step 1. Synthesis of 15 from 11.

A suspension of 11 (5 g, 14.8 mmol) in MeOH (50 mL) was treated with conc. HCl (3 mL) and heated to reflux. After stirring for 2 h, the reaction was cooled to 0° C. and the product collected as a yellow solid (4.2 g, 96%). mp 173° C.; CIMS m/e calc'd for $C_{17}H_{14}NO_4$: 296.0923, Found: 296.0901.

Step 2. Synthesis of 16 from 15.

A suspension of 15 (20 mg, 0.07 mmol) in acetone (2 mL) was treated with $NaHCO_3$ (10 mg) and the acid chloride of (3,4-methylenedioxyphenyl)acetic acid (prepared by heating the acid in a benzene:thionyl chloride 4:1 mixture at 50° C. for 2 h, removing the volatile components at reduced pressure, and using the crude acid chloride without further purification). The reaction was heated to 50° C. and stirred for 2 h. The reaction was cooled, poured into water (4 mL), extracted with EtOAc (10 mL), dried ($MgSO_4$), filtered and concentrated. The crude triketone was suspended in EtOH (2 mL), treated with hydrazine hydrate (0.05 mL) and p-TsOH (1 mg) and heated to reflux for 2 h. The reaction was cooled to 0° C. and the product filtered to give a yellow solid (6.5 mg, 20%). mp 297° C.; CIMS m/e calc'd for $C_{26}H_{20}N_3O_5$: 454.1403, Found: 454.1398.

Example XVIII

Preparation of 3-(4-dimethoxyphenyl)-5-((3-thiophene)acetamido)indeno[1,2-c]pyrazol-4-one Prepared in a similar fashion as described for example XVII using the acid chloride of 3-thiopheneacetic acid as the starting material. mp 293° C.; CIMS m/e calc'd for $C_{23}H_{18}N_3O_3S$: 416.1069, found: 416.1088.

Example XIX

Preparation of 3-(4-methoxyphenyl)-5-((2-methoxyphenyl)acetamido)indeno[1,2-c]pyrazol-4-one Prepared in a similar fashion as described for example XVII using the acid chloride of 2-methoxyphenylacetic acid as the starting material. mp 255° C.; CIMS m/e calc'd for $C_{26}H_{22}N_3O_4$: 440.1610, found: 440.1622.

Example XX

Preparation of 3-(4-methoxyphenyl)-5-((3,4-dichlorophenyl)acetamido)indeno[1,2-c]pyrazol-4-one Prepared in a similar fashion as described for example XVII using the acid chloride of 3,4-dichlorophenylacetic acid as the starting material. mp 299° C.; CIMS m/e calc'd for $C_{25}H_{18}N_3O_3Cl_2$: 478.0725, found: 478.0744.

Example XXI

Preparation of 3-(4-methoxyphenyl)-5-((2,4-dichlorophenyl)acetamido)indeno[1,2-c]pyrazol-4-one Prepared in a similar fashion as described for example XVII using the acid chloride of 2,4-dichlorophenylacetic acid as the starting material. mp 286° C.; CIMS m/e calc'd for $C_{25}H_{18}N_3O_3Cl_2$: 478.0725, found: 478.0734.

Example XXII

Preparation of 3-(4-methoxyphenyl)-5-((2-chlorophenyl)acetamido)indeno[1,2-c]pyrazol-4-one Prepared in a similar fashion as described for example XVII using the acid chloride of 2-chlorophenylacetic acid as the starting material. mp 300° C.; CIMS m/e calc'd for $C_{25}H_{19}N_3O_3Cl$: 444.1115, found: 444.1111.

Example XXIII

Preparation of 3-(4-methoxyphenyl)-5-(aminoacetamido)indeno[1,2-c]pyrazol-4-one

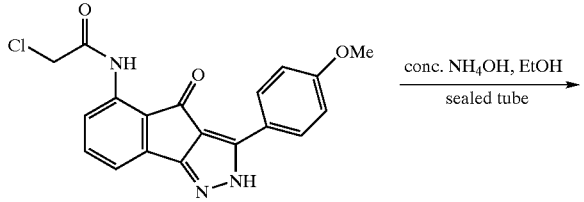

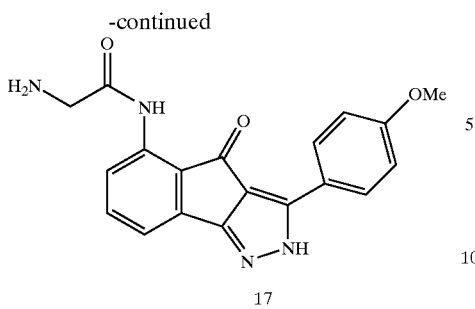

17

A suspension of 14 (15 mg, 0.04 mmol) in EtOH (1 mL) was treated with conc. NH$_4$OH (1 mL), placed in a sealed tube and heated to 80° C. for 3 h. The reaction was cooled and the solvent removed at reduced pressure. The residue was recrystallized from EtOH to give the product as a yellow solid (9 mg, 62%). mp >300° C.; CIMS m/e calc'd for C$_{20}$H$_{19}$N$_4$O$_3$: 363.1457, Found: 363.1431.

Example XXIV

Preparation of 3-(4-methoxyphenyl)-5-((2-hydroxyethyl)aminoacetamido)indeno[1,2-c]pyrazol-4-one Prepared in a similar fashion as described for example XXIII using hydroxylamine as the starting material. mp 243° C.; CIMS m/e calc'd for C$_{21}$H$_{21}$N$_4$O$_4$: 393.1563, found: 393.1539.

Example XXV

Preparation of 3-(4-methoxyphenyl)-5-(N,N-dimethylaminoacetamido)indeno[1,2-c]pyrazol-4-one Prepared in a similar fashion as described for example XXIII using dimethylamine as the starting material. mp 279° C.; CIMS m/e calc'd for C$_{21}$H$_{21}$N$_4$O$_3$: 377.1614, found: 377.1640.

Example XXVI

Preparation of 3-(4-methoxyphenyl)-5-(piperazinylacetamido)indeno[1,2-c]pyrazol-4-one Prepared in a similar fashion as described for example XXIII using piperazine as the starting material. mp 277° C.; CIMS m/e calc'd for C$_{23}$H$_{24}$N$_5$O$_3$: 418.1879, found: 418.1899.

Example XXVII

Preparation of 3-(4-methoxyphenyl)-5-(4-methylpiperazinylacetamido)indeno[1,2-c]pyrazol-4-one Prepared in a similar fashion as described for example XXIII using 4-methylpiperizine as the starting material. mp >300° C.; CIMS m/e calc'd for C$_{24}$H$_{26}$N$_5$O$_3$: 432.2036, found: 432.2030.

Example XXVIII

Preparation of 3-(4-methoxyphenyl)-5-(4-(2-hydroxyethyl)piperazinylacetamido)indeno[1,2-c]pyrazol-4-one Prepared in a similar fashion as described for example XXIII using 4-hydroxyethylpiperizine as the starting material. mp >300° C.; CIMS m/e calc'd for C$_{25}$H$_{28}$N$_5$O$_4$: 462.2141, found: 462.2128.

Example XXIX

Preparation of 3-(4-methoxyphenyl)-5-(piperidinylacetamido)indeno[1,2-c]pyrazol-4-one Prepared in a similar fashion as described for example XXIII using piperidine as the starting material. mp 291° C.; CIMS m/e calc'd for C$_{24}$H$_{25}$N$_4$O$_3$: 417.1927, found: 417.1955.

Example XXX

Preparation of 3-(4-methoxyphenyl)-5-(4-aminomethylpiperidinylacetamido)indeno[1,2-c]pyrazol-4-one Prepared in a similar fashion as described for example XXIII using 4-aminomethylpiperidine as the starting material. mp >300° C.; CIMS m/e calc'd for C$_{25}$H$_{28}$N$_5$O$_3$: 446.2192, found: 446.2166.

Example XXXI

Preparation of 3-(4-methoxyphenyl)-5-(ethylaminoacetamido)indeno[1,2-c]pyrazol-4-one Prepared in a similar fashion as described for example XXIII using ethylamine as the starting material. mp 250° C.; CIMS m/e calc'd for C$_{21}$H$_{21}$N$_4$O$_3$: 377.1614, found: 377.1644.

Example XXXII

Preparation of 3-(4-methoxyphenyl)-5-(thiomorpholinylacetamido)indeno[1,2-c]pyrazol-4-one Prepared in a similar fashion as described for example XXIII using thiomorpholine as the starting material. mp 298° C.; CIMS m/e calc'd for C$_{23}$H$_{23}$N$_4$O$_3$S: 435.1491, found: 435.1477.

Example XXXIII

Preparation of 3-(4-methoxyphenyl)-5-(morpholinylacetamido)indeno[1,2-c]pyrazol-4-one Prepared in a similar fashion as described for example XXIII using morpholine as the starting material. mp 295° C.; CIMS m/e calc'd for C$_{23}$H$_{23}$N$_4$O$_4$: 419.1719, found: 419.1744.

Example XXXIV

Preparation of 3-(4-methoxyphenyl)-5-(pyrrolidinylacetamido)indeno[1,2-c]pyrazol-4-one Prepared in a similar fashion as described for example XXIII using pyyrolidine as the starting material. mp 279° C.; CIMS m/e calc'd for C$_{23}$H$_{23}$N$_4$O$_3$: 403.1770, found: 403.1761.

Example XXXV

Preparation of 3-(4-methoxyphenyl)-5-(4-pyridinylaminomethylacetamido)indeno[1,2-c]pyrazol-4-one Prepared in a similar fashion as described for example XXIII using 4-aminomethylpyridine as the starting material.

mp >300° C.; CIMS m/e calc'd for $C_{25}H_{22}N_5O_3$: 440.1723, found: 440.1762.

Example XXXVI

Preparation of 3-(4-methoxyphenyl)-5-((4-acetamidophenyl)acetamido)indeno[1,2-c]pyrazol-4-one

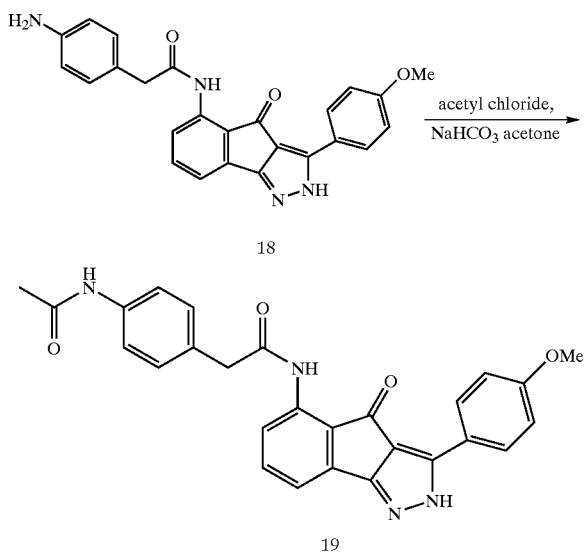

A suspension of 18 (10 mg, 0.02 mmol) in dioxane (1 mL) was treated with aqueous sat. $NaHCO_3$ (0.5 mL) and acetyl chloride (0.01 mL) and heated at 50° C. for 1 h. The reaction was cooled, poured into water (5 mL), extracted with EtOAc (10 mL), the organic layer separated, dried ($MgSO_4$) and the solvent removed at reduced pressure. The residue was recrystallized from EtOH to give the product as a yellow solid (5.6 mg, 61%). mp 268° C.; CIMS m/e calc'd for $C_{27}H_{23}N_4O_4$: 467.1719, Found: 467.1730.

Example XXXVII

Preparation of 3-(4-methoxyphenyl)-5-((4-methoxycarbonylaminophenyl)acetamido)indeno[1,2-c]pyrazol-4-one Prepared in a similar fashion as described for example XXXII using methylchloroformate as the starting material. mp 257° C.; CIMS m/e calc'd for $C_{27}H_{23}N_4O_5$: 483.1668, found: 483.1633.

Example XXXVIII

Preparation of 3-(4-methoxyphenyl)-5-((4-aminomethylcarbonylaminophenyl)acetamido)indeno[1,2-c]pyrazol-4-one Prepared in a similar fashion as described for example XXIII and XXXII using chloroacetyl chloride and conc. $NH_4OH$ as the starting materias. mp 228° C.; CIMS m/e calc'd for $C_{27}H_{24}N_5O_4$: 482.1828, found: 482.1844.

Example XXXIX

Preparation of 3-(4-methoxyphenyl)-5-((4-N,N-dimethylaminomethylcarbonylaminophenyl)acetamido)indeno[1,2-c]pyrazol-4-one Prepared in a similar fashion as described for example XXIII and XXXII using chloroacetyl chloride and dimethyl amine as the starting materias. mp >300° C.; CIMS m/e calc'd for $C_{29}H_{28}N_5O_4$: 510.2141, found: 510.2121.

Example XL

Preparation of 3-(4-methoxyphenyl)-5-((4-azidophenyl)acetamido)indeno[1,2-c]pyrazol-4-one A solution of example XXXVI (20 mg, 0.04 mmol) in DMF (2 mL) was treated with 5% palladium on carbon (5 mg) and hydrogentaed at atmospheric pressure using a hydrogen baloon. After 2 h, the solution was filtered (Celite), and the solvent removed at reduced pressure. The residue was recrystallized from EtOH to give the product as a yellow solid (15 mg, 78%). mp >300° C.; CIMS m/e calc'd for $C_{25}H_{19}N_6O_3$: 451.1519, found: 451.1544.

Example XLI

Preparation of 3-(4-methoxyphenyl)-5-((4-aminophenyl)acetamido)indeno[1,2-c]pyrazol-4-one Prepared in a similar fashion as described for example XXVII using the acid chloride of 4-azidophenylacetic acid as the starting material. mp 283° C.; CIMS m/e calc'd for $C_{25}H_{21}N_4O_3$: 425.1614, found: 425.1643.

Example XLII

Preparation of 3-(4-methoxyphenyl)-5-(phenylcarbamoyl)aminoindeno[1,2-c]pyrazol-4-one

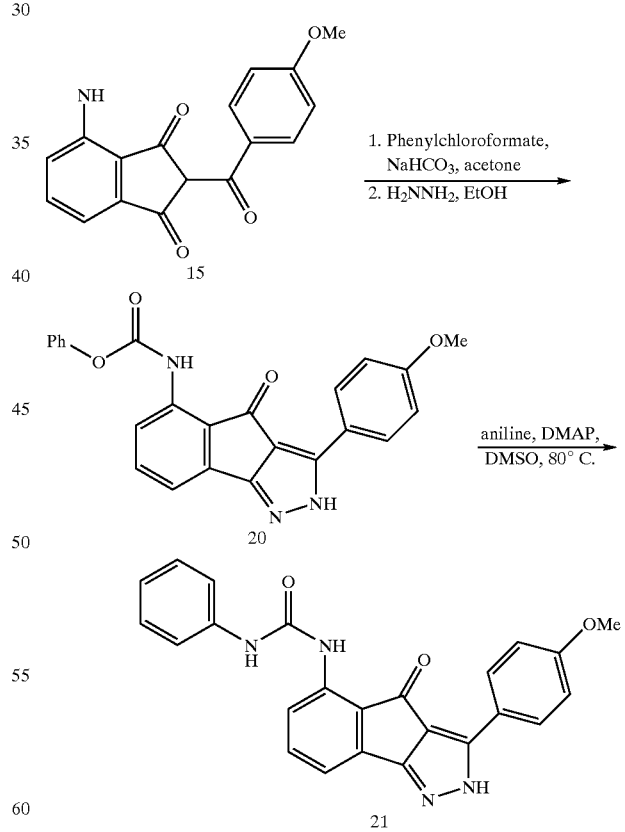

Step 1. Synthesis of 20 from 15.
A suspension of 15 (0.5 g, 1.7 mmol) in acetone (10 mL) was treated with $NaHCO_3$ (0.5 g) and phenyl chloroformate. The mixture was heated to 50° C. for 2 h. The reaction was cooled, poured into water (20 mL), extracted with EtOAc (40 mL), the organic layer separated, dried (MgSO$_4$) and the solvent removed at reduced pressure. The residue was suspended in EtOH (10 mL) and treated with hydrazine hydrate (0.16 mL, 5.1 mmol) and p-TsOH (10 mg). The mixture was heated to reflux and stirred for 3 h. The reaction was cooled to 0° C. and the product collected as a yellow solid (0.25 g, 36%). mp 195° C.; CIMS m/e calc'd for C$_{24}$H$_{18}$N$_3$O$_4$: 412.1297, Found: 412.1308.

Step 2. Synthesis of 21 from 20.

A solution of 20 (20 mg, 0.05 mmol) in DMSO (2 mL) was treated with aniline (20 mL, mmol) and dimethylaminopyridine (1 mg). The mixture was heated to 80° C. for 2 h. The reaction was cooled, poured into water (4 mL), extracted with EtOAc (15 mL), the organic layer separated, dried (MgSO$_4$) and the solvent removed at reduced pressure. The residue was recrystallized from EtOH to give the product as a yellow solid (9 mg, 44%). mp >300° C.; CIMS m/e calc'd for C$_{24}$H$_{19}$N$_4$O$_3$: 411.1457, Found: 411.1432.

Example XLIII

Preparation of 3-(4-methoxyphenyl)-5-(butylcarbamoyl)aminoindeno[1,2-c]pyrazol-4-one Prepared in a similar fashion as described for example XLII using butyl amine as the starting material. mp 252° C.; CIMS m/e calc'd for C$_{21}$H$_{21}$N$_4$O$_3$: 377.1614, found: 377.1633.

Example XLIV

Preparation of 3-(4-methoxyphenyl)-5-(4-aminobenzylcarbamoyl)aminoindeno[1,2-c]pyrazol-4-one Prepared in a similar fashion as described for example XLII using 4-aminobenzyl amine as the starting material. mp >300° C.; CIMS m/e calc'd for C$_{25}$H$_{22}$N$_5$O$_3$: 440.1723, found: 440.1700.

Example XLV

Preparation of 3-(4-methoxyphenyl)-5-(4-pyridylcarbamoyl)aminoindeno[1,2-c]pyrazol-4-one Prepared in a similar fashion as described for example XLII using 4-aminomethylpyridine as the starting material. mp >300° C.; CIMS m/e calc'd for C$_{24}$H$_{20}$N$_5$O$_3$: 426.1566, found: 426.1533.

Example XLVI

Preparation of 3-(4-hydroxyphenyl)-5-(acetamido)indeno[1,2-c]pyrazol-4-one

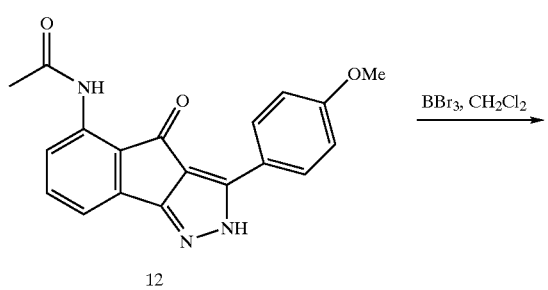

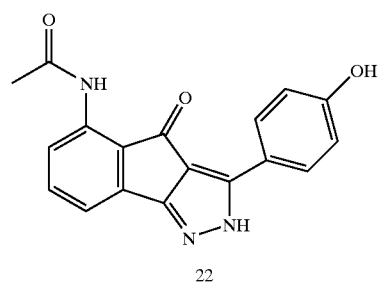

A suspension of 12 (20 mg, 0.07 mmol) in CH$_2$Cl$_2$ (2 mL) was treated with excess BBr$_3$ (1.0 mL, 1.0 M in CH$_2$Cl$_2$) and stirred for 20 h. The reaction was slowly poured into aqueous sat. NaHCO$_3$ (5 mL), extracted with EtOAc (10 mL), dried (MgSO$_4$) and concentrated. The residue was recrystallized from EtOH to give the desired product as a yellow solid (7.5 mg, 33%). mp >300° C.; CIMS m/e calc'd for C$_{18}$H$_{14}$N$_3$O$_3$: 320.1035, Found: 320.1050.

Example XLVII

Preparation of 3-(4-methoxyphenyl)-5-(formamido)indeno[1,2-c]pyrazol-4-one

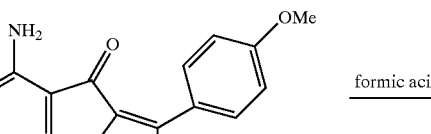

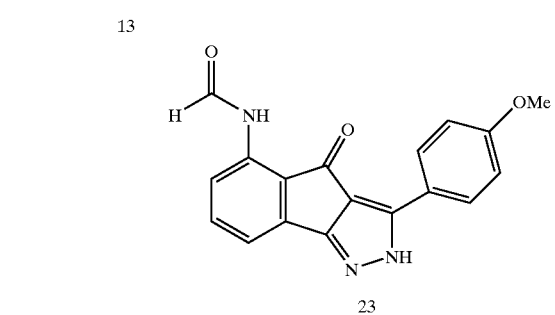

A suspension of 13 (20 mg, 0.06 mmol) in formic acid (2 mL) was heated to 100° C. for 2 h. The reaction mixture was cooled and the solvent removed at reduced pressure. The residue was recrystallized from EtOH to give the desired product as a yellow solid (12 mg, 63%). mp 280° C.; CIMS m/e calc'd for C$_{18}$H$_{14}$N$_3$O$_3$: 320.1035, Found: 320.1040.

Example XLVIII

Preparation of 3-(3-pyridyl)-5-(acetamido)indeno[1,2-c]pyrazol-4-one

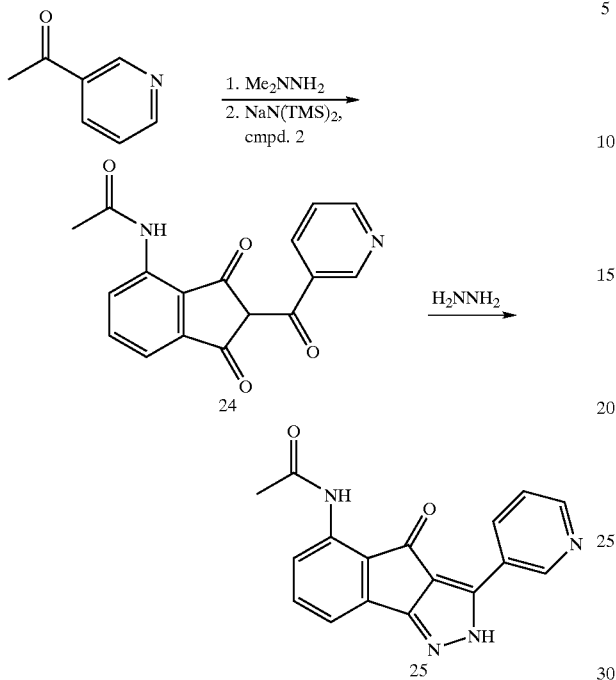

Step 1. Synthesis of 24 from 3-acetylpyridine.

A solution of 3-acetylpyridine (1.0 g, 8.3 mmol) in benzene (3 mL) was treated with 1,1-dimethylhydrazine (0.62 mL, 8.3 mmol) and p-TsOH (5 mg). The mixture was heated to 85° C. and stirred for 3 h. The reaction was cooled and the solvent removed at reduced pressure. This crude hydrazone was treated with 1.0 M NaN(TMS)$_2$ in THF (16.6 mL, 16.6 mmol) at 25° C. over 5 min. After 30 min dimethyl 3-acetamidophthalate (2.1 g, 8.3 mmol) was added in one portion and the reaction heated to reflux. Stirring was continued for 6 h. The reaction was cooled and quenched by the slow addition of TFA. The solvent was removed at reduced pressure and the residue chromatographed (silica, 2.5–5% MeOH/CH$_2$Cl$_2$) to give the product as a yellow solid (0.35 g, 14%). mp 265° C.; CIMS m/e calc'd for $C_{17}H_{13}N_2O_4$: 309.0875, Found: 309.0888.

Step 2. Synthesis of 25 from 24.

A suspension of 24 (30 mg, 0.09 mmol) in EtOH (2 mL) was treated with hydrazine hydrate (0.05 mL) and p-TsOH (1 mg) and heated to reflux. After stirring for 2 h. the reaction was cooled and the product filtered to give a yellow solid (12 mg, 44%). mp >300° C.; CIMS m/e calc'd for $C_{17}H_{13}N_4O_2$: 305.1039, Found: 305.1048.

Example XLIX

Preparation of 3-(4-pyridyl)-5-(acetamido)indeno[1,2-c]pyrazol-4-one

Prepared in a similar fashion as described for example XLVIII using 4-acetylpyridine as the starting material. mp >300° C.; CIMS m/e calc'd for $C_{17}H_{13}N_4O_2$: 305.1039, found: 305.1046.

Example L

Preparation of 3-(4-pyridyl)-5-(formamido)indeno[1,2-c]pyrazol-4-one

Prepared in a similar fashion as described for example XLVII using 4-acetylpyridine as the starting material. mp >300° C.; CIMS m/e calc'd for $C_{16}H_{11}N_4O_2$: 291.0882, found: 291.0882.

Example LI

Preparation of 3-phenyl-5-(acetamido)indeno[1,2-c]pyrazol-4-one

Prepared in a similar fashion as described for example I using acetophenone as the starting material. mp >300° C.; CIMS m/e calc'd for $C_{18}H_{13}N_3O_2$: 304.1065, found: 304.1086.

Example LII

Preparation of 3-(4-methylthiophenyl)-5-(acetamido)indeno[1,2-c]pyrazol-4-one

Prepared in a similar fashion as described for example I using 4'-methylthioacetophenone as the starting material. mp 283° C.; CIMS m/e calc'd for $C_{19}H_{15}N_3O_2S$: 350.0956, found: 350.0963.

Example LIII

Preparation of 3-(4-methylsulphonylphenyl)-5-(acetamido)indeno[1,2-c]pyrazol-4-one Prepared by oxidation of the product of example LII. mp >300° C.; CIMS m/e calc'd for $C_{19}H_{15}N_3O_4S$: 382.0860, found: 382.0862.

Example LIV

Preparation of 3-(4-N,N-dimethylaminophenyl)-5-(acetamido)indeno[1,2-c]pyrazol-4-one Prepared in a similar fashion as described for example I using 4'-N,N,-dimethylaminoacetophenone as the starting material. mp >300° C.; CIMS m/e calc'd for $C_{20}H_{18}N_4O_2$: 347.1496, found: 347.1508.

Example LV

Preparation of 3-(4-N,N-dimethylaminophenyl)-5-(morpholinylacetamido)indeno[1,2-c]pyrazol-4-one Prepared in a similar fashion as described for examples II and XXIII employing the product of example LIV and morpholine as the starting materials. mp >300° C.; CIMS m/e calc'd for $C_{24}H_{26}N_5O_3$: 432.2036, found: 432.2020.

Example LVI

Preparation of 3-(4-N,N-dimethylaminophenyl)-5-(dimethylaminoacetamido)indeno[1,2-c]pyrazol-4-one Prepared in a similar fashion as described for examples II and XXIII employing the product of example LIV and dimethylamine as the starting materials. mp >300° C.; CIMS m/e calc'd for $C_{22}H_{24}N_5O_2$: 390.1930, found: 390.1948.

Example LVII

Preparation of 3-(4-(1-piperidinyl)phenyl)-5-(acetamido)indeno[1,2-c]pyrazol-4-one Prepared in a similar fashion as described for example I using 4'-(1-piperidinyl)acetophenone as the starting material. mp 291° C.; CIMS m/e calc'd for $C_{23}H_{22}N_4O_2$: 387.1801, found: 387.1821.

Example LVIII

Preparation of 3-(4-morpholinyl)phenyl)-5-(acetamido)indeno[1,2-c]pyrazol-4-one

Prepared in a similar fashion as described for example I using 4'-morpholinylacetophenone as the starting material. mp >300° C.; CIMS m/e calc'd for $C_{22}H_{20}N_4O_3$: 388.1528, found: 388.1535.

Example LIX

Preparation of 3-(4-ethoxyphenyl)-5-(acetamido)indeno[1,2-c]pyrazol-4-one

Prepared in a similar fashion as described for example I using 4'-ethoxyacetophenone as the starting material. mp 288° C.; CIMS m/e calc'd for $C_{20}H_{17}N_3O_3$: 348.1325, found: 348.1348.

Example LX

Preparation of 3-(4-butylphenyl)-5-(acetamido)indeno[1,2-c]pyrazol-4-one

Prepared in a similar fashion as described for example I using 4'-butylacetophenone as the starting material. mp 259° C.; CIMS m/e calc'd for $C_{22}H_{21}N_3O_2$: 360.1701, found: 360.1712.

Example LXI

Preparation of 3-(4-ethylphenyl)-5-(acetamido)indeno[1,2-c]pyrazol-4-one

Prepared in a similar fashion as described for example I using 4'-ethylacetophenone as the starting material. mp 294° C.; CIMS m/e calc'd for $C_{20}H_{17}N_3O_2$: 331.1310, found: 331.1321.

Example LXII

Preparation of 3-(4-n-propylphenyl)-5-(acetamido)indeno[1,2-c]pyrazol-4-one

Prepared in a similar fashion as described for example I using 4'-n-propylacetophenone as the starting material. mp 269° C.; CIMS m/e calc'd for $C_{21}H_{19}N_3O_2$: 346.1555, found: 346.1554.

Example LXIII

Preparation of 3-(4-methoxyphenyl)-5-carbamoylaminoindeno[1,2-c]pyrazol-4-one

Prepared in a similar fashion as described for example XLII using concentrated ammonium hydroxide as the starting material. mp >300° C.; CIMS m/e calc'd for $C_{18}H_{15}N_4O_3$: 335.1144, found: 335.1113.

Example LXIV

Preparation of 3-(4-methoxyphenyl)-5-(dimethylaminocarbamoyl)aminoindeno[1,2-c]pyrazol-4-one Prepared in a similar fashion as described for example XLII using dimethylamino hydrazine as the starting material. mp >300° C.; CIMS m/e calc'd for $C_{20}H_{20}N_5O_3$: 378.1566, found: 378.1555.

Example LXV

Preparation of 3-(4-methoxyphenyl)-5-(methylcarbamoyl)aminoindeno[1,2-c]pyrazol-4-one Prepared in a similar fashion as described for example XLII using methylamine as the starting material. mp >300° C.; CIMS m/e calc'd for $C_{19}H_{17}N_4O_3$: 349.1300, found: 349.1311.

Example LXVI

Preparation of 3-(4-methoxyphenyl)-5-(morpholinocarbamoyl)aminoindeno[1,2-c]pyrazol-4-one Prepared in a similar fashion as described for example XLII using N-aminomorpholine as the starting material. mp >300° C.; CIMS m/e calc'd for $C_{22}H_{22}N_5O_4$: 420.1671, found: 420.1655.

Example LXVII

Preparation of 3-(4-methoxyphenyl)-5-(cis-2-aminocyclohexanylcarbamoyl)aminoindeno[1,2-c]pyrazol-4-one Prepared in a similar fashion as described for example XLII using cis-1,2-diaminocyclohexane as the starting material. mp >300° C.; CIMS m/e calc'd for $C_{24}H_{26}N_5O_3$: 432.2035, found: 432.2020.

Example LXVIII

Preparation of 3-(4-methoxyphenyl)-5-(4-methylpiperazinylcarbamoyl)aminoindeno[1,2-c]pyrazol-4-one Prepared in a similar fashion as described for example XLII using (4-amino)methylpiperazine as the starting material. mp >300° C.; CIMS m/e calc'd for $C_{23}H_{25}N_6O_3$: 433.1987, found: 433.1999.

Example LXIX

Preparation of 3-(4-methoxyphenyl)-5-(4-uridomethylpiperadinylacetamido)indeno[1,2-c]pyrazol-4-one Prepared in a similar fashion as described for example XXIII using example XXX as the starting material. mp >300° C.; CIMS m/e calc'd for $C_{26}H_{29}N_6O_4$: 489.2250, found: 489.2209.

Example LXX

Preparation of 3-(4-methoxyphenyl)-5-(4-(2-pyridyl)piperazinylacetamido)indeno[1,2-c]pyrazol-4-one Prepared in a similar fashion as described for example XXIII using 4-(2-pyridyl)piperazine as the starting material. mp >300° C.; CIMS m/e calc'd for $C_{28}H_{27}N_6O_3$: 495.2144, found: 495.2111.

Example LXXI

Preparation of 3-(4-methoxyphenyl)-5-(4-(aminoethyl)piperazinylacetamido)indeno[1,2-c]pyrazol-4-one Prepared in a similar fashion as described for example XXIII using 4-(aminoethyl)piperazine as the starting material. mp >300° C.; CIMS m/e calc'd for $C_{25}H_{29}N_6O_3$: 461.2300, found: 461.2333.

Example LXXII

Preparation of 3-(4-methoxyphenyl)-5-(4-amidopiperadinylacetamido)indeno[1,2-c]pyrazol-4-one Prepared in a similar fashion as described for example XXIII using isonipecotamide as the starting material. mp >300° C.; CIMS m/e calc'd for $C_{25}H_{26}N_5O_4$: 460.1984, found: 460.1998.

Example LXXIII

Preparation of 3-(4-methoxyphenyl)-5-(4-hydroxypiperadinylacetamido)indeno[1,2-c]pyrazol-4-one Prepared in a similar fashion as described for example XXIII using 4-hydroxypiperadine as the starting material. mp >300° C.; CIMS m/e calc'd for $C_{24}H_{25}N_4O_4$: 433.1875, found: 433.1844.

Example LXXIV

Preparation of 3-(4-methoxyphenyl)-5-(4-hydroxmethylypiperadinylacetamido)indeno[1,2-c]pyrazol-4-one Prepared in a similar fashion as described for example XXIII using 4-hydroxmethylypiperadine as the starting material. mp >300° C.; CIMS m/e calc'd for $C_{25}H_{27}N_4O_4$: 447.2032, found: 447.2002.

Example LXXV

Preparation of 3-(4-methoxyphenyl)-5-(4-amidopiperazinylacetamido)indeno[1,2-c]pyrazol-4-one Prepared in a similar fashion as described for example XXIII using 4-amidopiperazine as the starting material. mp >300° C.; CIMS m/e calc'd for $C_{24}H_{25}N_6O_6$: 493.1835, found: 493.1802.

Example LXXVI

Preparation of 3-(4-methoxyphenyl)-5-(4-dimethylaminopiperadinylacetamido)indeno[1,2-c]pyrazol-4-one Prepared in a similar fashion as described for example XXIII using 4-dimethylaminopiperadine as the starting material. mp >300° C.; CIMS m/e calc'd for $C_{26}H_{30}N_5O_5$: 492.2246, found: 492.2220.

Example LXXVII

Preparation of 3-(4-methoxyphenyl)-5-(4-aminopiperadinylacetamido)indeno[1,2-c]pyrazol-4-one Prepared in a similar fashion as described for example XXIII using 4-aminopiperadine as the starting material. mp >300° C.; CIMS m/e calc'd for $C_{24}H_{26}N_5O_5$: 464.1933, found: 464.1975.

Example LXXVIII

Preparation of 3-(4-(dimethylamino)phenyl)-5-((4-methyl-1-piperazinyl)acetamido)indeno[1,2-c]pyrazol-4-one Prepared in a similar fashion as described for examples II and XXIII employing the product of example LIV and 1-methylpiperazine as the starting materials. mp >300° C.; ESI-MS m/e calc'd for $C_{25}H_{29}N_6O_2$: 445.2352, found: 445.2359.

Example LXXIX

Preparation of 3-(4-(dimethylamino)phenyl)-5-((4-amino methyl-1-piperidinyl)acetamido)indeno[1,2-c]pyrazol-4-one Prepared in a similar fashion as described for examples II and XXIII employing the product of example LIV and 4-(aminomethyl)piperidine as the starting materials. ESI-MS m/e calc'd for $C_{26}H_{31}N_6O_2$: 459.2508, found: 459.2508.

Example LXXX

Preparation of 3-(4-(dimethylamino)phenyl)-5-((4-hydroxy-1-piperidinyl)acetamido)indeno[1,2-c]pyrazol-4-one Prepared in a similar fashion as described for examples II and XXIII employing the product of example LIV and 4-hydroxypiperidine as the starting materials. mp 267° C.; ESI-MS m/e calc'd for $C_{25}H_{28}N_5O_3$: 446.2192, found: 446.2206.

Example LXXXI

Preparation of 3-(4-(4-morpholinyl)phenyl)-5-(4-morpholinyl)acetamido)indeno[1,2-c]pyrazol-4-one Prepared in a similar fashion as described for examples II and XXIII employing the product of example LVIII and morpholine as the starting materials. mp 258° C.; ESI-MS m/e calc'd for $C_{26}H_{28}N_5O_4$: 474.2141, found: 474.2151.

Example LXXXII

Preparation of 3-(4-(4-morpholinyl)phenyl)-5-((4-methyl-1-piperazinyl)acetamido)indeno[1,2-c]pyrazol-4-one Prepared in a similar fashion as described for examples II and XXIII employing the product of example LVIII and 1-methylpiperazine as the starting materials. mp 258° C.; ESI-MS m/e calc'd for $C_{27}H_{31}N_6O_3$: 487.2457, found: 487.2447.

Example LXXXIII

Preparation of 3-(4-(4-morpholinyl)phenyl)-5-((4-hydroxy-1-piperidinyl)acetamido)indeno[1,2-c]pyrazol-4-one Prepared in a similar fashion as described for examples II and XXIII employing the product of example LVIII and 4-hydroxypiperidine as the starting materials. mp 245° C.; ESI-MS m/e calc'd for $C_{27}H_{30}N_5O_4$: 488.2298, found: 488.2290.

Example LXXXIV

Preparation of 3-(4-(4-morpholinyl)phenyl)-5-((4-amino methyl-1-piperidinyl)acetamido)indeno[1,2-c]pyrazol-4-one Prepared in a similar fashion as described for examples II and XXIII employing the product of example LVIII and 4-(aminomethyl)piperidine as the starting materials. mp 240° C.; ESI-MS m/e calc'd for $C_{28}H_{33}N_6O_3$: 501.2614, found: 501.2619.

Example LXXXV

Preparation of 3-(4-(dimethylamino)phenyl)-5-((((4-methyl-1-piperazinyl)amino)carbonyl)amino)indeno[1,2-c]pyrazol-4-one Prepared in a similar fashion as described for examples I, XXVII, and XLII employing the 4-(dimethylamino) acetophenone and 1-amino-4-methylpiperazine as the starting materials. mp >300° C.; ESI-MS m/e calc'd for $C_{24}H_{28}N_7O_2$: 446.2304, found: 446.2310.

Example LXXXVI

Preparation of 3-(i-propyl)-5-(acetamido)indeno[1,2-c]pyrazol-4-one

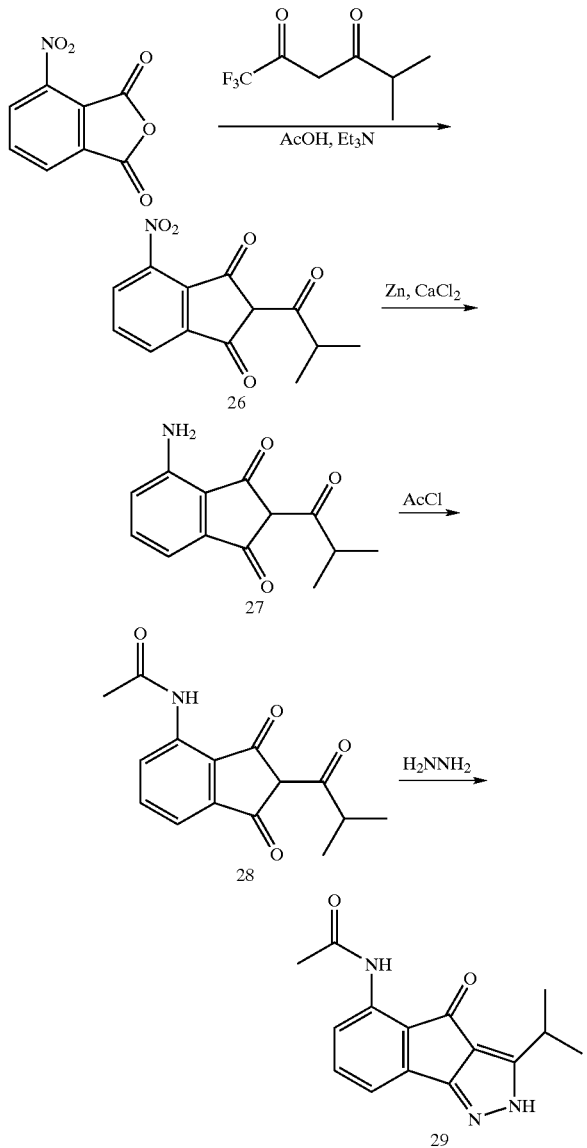

Step 1. Synthesis of 26 from 3-nitrophthalic Anhydride.

A solution of 3-nitrophthalic anhydride (9.7 g, 50 mmol) and 1,1,1-trifluoro-5-methyl-2,4-hexanedione (9.1 g, 50 mmol) in acetic anhydride (28.3 mL, 300 mmol) was treated with triethylamine (13.95 mL, 100 mmol) and stirred at 25° C. for 4 h. The solution was diluted with 1 N HCl (200 mL) and the precipate collected and washed with water (200 mL) and hexane (400 mL) to give the product as a yellow solid (11.1 g, 85%). mp 127–129° C.; CIMS (M+H) calc'd for $C_{13}H_{12}NO_5$: 262.0715, found: 262.0694.

Step 2. Synthesis of triketone 27 from 26.

A solution of 26 (11 g, 42 mmol) in EtOH (224 mL) and water (56 mL) was treated with zinc (90 g, 1.4 mol) and calcium chloride (3 g, 27 mmol) and heated to reflux for 16 h. The reaction was filtered (Celite) and the filtrate was concentrated at reduced pressure to give an aqueous residue which was extracted with EtOAc (100 mL). The organic layer was separated and washed with sat. EDTA (100 ml) and brine (100 mL), dried (MgSO$_4$), filtered, and concentrated at reduced pressure to give a yellow solid. Trituration with hexane gave the product as a yellow solid (7.1 g, 73%). mp 241–243° C.; CIMS (M+H) calc'd for $C_{13}H_{14}NO_3$: 232.0974, found: 232.0962.

Step 3. Synthesis of 28 from 27.

A solution of 27 (500 mg, 2.16 mmol) in CH2Cl2 (5 mL) was treated with Et3N (0.36 mL, 2.59 mmol) and stirred at 25° C. for 15 min. The reaction mixture was treated with acetyl chloride (0.18 mL, 2.38 mmol) and stirred at 25° C. for 1 h. The reaction mixture was quenched with 1 N HCl (20 mL) and extracted with EtOAc (20 mL). The organic layer was separated, dried (MgSO4), filtered, and concentrated at reduced pressure to give a brown residue. Trituration with hexane gave the product as a tan solid (484 mg, 82%). mp 241–243° C.; CIMS (M+H) calc'd for $C_{15}H_{16}NO_4$: 274.1079, found: 274.1093.

Step 4. Synthesis of 29 from 28.

A solution of 28 (240 mg, 0.88 mmol) in BuOH (5 mL) was treated with hydrazine hydrate (0.055 mL, 1.76 mmol) and p-TsOH (8.4 mg, 0.044 mmol). The reaction was heated to reflux and stirred for 4 h. The reaction was cooled to 25° C. and the solvent removed at reduced pressure. Recrystalization with i-propyl alcohol gave the product collected as an off-white solid (173 mg, 73%). mp >250° C.; ESIMS (M+H) calc'd for $C_{15}H_{16}N_3O_2$: 270.1242, found: 270.1258.

Example LXXXVII

Preparation of 3-(c-propyl)-5-(acetamido)indeno[1,2-c]pyrazol-4-one

Prepared in a similar fashion as described for example LXXXVI using the c-propyl analog of 26 as the starting material. mp 220–221° C.; CIMS (M+H) calc'd for $C_{15}H_{14}N_3O_2$: 268.1086, found: 268.1078.

Example LXXXVIII

Preparation of 3-(t-butyl)-5-(acetamido)indeno[1,2-c]pyrazol-4-one

Prepared in a similar fashion as described for example LXXXVI using the t-butyl analog of 26 as the starting material. mp >250° C.; CIMS (M+H) calc'd for $C_{16}H_{18}N_3O_2$: 284.1399, found: 284.1395.

Example LXXXIX

Preparation of 3-(2-thienyl)-5-(acetamido)indeno[1,2-c]pyrazol-4-one

Prepared in a similar fashion as described for example LXXXVI using the 2-thienyl analog of 26 as the starting material. mp 269° C.; CIMS (M+H) calc'd for $C_{16}H_{12}N_3O_2S$: 310.0650, found: 310.0635.

Example XC

Preparation of 3-(3-methyl-2-thienyl)-5-(acetamido)indeno[1,2-c]pyrazol-4-one

Prepared in a similar fashion as described for example LXXXVI using the 3-methyl-2-thienyl analog of 26 as the starting material. mp 275° C.; ESIMS (M+H) calc'd for $C_{17}H_{14}N_3O_2S$: 324.0811, found: 324.0807.

Example XCI

Preparation of 3-(ethyl)-5-(carbamoyl)aminoindeno[1,2-c]pyrazol-4-one

Prepared in a similar fashion as described for example LXXXVI using ammonia and the ethyl analog of 15 as the starting materials. mp >250° C.; CIMS (M+H) calc'd for $C_{13}H_{13}N_4O_2$: 257.1039, found: 257.1033.

Example XCII

Preparation of 3-(n-propyl)-5-(carbamoyl) aminoindeno[1,2-c]pyrazol-4-one

Prepared in a similar fashion as described for example LXXXVI using ammonia and the n-propyl analog of 15 as the starting materials. mp 187–189° C.; CIMS (M+H) calc'd for $C_{14}H_{15}N_4O_2$: 271.1195, found: 271.1187.

Example XCIII

Preparation of 3-(i-propyl)-5-(carbamoyl) aminoindeno[1,2-c]pyrazol-4-one

Prepared in a similar fashion as described for example LXXXVI using ammonia and the i-propyl analog of 15 as the starting materials. mp >250° C.; CIMS (M+H) calc'd for $C_{14}H_{15}N_4O_2$: 271.1195, found: 271.1196.

Example XCIV

Preparation of 3-(c-propyl)-5-(carbamoyl) aminoindeno[1,2-c]pyrazol-4-one

Prepared in a similar fashion as described for example LXXXVI using ammonia and the c-propyl analog of 15 as the starting materials. mp 252–253° C.; ESIMS (M–H) calc'd for $C_{14}H_{11}N_4O_2$: 267.0881, found: 267.0884.

Example XCV

Preparation of 3-(c-hexyl)-5-(carbamoyl) aminoindeno[1,2-c]pyrazol-4-one

Prepared in a similar fashion as described for example LXXXVI using ammonia and the c-hexyl analog of 15 as the starting materials. mp 178–179° C.; ESIMS (M+H) calc'd for $C_{17}H_{19}N_4O_2$: 311.1507, found: 311.1500.

Example XCVI

Preparation of 3-(2-thienyl)-5-(carbamoyl) aminoindeno[1,2-c]pyrazol-4-one

Prepared in a similar fashion as described for example LXXXVI using ammonia and the 2-thienyl analog of 15 as the starting materials. mp 214° C.; CIMS m+ calc'd for $C_{15}H_{10}N_4O_2S$: 310.0517, found: 310.0524.

Example XCVII

Preparation of 3-(3-methyl-2-thienyl)-5-(carbamoyl) aminoindeno[1,2-c]pyrazol-4-one Prepared in a similar fashion as described for example LXXXVI using ammonia and the 3-methyl-2-thienyl analog of 15 as the starting materials. mp 270° C.; ESIMS (M+H) calc'd for $C_{16}H_{13}N_4O_2S$: 325.0759, found: 325.0744.

Example XCVIII

Preparation of 3-(5-methyl-2-thienyl)-5-(carbamoyl) aminoindeno[1,2-c]pyrazol-4-one Prepared in a similar fashion as described for example LXXXVI using ammonia and the 5-methyl-2-thienyl analog of 15 as the starting materials. mp >280° C.; ESIMS (M+H) calc'd for $C_{16}H_{13}N_4O_2S$: 325.0759, found: 325.0761.

Example XCIX

Preparation of 3-(5-ethylcarboxyl-2-thienyl)-5-(carbamoyl)aminoindeno[1,2-c]pyrazol-4-one Prepared in a similar fashion as described for example LXXXVI using ammonia and the 5-ethylcarboxyl-2-thienyl analog of 15 as the starting materials. mp >280° C.; ESIMS (M+H) calc'd for $C_{18}H_{15}N_4O_4S$: 383.0813, found: 383.0788.

Example C

Preparation of 3-(3-thienyl)-5-(carbamoyl) aminoindeno[1,2-c]pyrazol-4-one

Prepared in a similar fashion as described for example LXXXVI using ammonia and the 3-thienyl analog of 15 as the starting materials. mp >280° C.; ESIMS (M+H) calc'd for $C_{15}H_{11}N_4O_2S$: 311.0603, found: 311.0594.

Example CI

Preparation of 3-(5-chloro-3-thienyl)-5-(carbamoyl) aminoindeno[1,2-c]pyrazol-4-one Prepared in a similar fashion as described for example LXXXVI using ammonia and the 5-chloro-3-thienyl analog of 15 as the starting materials. mp >300° C.; ESIMS (M+H) calc'd for $C_{15}H_{10}N_4O_2SCl$: 345.0209, found: 345.0213.

Example CII

Preparation of 3-(2,5-dimethyl-3-thienyl)-5-(carbamoyl)aminoindeno[1,2-c]pyrazol-4-one Prepared in a similar fashion as described for example LXXXVI using ammonia and the 2,5-dimethyl-3-thienyl analog of 15 as the starting materials. mp >280° C.; ESIMS (M+H) calc'd for $C_{17}H_{15}N_4O_2S$: 339.0916, found: 339.0905.

Example CIII

Preparation of 3-(2-furanyl)-5-(carbamoyl) aminoindeno[1,2-c]pyrazol-4-one

Prepared in a similar fashion as described for example LXXXVI using ammonia and the 2-furanyl analog of 15 as the starting materials. mp 278° C.; ESIMS (M+H) calc'd for $C_{15}H_{11}N_4O_3$: 295.0831, found: 295.0838.

Example CIV

Preparation of 3-(i-propyl)-5-(N,N-dimethylaminocarbamoyl)aminoindeno[1,2-c]pyrazol-4-one Prepared in a similar fashion as described for example LXXXVI using 1,1-dimethylhydrazine and the i-propyl analog of 15 as the starting materials. mp 231–233° C.; ESIMS (M+H) calc'd for $C_{16}H_{20}N_5O_2$: 314.1616, found: 314.1599.

Example CV

Preparation of 3-(c-propyl)-5-(N,N-dimethylaminocarbamoyl)aminoindeno[1,2-c]pyrazol-4-one Prepared in a similar fashion as described for example LXXXVI using 1,1-dimethylhydrazine and the c-propyl analog of 15 as the starting materials. mp XXX ° C.; ESIMS (M+H) calc'd for $C_{16}H_{18}N_5O_2$: 312.1460, found: 312.1487.

Example CVI

Preparation of 3-(c-hexyl)-5-(N,N-dimethylaminocarbamoyl)aminoindeno[1,2-c]pyrazol-4-one Prepared in a similar fashion as described for example LXXXVI using 1,1-dimethylhydrazine and the c-hexyl analog of 15 as the starting materials. mp 229–231° C.; ESIMS (M+H) calc'd for $C_{19}H_{24}N_5O_2$: 354.1929, found: 354.1932.

Example CVII

Preparation of 3-(2-thienyl)-5-(N,N-dimethylaminocarbamoyl)aminoindeno[1,2-c]pyrazol-4-one Prepared in a similar fashion as described for example LXXXVI using 1,1-dimethylhydrazine and the 2-thienyl analog of 15 as the starting materials. mp 279° C.; ESIMS (M+H) calc'd for $C_{17}H_{16}N_5O_2S$: 354.1024, found: 354.1025.

Example CVIII

Preparation of 3-(5-methoxy-2-thienyl)-5-(N,N-dimethylaminocarbamoyl)aminoindeno[1,2-c]pyrazol-4-one Prepared in a similar fashion as described for example LXXXVI using 1,l-dimethylhydrazine and the 5-methoxy-2-thienyl analog of 15 as the starting materials. mp 280° C.; ESIMS (M+H) calc'd for $C_{18}H_{18}N_5O_3S$: 384.1130, found: 384.1119.

Example CIX

Preparation of 3-(5-methyl-2-thienyl)-5-(N,N-dimethylaminocarbamoyl)aminoindeno[1,2-c]pyrazol-4-one Prepared in a similar fashion as described for example LXXXVI using 1,1-dimethylhydrazine and the 5-methyl-2-thienyl analog of 15 as the starting materials. mp >280° C.; ESIMS (M+H) calc'd for $C_{18}H_{18}N_5O_2S$: 368.1181, found: 368.1171.

Example CX

Preparation of 3-(5-ethylcarboxyl-2-thienyl)-5-(N,N-dimethylaminocarbamoyl)aminoindeno[1,2-c]pyrazol-4-one Prepared in a similar fashion as described for example LXXXVI using 11-dimethylhydrazine and the 5-ethylcarboxyl-2-thienyl analog of 15 as the starting materials. mp 252° C.; ESIMS (M+H) calc'd for $C_{20}H_{20}N_5O_4S$: 426.1236, found: 426.1251.

Example CXI

Preparation of 3-(3-thienyl)-5-(N,N-dimethylaminocarbamoyl)aminoindeno[1,2-c]pyrazol-4-one Prepared in a similar fashion as described for example LXXXVI using 1,1-dimethylhydrazine and the 3-thienyl analog of 15 as the starting materials. mp 202° C.; ESIMS (M+H) calc'd for $C_{17}H_{16}N_5O_2S$: 354.1025, found: 354.1031.

Example CXII

Preparation of 3-(1-methyl-3-pyrrolyl)-5-(carbamoyl)aminoindeno[1,2-c]pyrazol-4-one Prepared in a similar fashion as described for example LXXXVI using ammonia and the 1-methyl-3-pyrrolyl analog of 15 as the starting materials. mp >300° C.; ESIMS (M+H) calc'd for $C_{16}H_{14}N_5O_2$: 308.1147, found: 308.1166.

Example CXIII

Preparation of 3-(2,5-dimethyl-3-thienyl)-5-(N,N-dimethylaminocarbamoyl)aminoindeno[1,2-c]pyrazol-4-one Prepared in a similar fashion as described for example LXXXVI using 1,1-dimethylhydrazine and the 2,5-dimethyl-3-thienyl analog of 15 as the starting materials. mp 252° C.; ESIMS (M+H) calc'd for $C_{19}H_{20}N_5O_2S$: 382.1338, found: 382.1357.

Example CXIV

Preparation of 3-(2-furanyl)-5-(N,N-dimethylaminocarbamoyl)aminoindeno[1,2-c]pyrazol-4-one Prepared in a similar fashion as described for example LXXXVI using 1,1-dimethylhydrazine and the 2-furanyl analog of 15 as the starting materials. mp 202° C.; ESIMS (M+H) calc'd for $C_{17}H_{16}N_5O_3$: 338.1253, found: 338.1248.

Example CXV

Preparation of 3-(i-propyl)-5-(4-carbamoylpiperidinylacetamido)indeno[1,2-c]pyrazol-4-one Prepared in a similar fashion as described for example XXIII using isonipecotamide and the i-propyl analog of 14 as the starting materials. mp 224–225° C.; ESIMS (M+H) calc'd for $C_{21}H_{26}N_5O_3$: 396.2035, found: 396.2036.

Example CXVI

Preparation of 3-(c-hexyl)-5-(4-carbamoylpiperidinylacetamido)indeno[1,2-c]pyrazol-4-one Prepared in a similar fashion as described for example XXIII using isonipecotamide and the c-hexyl analog of 14 as the starting materials. mp 228–229° C.; ESIMS (M+H) calc'd for $C_{24}H_{30}N_5O_3$: 436.2348, found: 436.2345.

Example CXVII

Preparation of 3-(ethyl)-5-(4-aminomethylpiperidinylacetamido)indeno[1,2-c]pyrazol-4-one Prepared in a similar fashion as described for example XXIII using 4-(aminomethyl)piperidine and the ethyl analog of 14 as the starting materials. mp 174–176° C.; ESIMS (M+H) calc'd for $C_{20}H_{26}N_5O_2$: 368.2086, found: 368.2078.

Example CXVIII

Preparation of 3-(i-propyl)-5-(4-aminomethylpiperidinylacetamido)indeno[1,2-c]pyrazol-4-one Prepared in a similar fashion as described for example XXIII using 4-(aminomethyl)piperidine and the i-propyl analog of 14 as the starting materials. mp 218–220° C.; ESIMS (M+H) calc'd for $C_{21}H_{28}N_5O_2$: 382.2242, found: 382.2227.

Example CXIX

Preparation of 3-(c-propyl)-5-(4-aminomethylpiperidinylacetamido)indeno[1,2-c]pyrazol-4-one Prepared in a similar fashion as described for example XXIII using 4-(aminomethyl)piperidine and the c-propyl analog of 14 as the starting materials. mp 138–140° C.; ESIMS (M+H) calc'd for $C_{21}H_{26}N_5O_2$: 380.2086, found: 380.2079.

Example CXX

Preparation of 3-(c-hexyl)-5-(4-aminomethylpiperidinylacetamido)indeno[1,2-c]pyrazol-4-one Prepared in a similar fashion as described for example XXIII using 4-(aminomethyl)piperidine and the c-hexyl analog of 14 as the starting materials. mp 196–198° C.; ESIMS (M+H) calc'd for $C_{24}H_{32}N_5O_2$: 422.2555, found: 422.2540.

Example CXXI

Preparation of 3-(i-propyl)-5-(4-methylpiperazinylcarbamoyl)aminoindeno[1,2-c]pyrazol-4-one Prepared in a similar fashion as described for example LXXXVI using 1-amino-4-methylpiperazine and the i-propyl analog of 15 as the starting materials. mp 231–233° C.; ESIMS (M+H) calc'd for $C_{19}H_{25}N_6O_2$: 369.2038, found: 369.2039.

Example CXXII

Preparation of 3-(5-ethylcarboxyl-2-thienyl)-5-(4-methylpiperazinylcarbamoyl)aminoindeno[1,2-c]pyrazol-4-one Prepared in a similar fashion as described for example LXXXVI using 1-amino-4-methylpiperazine and the 5-ethylcarboxyl-2-thienyl analog of 15 as the starting materials. mp 249° C.; ESIMS (M+H) calc'd for $C_{23}H_{25}N_6O_4S$: 481.1657, found: 481.1642.

Example CXXIII

Preparation of 3-(5-carboxyl-2-thienyl)-5-(4-methylpiperazinylcarbamoyl)aminoindeno[1,2-c]pyrazol-4-one A solution of CXXII (30 mg, 0.05 mmol) in 3:1 THF/water (2 mL) was treated with LiOH (23 mg, 0.5 mmol) and the reaction was stirred at 25° C. for 12 h and then heated to reflux for 1 h. The organic solvent was removed at reduced pressure and the residue was partioned between EtOAc (5 mL) and water (5 mL). The organic layer was separated and the aqueous phase was adjusted to pH=2 with 1 M HCl and re-extracted with EtOAc (5 mL). The combined organic layers were dried (Na2SO4), filtered and concentrated at reduced pressure to give a crude residue. Purification by reverse phase HPLC gave the product as a yellow solid (10.4 mg, 46%). mp 270° C.; ESIMS (M+H) calc'd for $C_{21}H_{21}N_6O_4S$: 453.1344, found: 453.1353.

Example CXXIV

Preparation of 3-(2,5-dimethyl-3-thienyl)-5-(4-methylpiperazinylcarbamoyl)aminoindeno[1,2-c]pyrazol-4-one Prepared in a similar fashion as described for example LXXXVI using 1-amino-4-methylpiperazine and the 2,5-dimethyl-3-thienyl analog of 15 as the starting materials. mp 250° C.; ESIMS (M+H) calc'd for $C_{22}H_{25}N_6O_2S$: 437.1760, found: 437.1771.

Example CXXV

Preparation of 3-(i-propyl)-5-(morpholinylcarbamoyl)aminoindeno[1,2-c]pyrazol-4-one Prepared in a similar fashion as described for example LXXXVI using 4-aminomorpholine and the i-propyl analog of 15 as the starting materials. mp 256–258° C.; ESIMS (M−H) calc'd for $C_{18}H_{20}N_5O_3$: 354.1566, found: 354.1543.

Example CXXVI

Preparation of 3-(N-methylcarbamoyl-4-piperidinyl)-5-(morpholinylcarbamoyl)aminoindeno[1,2-c]pyrazol-4-one Prepared in a similar fashion as described for example LXXXVI using 4-aminomorpholine and the N-methylcarbamoyl-4-piperidinyl analog of 15 as the starting materials. mp 216–218° C.; ESIMS (M+H) calc'd for $C_{22}H_{27}N_6O_5$: 455.2042, found: 455.2036.

Example CXXVII

Preparation of 3-(5-methyl-2-thienyl)-5-(morpholinylcarbamoyl)aminoindeno[1,2-c]pyrazol-4-one Prepared in a similar fashion as described for example LXXXVI using 4-aminomorpholine and the 5-methyl-2-thienyl analog of 15 as the starting materials. mp 261° C.; ESIMS (M+H) calc'd for $C_{20}H_{20}N_5O_3S$: 410.1287, found: 410.1308.

Example CXXVIII

Preparation of 3-(5-chloro-3-thienyl)-5-(morpholinylcarbamoyl)aminoindeno[1,2-c]pyrazol-4-one Prepared in a similar fashion as described for example LXXXVI using 4-aminomorpholine and the 5-chloro-3-thienyl analog of 15 as the starting materials. mp 259° C.; ESIMS (M+H) calc'd for $C_{19}H_{17}N_5O_3SCl$: 430.0741, found: 430.0757.

Example CXXIX

Preparation of 3-(2,5-dimethyl-3-thienyl)-5-(morpholinylcarbamoyl)aminoindeno[1,2-c]pyrazol-4-one Prepared in a similar fashion as described for example LXXXVI using 4-aminomorpholine and the 2,5-dimethyl-3-thienyl analog of 15 as the starting materials. mp >280° C.; ESIMS (M+H) calc'd for $C_{21}H_{22}N_5O_3S$: 424.1443, found: 424.1431.

Example CXXX

Preparation of 3-(5-ethylcarboxyl-2-thienyl)-5-(morpholinylcarbamoyl)aminoindeno[1,2-c]pyrazol-4-one Prepared in a similar fashion as described for example LXXXVI using 4-aminomorpholine and the 5-ethylcarboxyl-2-thienyl analog of 15 as the starting materials. mp 258° C.; ESIMS (M+H) calc'd for $C_{22}H_{22}N_5O_5S$: 468.1341, found: 468.1331.

Example CXXXI

Preparation of 3-(5-carboxyl-2-thienyl)-5-(morpholinylcarbamoyl)aminoindeno[1,2-c]pyrazol-4-one Prepared in a similar fashion as described for example LXXXVI (HYDROLYSIS OF PREVIOUS ESTER). mp 273° C.; ESIMS (M+H) calc'd for $C_{20}H_{18}N_5O_5S$: 440.1028, found: 440.1026.

Example CXXXII

Preparation of 3-(5-benzylcarboxamido-2-thienyl)-5-(morpholinylcarbamoyl)aminoindeno[1,2-c]pyrazol-4-one A solution of benzylamine (0.01 mL, 0.09 mmol) in DMF (1 mL) was treated with acid CXXXI (40 mg, 0.09 mmol) and stirred at 25° C. The reaction was treated with TBTU (29 mg, 0.09 mmol) and stirred at 25° C. for 30 min. Triethylamine (0.01 mL, 0.09 mmol) was added and the reaction stirred at 25° C. for 12 h. After adding more TBTU (15 mg, 0.045 mmol) and triethylamine (0.01 mL, 0.09 mmol) the reaction was stirred at 25° C. for an additional 4 h. The reaction was diluted with EtOAc (10 mL) and water (10 mL) and the aqueous layer was extracted with EtOAc (5×10 mL). The combined organic layers were dried (Na2SO4), filtered, and the solvent removed at reduced pressure. Purification of the residue using reverse phase HPLC gave the product as a yellow solid (21 mg, 42%). mp 275° C.; ESIMS (M+H) calc'd for $C_{27}H_{25}N_5O_4S$: 529.1659, found: 529.1682.

Example CXXXIII

Preparation of 3-(5-(4-methylpiperazinyl)carboxamido-2-thienyl)-5-(morpholinylcarbamoyl)aminoindeno[1,2-c]pyrazol-4-one Prepared in a similar fashion as described for example CXXXII using 1-amino-4-methylpiperazine as the starting material. mp 190° C.; ESIMS (M+H) calc'd for $C_{25}H_{29}N_8O_4S$: 537.2032, found: 537.2055.

Example CXXXIV

Preparation of 3-(5-(2-(1-methylpyrrolidinyl)ethyl)carboxamido-2-thienyl)-5-(morpholinylcarbamoyl)aminoindeno[1,2-c]pyrazol-4-one Prepared in a similar fashion as described for example CXXXII using 2-(2-aminoethyl)-1-methylpyrrolidine as the starting material. mp 235° C.; ESIMS (M+H) calc'd for $C_{27}H_{32}N_7O_4S$: 550.2236, found: 550.2229.

Example CXXXV

Preparation of 3-(5-(N,N-dimethylamino)carboxamido-2-thienyl)-5-(morpholinylcarbamoyl)aminoindeno[1,2-c]pyrazol-4-one Prepared in a similar fashion as described for example CXXXII using 1,1-dimethylhydrazine as the starting material. mp 201° C.; ESIMS (M+H) calc'd for $C_{22}H_{24}N_7O_4S$: 482.1610, found: 482.1588.

Example CXXXVI

Preparation of 3-(5-(2-(N,N-dimethylamino)ethyl)carboxamido-2-thienyl)-5-(morpholinylcarbamoyl)aminoindeno[1,2-c]pyrazol-4-one Prepared in a similar fashion as described for example CXXXII using N,N-dimethylethylenediamine as the starting material. mp 190° C.; ESIMS (M+H) calc'd for $C_{24}H_{28}N_7O_4S$: 510.1923, found: 510.1922.

Example CXXXVII

Preparation of 3-(5-(2-(pyrrolidinyl)ethyl)carboxamido-2-thienyl)-5-(morpholinylcarbamoyl)aminoindeno[1,2-c]pyrazol-4-one Prepared in a similar fashion as described for example CXXXII using 1-(2-aminoethyl)pyrrolidine as the starting material. mp 224° C.; ESIMS (M+H) calc'd for $C_{26}H_{30}N_7O_4S$: 536.2080, found: 536.2091.

Example CXXXVIII

Preparation of 3-(5-(2-(morpholinyl)ethyl)carboxamido-2-thienyl)-5-(morpholinylcarbamoyl)aminoindeno[1,2-c]pyrazol-4-one Prepared in a similar fashion as described for example CXXXII using 4-(2-aminoethyl)morpholine as the starting material. mp 241° C.; ESIMS (M+H) calc'd for $C_{26}H_{30}N_7O_5S$: 552.2029, found: 552.2043.

Example CXXXIX

Preparation of 3-(5-morpholinylcarboxamido-2-thienyl)-5-(morpholinylcarbamoyl)aminoindeno[1,2-c]pyrazol-4-one Prepared in a similar fashion as described for example CXXXII using 4-aminomorpholine as the starting material. mp 271° C.; ESIMS (M+H) calc'd for $C_{24}H_{26}N_7O_5S$: 524.1716, found: 524.1719.

Example CXL

Preparation of 3-(5-(3-(pyrrolidonyl)propyl)carboxamido-2-thienyl)-5-(morpholinylcarbamoyl)aminoindeno[1,2-c]pyrazol-4-one Prepared in a similar fashion as described for example CXXXII using 1-(3-aminopropyl)-2-pyrrolidinone as the starting material. mp 260° C.; ESIMS (M+H) calc'd for $C_{27}H_{30}N_7O_5S$: 564.2029, found: 564.2031.

Example CXLI

Preparation of 3-(5-(2-(3-pyridyl)ethyl)carboxamido-2-thienyl)-5-(morpholinylcarbamoyl)aminoindeno[1,2-c]pyrazol-4-one Prepared in a similar fashion as described for example CXXXII using 3-(2-aminoethyl)pyridine as the starting material. mp 203° C.; ESIMS (M+H) calc'd for $C_{27}H_{26}N_7O_4S$: 544.1766, found: 544.1760.

Example CXLII

Preparation of 3-(5-(3-(imidazolyl)propyl)carboxamido-2-thienyl)-5-(morpholinylcarbamoyl)aminoindeno[1,2-c]pyrazol-4-one Prepared in a similar fashion as described for example CXXXII using 1-(3-aminopropyl)imidazole as the starting material. mp 263° C.; ESIMS (M+H) calc'd for $C_{26}H_{27}N_8O_4S$: 547.1875, found: 547.1872.

Example CXLIII

Preparation of 3-(5-(2-(2-pyridyl)ethyl)carboxamido-2-thienyl)-5-(morpholinylcarbamoyl)aminoindeno[1,2-c]pyrazol-4-one Prepared in a similar fashion as described for example CXXXII using 2-(2-aminoethyl)pyridine as the starting material. mp >280° C.; ESIMS (M+H) calc'd for $C_{27}H_{26}N_7O_4S$: 544.1767, found: 544.1778.

Example CXLIV

Preparation of 3-(5-((2-pyridyl)methyl)carboxamido-2-thienyl)-5-(morpholinylcarbamoyl)aminoindeno[1,2-c]pyrazol-4-one Prepared in a similar fashion as described for example CXXXII using 2-(aminomethyl)pyridine as the starting material. mp 239° C.; ESIMS (M+H) calc'd for $C_{26}H_{24}N_7O_4S$: 530.1610, found: 530.1603.

Example CXLV

Preparation of 3-(5-(2-(piperidinyl)ethyl) carboxamido-2-thienyl)-5-(morpholinylcarbamoyl) aminoindeno[1,2-c]pyrazol-4-one Prepared in a similar fashion as described for example CXXXII using 1-(2-aminoethyl)piperidine as the starting material. mp 228° C.; ESIMS (M+H) calc'd for $C_{27}H_{32}N_7O_4S$: 550.2236, found: 550.2236.

Example CXLVI

Preparation of 3-(4-(trifluoromethyl)phenyl)-5-(acetamido)indeno[1,2-c]pyrazol-4-one Prepared in a similar fashion as described for example LXXXVI employing 1-(4-(trifluoromethyl)phenyl)-4,4,4-trifluoro-1,3-butanedione as the starting material. mp >300° C.; ESI⁻-MS m/e calc'd for $C_{19}H_{11}N_3O_2$: 370.0804, found: 370.0809.

Example CXLVII

Preparation of 3-(4-(4-t-butoxycarbonyl-1-piperazinyl)phenyl)-5-(((4-morpholinylamino) carbonyl)amino)indeno[1,2-c]pyrazol-4-one J=9 Hz), 6.87 (d, 2 H, J=9 Hz), 3.59 (m, 4 H), 3.33 (m, 4 H), 2.53 (s, 3 H), 1.49 (s, 9 H).

Step 2. Synthesis of 31 from 30.

To a solution of 30 (11.35 g, 37 mmol) and ethyl trifluoroacetate (5.40 mL, 45 mmol) in 50 mL of tetrahydrofuran at 25° C. was added dropwise over 15 min. 21% sodium ethoxide in ethanol (16.8 mL, 45 mmol), and the resulting solution then was stirred at 25° C. for 14 h. The reaction mixture was diluted with water, adjusted to pH 5 with conc. hydrochloric acid, and extracted with ethyl acetate. The combined extracts was washed with water and brine, dried over anhydrous sodium sulfate, filtered, and concentrated under vacuum. The resulting solid was washed with diethyl ether and dried to furnish 12.1 g (81%) of the product as an orange solid. NMR (CDCl₃) δ7.87 (d, 2 H, J=9 Hz), 6.87 (d, 2 H, J=9 Hz), 6.45 (s, 1 H), 3.60 (m, 4 H), 3.41 (m, 4 H), 1.48 (s, 9 H).

Step 3. Synthesis of CXLVII from 31.

Prepared in a similar fashion as described for examples LXXVI and XLII employing 31 and 4-aminomorpholine as starting materials. mp 242° C.; ESI-MS m/e calc'd for $C_{30}H_{36}N_7O_5$ 574.2778, found: 574.2762.

Example CXLVIII

Preparation of 3-(4-(1-piperazinyl)phenyl)-5-(((4-morpholinylamino)carbonyl)amino)indeno[1,2-c] pyrazol-4-one A solution of CXLVII (0.58 g, 1.0 mmol) in 20 mL of trifluoroacetic acid was stirred at 25° C. for 2 h. The reaction

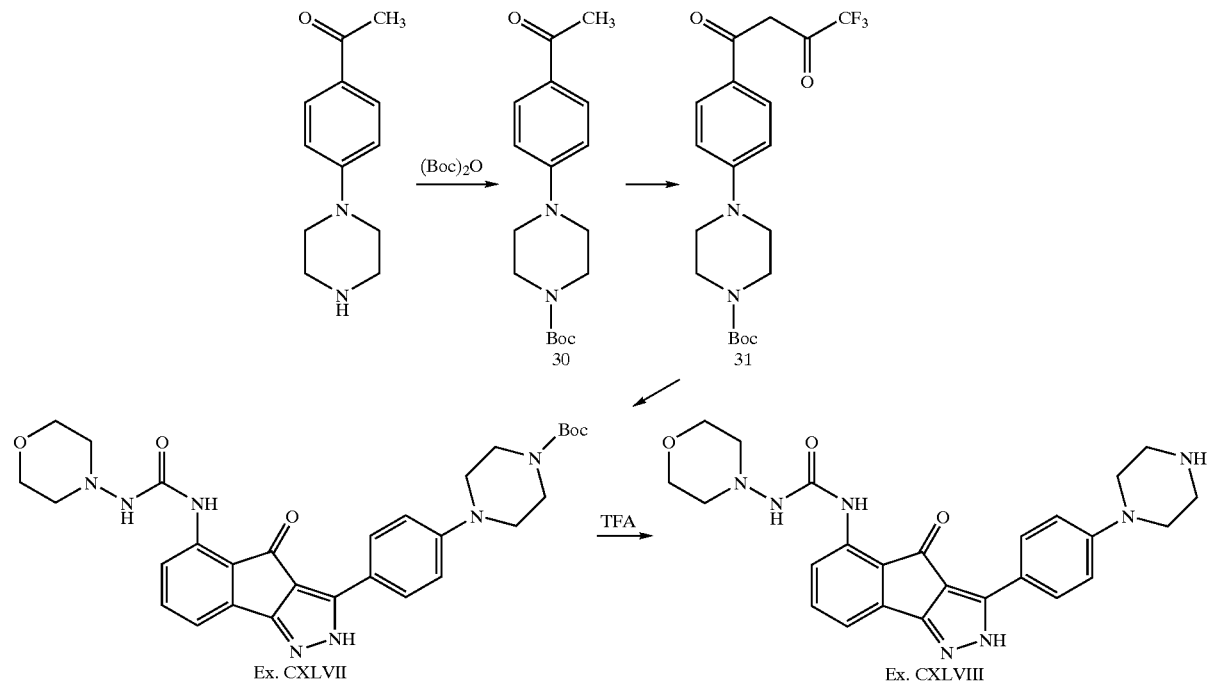

Step 1. Synthesis of 30.

A solution of 4-piperazinoacetophenone (24.8 g, 121 mmol) and di-tert-butyl dicarbonate (27.8 g, 128 mmol) in 480 mL of tetrahydrofuran was refluxed for 16 h. After cooling to room temperature the solution was concentrated under vacuum. The resulting solids were washed with hexane and dried under vacuum to afford 29.4 g (80%) of the product as an off-white solid. NMR (CDCl₃) δ7.89 (d, 2 H, mixture was concentrated under vacuum, and the residue was recrystallized from ethanol to provide 0.53 g (89%) of the yellow product as its TFA-salt. mp 263° C.; ESI-MS m/e calc'd for $C_{25}H_{28}N_7O_3$: 474.2254, found: 474.2280.

Example CXLIX

Preparation of 3-(4-(1-piperazinyl)phenyl)-5-((aminocarbonyl)amino)indeno[1,2-c]pyrazol-4-one Prepared in a similar fashion as described for examples XLII and CXLVIII employing 2-(4-(4-t-butoxycarbonyl-1- piperazinyl)benzoyl)-4-amino-1,3-indanedione obtained in example CXLVII and ammonia as the starting materials. mp 257° C.; ESI-MS m/e calc'd for $C_{21}H_{21}N_6O_2$: 389.1726, found: 389.1724.

Example CL

Preparation of 3-(4-(1-piperazinyl)phenyl)-5-((hydrazinocarbonyl)amino)indeno[1,2-c]pyrazol-4-one Prepared in a similar fashion as described for examples XLII and CXLVIII employing 2-(4-(4-t-butoxycarbonyl-1-piperazinyl)benzoyl)-4-amino-1,3-indanedione obtained in example CXLVII and hydrazine as the starting materials. mp 257° C.; ESI-MS m/e calc'd for $C_{21}H_{22}N_7O_2$: 404.1835, found: 404.1834.

Example CLI

Preparation of 3-(4-(1-piperazinyl)phenyl)-5-((dimethylamino)acetamido)indeno[1,2-c]pyrazol-4-one Prepared employing 2-(4-(4-t-butoxycarbonyl-1-piperazinyl)benzoyl)-4-amino-1,3-indanedione obtained in example CXLVII as the starting material. Chloroacetylation and treatment with dimethylamine in a similar fashion as described for examples II and XXIII, followed by treatment with hydrazine and removal of the t-butoxycarbonyl group in a similar fashion as described for examples I and CXLVIII, afforded the example compound. mp 243° C.; ESI-MS m/e calc'd for $C_{24}H_{27}N_6O_2$: 431.2196, found: 431.2198.

Example CLII

Preparation of 3-(4-(1-piperazinyl)phenyl)-5-((4-morpholinyl)acetamido)indeno[1,2-c]pyrazol-4-one Prepared employing 2-(4-(4-t-butoxycarbonyl-1-piperazinyl)benzoyl)-4-amino-1,3-indanedione obtained in example CXLVII as the starting material. Chloroacetylation and treatment with morpholine in a similar fashion as described for examples II and XXIII, followed by treatment with hydrazine and removal of the t-butoxycarbonyl group in a similar fashion as described for examples I and CXLVIII, afforded the example compound. mp 259° C.; ESI-MS m/e calc'd for $C_{26}H_{29}N_6O_3$: 473.2301, found: 473.2302.

Example CLIII

Preparation of 3-(4-(1-piperazinyl)phenyl)-5-((4-methyl-1-piperazinyl)acetamido)indeno[1,2-c]pyrazol-4-one Prepared employing 2-(4-(4-t-butoxycarbonyl-1-piperazinyl)benzoyl)-4-amino-1,3-indanedione obtained in example CXLVII as the starting material. Chloroacetylation and treatment with 1-methylpiperazine in a similar fashion as described for examples II and XXIII, followed by treatment with hydrazine and removal of the t-butoxycarbonyl group in a similar fashion as described for examples I and CXLVIII, afforded the example compound. ESI-MS m/e calc'd for $C_{27}H_{32}N_7O_2$: 486.2618, found: 486.2608.

Example CLIV

Preparation of 3-(4-(1-piperazinyl)phenyl)-5-((4-amino methyl-1-piperidinyl)acetamido)indeno[1,2-c]pyrazol-4-one Prepared employing 2-(4-(4-t-butoxycarbonyl-1-piperazinyl)benzoyl)-4-amino-1,3-indanedione obtained in example CXLVII as the starting material. Chloroacetylation and treatment with 4-(aminomethyl)piperidine in a similar fashion as described for examples II and XXIII, followed by treatment with hydrazine and removal of the t-butoxycarbonyl group in a similar fashion as described for examples I and CXLVIII, afforded the example compound. mp 239° C.; ESI-MS m/e calc'd for $C_{28}H_{34}N_7O_2$: 500.2774, found: 500.2772.

Example CLV

Preparation of 3-(4-(4-methyl-1-piperazinyl)phenyl)-5-(((4-morpholinylamino)carbonyl)amino)indeno[1,2-c]pyrazol-4-one

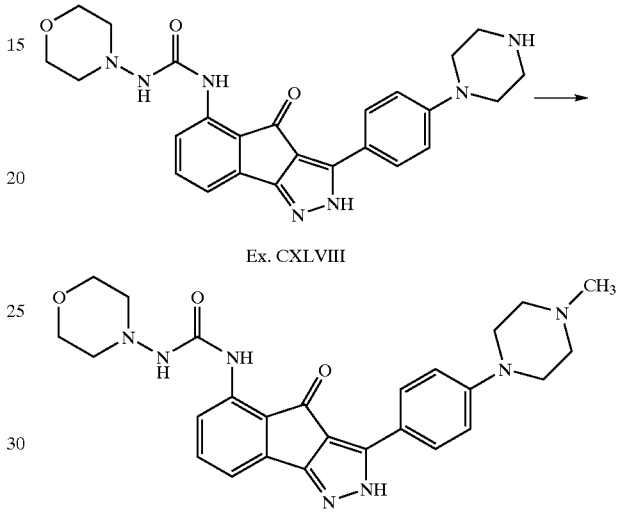

To a solution of CXLVIII (0.17 g, 0.29 mmol) in 10 mL of methanol and 2 mL of water at 25° C. was added sequentially 37% aqueous formaldehyde (0.45 g, 5.8 mmol), sodium cyanoborohydride (0.18 g, 2.9 mmol), and 4 drops of acetic acid. The resulting solution was stirred at 25° C. for 16 h. The mixture was diluted with water. It then was made acidic (~pH 1) with conc. hydrochloric acid and stirred for 10 min. The solution next was made basic (~pH 13) with 50% aqueous sodium hydroxide and finally adjusted to pH 10 with 1 N hydrochloric acid. The mixture was extracted with 4:1 chloroform/isopropanol. The combined extracts were washed with water and brine, dried over anhydrous sodium sulfate, and filtered. To the filtrate was added excess trifluoroacetic acid, and the solution was concentrated under vacuum. The residue was recrystallized from isopropanol to furnish 0.16 g (92%) of the yellow product as its TFA-salt. mp 245° C.; ESI-MS m/e calc'd for $C_{26}H_{30}N_7O_3$: 488.2410, found: 488.2420.

Example CLVI

Preparation of 3-(4-(4-ethyl-1-piperazinyl)phenyl)-5-(((4-morpholinylamino)carbonyl)amino)indeno[1,2-c]pyrazol-4-one Prepared in a similar fashion as described for example CLV employing CXLVIII and acetaldehyde as the starting materials. mp 245° C.; ESI-MS m/e calc'd for $C_{27}H_{32}N_7O_3$: 502.2567, found: 502.2555.

Example CLVII

Preparation of 3-(4-(4-isopropyl-1-piperazinyl)phenyl)-5-(((4-morpholinylamino)carbonyl)amino)indeno[1,2-c]pyrazol-4-one Prepared in a similar fashion as described for example CLV employing CXLVIII and acetone as the starting materials. mp 253° C.; ESI-MS m/e calc'd for $C_{28}H_{34}N_7O_3$: 516.2723, found: 516.2726.

Example CLVIII

Preparation of 3-(4-methoxyphenyl)-5-(2-benzoylhydrazinecarboxamido)indeno[1,2-c]pyrazol-4-one Step 1. Synthesis of 31 from 13.

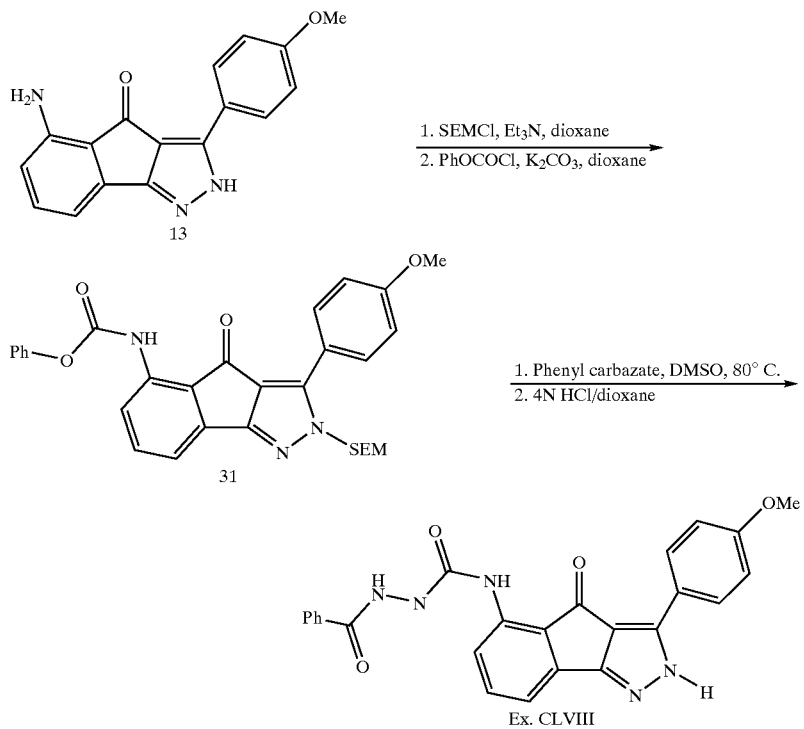

A suspension of aniline 31 (0.5 g, 1.7 mmol) in dioxane (10 mL) was treated with triethylamine (0.48 mL, 3.4 mmol) in one portion at room temperature. Then 2-(trimethylsilyl)ethyloxy chloride (SEMCl) (0.48 mL, 2.6 mmol) was added in one portion and the mixture heated to reflux for 2 h. The reaction was cooled, diluted with EtOAc (20 mL) washed with water (10 mL), dried (MgSO4) and the solvent removed at reduced pressure. The residue was taken up in benzene (3 mL), applied to a plug of silica gel (10 g) and eluted with EtOAc/Hexane (1:3) until all the yellow color was washed from the silica gel plug. The solvent was evaporated and the residue taken on to the next step. This material was dissolved in dioxane (10 mL) and treated with K2CO3 (0.36 g, 2.6 mmol) in one portion. Then phenylchloroformate (0.27 mL, 2.23 mmol) was added in one portion and the reaction heated to 50 C. for 2 h. The reaction was cooled and the solvent removed at reduced pressure. The residue was recrystalized from EtOH to give a yellow solid (0.4 g, 43%). mp °C.; CIMS m/e calculated for $C_{30}H_{32}N_3O_5Si$: 542.2111, found: 542.2101;

Step 2. Synthesis of Ex. CLVIII from 31.

Compound 31 (0.015 g, 0.03 mmol) in DMSO (0.2 mL) was treated with phenylcarbzte (0.008 g, 0.06 mmol) in one portion and heated to 80 C. for 30 minutes. The solvent was removed at reduced pressure heating to 65 C. The residue was disolved in EtOH (0.5 mL) and treated with 4N HCl/dioxane (0.4 mL). The mixture was heated to 80 C. for 20 minutes and then cooled. The desired product was filtered and air dried (0.008 g, 62%). mp >300° C.; CIMS m/e calculated for $C_{26}H_{27}N_4O_4$: 459.2032, found: 459.1999;

Example CLIX

Preparation of 3-(4-methoxyphenyl)-5-(2-isonicotinoylhydrazinecarboxamido)indeno[1,2-c]pyrazol-4-one Prepared in a similar fashion as described for example CLVIII using 4-pyridylcarbazate as the starting material. mp 248° C.; CIMS m/e calculated for $C_{24}H_{19}N_6O_4$: 455.1468, found: 455.1400;

Example CLX

Preparation of 3-(4-methoxyphenyl)-5-(2-nictinoylhydrazinecarboxamido)indeno[1,2-c]pyrazol-4-one Prepared in a similar fashion as described for example CLVIII using 3-pyridylcarbazate as the starting material. mp 227° C.; CIMS m/e calc'd for $C_{24}H_{19}N_6O_4$: 455.1468, found: 455.1487;

Example CLXI

Preparation of 3-(4-methoxyphenyl)-5-(2-(3,4-dihydroxy benzoyl)hydrazinecarboxamido)indeno[1,2-c]pyrazol-4-one Prepared in a similar fashion as described for example CLVIII using 3,4-dihydroxyphenyl carbazate as the starting material. mp >300° C.; CIMS m/e calc'd for $C_{25}H_{20}N_5O_6$: 486.1414, found: 486.1497;

Example CLXII

Preparation of 3-(4-methoxyphenyl)-5-(2-(4-hydroxy benzoyl)hydrazinecarboxamido)indeno[1,2-c]pyrazol-4-one Prepared in a similar fashion as described for example CLVIII using 4-hydroxyphenyl carbazate as the starting material. mp 283° C.; CIMS m/e calc'd for $C_{25}H_{20}N_5O_5$: 470.1464, found: 470.1544;

Example CLXIII

Preparation of 3-(4-methoxyphenyl)-5-(2-(3-aminobenzoyl)hydrazinecarboxamido)indeno[1,2-c]pyrazol-4-one Prepared in a similar fashion as described for example CLVIII using 3-aminophenyl carbazate as the starting material. mp 250° C.; CIMS m/e calc'd for $C_{25}H_{21}N_6O_4$: 469.1624, found: 469.1513;

Example CLXIV

Preparation of 3-(4-methoxyphenyl)-5-(2-(4-aminobenzoyl)hydrazinecarboxamido)indeno[1,2-c]pyrazol-4-one Prepared in a similar fashion as described for example CLVIII using 4-aminophenyl carbazate as the starting material. mp 247° C.; CIMS m/e calc'd for $C_{25}H_{21}N_6O_4$: 469.1624, found: 469.1528;

Example CLXV

Preparation of 3-(4-methoxyphenyl)-5-(2-(2-aminobenzoyl)hydrazinecarboxamido)indeno[1,2-c]pyrazol-4-one Prepared in a similar fashion as described for example CLVIII using 2-aminophenyl carbazate as the starting material. mp 257° C.; CIMS m/e calc'd for $C_{25}H_{21}N_6O_4$: 469.1624, found: 469.1548;

Example CLXVI

Preparation of 3-(4-methoxyphenyl)-5-(2-(4-N,N-dimethylamino benzoyl)hydrazinecarboxamido)indeno[1,2-c]pyrazol-4-one Prepared in a similar fashion as described for example CLVIII using 4-N,N-dimethylaminophenyl carbazate as the starting material. mp 259° C.; CIMS m/e calc'd for $C_{27}H_{25}N_6O_4$: 497.1937, found: 497.1876;

Example CLXVII

Preparation of 3-(4-methoxyphenyl)-5-(2-phenethylacetyl hydrazinecarboxamido)indeno[1,2-c]pyrazol-4-one Prepared in a similar fashion as described for example CLVIII using benzyl carbazate as the starting material. mp 269° C.; CIMS m/e calc'd for $C_{26}H_{22}N_5O_4$: 468.1672, found: 468.1313;

Example CLXVIII

Preparation of 3-(4-methoxyphenyl)-5-(2-(2-hydroxybenzoyl)hydrazinecarboxamido)indeno[1,2-c]pyrazol-4-one Prepared in a similar fashion as described for example CLVIII using 2-hydroxyphenyl carbazate as the starting material. mp 280° C.; CIMS m/e calc'd for $C_{25}H_{20}N_5O_5$: 470.1464, found: 470.1419;

Example CLXIX

Preparation of 3-(4-methoxyphenyl)-5-(2-methoxycarbonylhydrazinecarboxamido)indeno[1,2-c]pyrazol-4-one Prepared in a similar fashion as described for example CLVIII using carbazic acid methyl ester as the starting material. mp >300° C.; CIMS m/e calc'd for $C_{20}H_{28}N_5O_5$: 408.1308, found: 408.1397;

EXAMPLE CLXX

Preparation of Intermediate CLXX

The preparation of intermediate CLXX, (N-[2-(4-Methoxy-benzoyl)-1,3-dioxo-indan-4-yl]-acetamide) is described in Nugiel, D. A.; Etzkorn, A. M.; Vidwans, A.; Benfield, P. A.; Boisclair, M.; Burton, C. R.; Cox, S.; Czerniak, P. M.; Doleniak, D.; Seitz, S. P. J. Med. Chem. 2001, 44, 1334–1336 which is herein incorporated by reference in it's entirety as though set forth in full.

EXAMPLE CLXXI

Preparation of Intermediate CLXXI

Synthesis of 4-Amino-2-(4-methoxy-benzoyl)-indan-1,3-dione: The compound prepared in example 1 (2.0 g, 5.93 mmol) is dissolved in 20% HCl in methanol (50 mL). This solution is stirred at reflux for a period of 3 h. It is then allowed to cool to room temperature and stirred overnight. The product is filtered off, washed with ethanol (20 mL) and air dried to give the product as a yellow solid (1.5 g, 85.7%). mp 268–269° C.; $^1$H NMR (DMSOd$_6$) δ8.17 (d, J=8.8 Hz, 2H), 7.49 (t, 1H), 7.12 (d, J=8.7 Hz, 2H), 6.98 (m, 2H), 3.88 (s, 1H).

EXAMPLE CLXXII

Preparation of Intermediate CLXXII

Synthesis of [2-(4-Methoxybenzoyl)-1,3-dioxo-indan-4-yl]-carbamic acid phenyl ester: The product prepared in Example CLXXI (1.5 g, 5.08 mmol) is dissolved in acetone (40 mL) and treated with sodium carbonate (1.26 g, 15.24 mmol) and phenyl chloroformate (1.19 g, 7.62 mmol). The suspension is stirred at 50° C. for 3 h. The reaction mixture is diluted with water (120 mL), and extracted with ethyl acetate (2×100 mL). The organic layer is separated, washed with brine (50 mL), dried (Na$_2$SO$_4$) and the solvent removed at reduced pressure to give a gummy orange residue. Cold ethyl ether (100 mL) is added to this residue to give a precipitate. The precipitate is collected and washed with ethyl ether (2×10 mL) to give desired product as a yellow solid (1.65 g. 78%). mp 256–258° C.; $^1$H NMR (DMSOd$_6$) δ10.83 (s, 1H), 8.08 (d, J=8.0 Hz, 1H), 7.57 (d, J=2.9 Hz, 2H), 7.54 (m, 3H), 7.28 (m, 3H), 7.09 (t, 1H), 6.89 (d, J=10.8 Hz, 2H), 3.81 (s, 3H).

EXAMPLE CLXXIII

Preparation of 1-[3-(4-methoxy-phenyl)-4-oxo-2,4-dihydro-indeno[1,2-c]pyrazol-5-yl]-3-morpholin-4-yl-urea

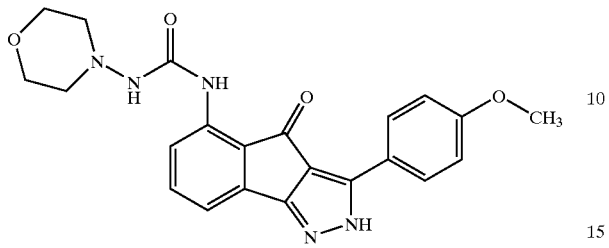

The product prepared in Example CLXXII (0.03 g, 0.072 mmol) in anhydrous DMSO (2 mL) is treated with 4-aminomorpholine (0.0084 g, 0.082 mmol) and 4-dimethylaminopyridine (0.005 g, 0.04 mmol) and heated to 80° C. for 3 h. The solvent is removed under reduced pressure and the residue triturated with ethanol to give a dark solid. The solid is collected and washed with ethanol (5 mL) to give a tricarbonyl urea (0.03 g, 100%). The tricarbonyl urea intermediate (0.03 g, 0.078 mmol) is treated with hydrazine hydrate (0.1 mL, 3.21 mmol) and p-toluenesulfonic acid monohydrate (0.01 g, 0.05 mmol) in refluxing ethanol (4 mL) for a period of 3 h. The reaction mixture is cooled to room temperature, the solid collected, washed with cold ethanol (2×2 mL), and air dried to give the product as a yellowish solid (0.012 g, 41.3%). mp 290–291° C.; $^1$H NMR (DMSO-$d_6$) δ8.27 (d, J=6.8 Hz, 2H), 8.16 (d, J=8.8 Hz, 2H), 7.42 (m, 1H), 7.12 (m, 3H), 3.81 (s, 3H), 2.90 (s, 4H), 2.70 (s, 4H), HRMS calcd. for $C_{22}H_{22}N_5O_4$ (M+H$^+$) 420.1672; found 420.1688;

EXAMPLE CLXXIV

Preparation of [3-(4-methoxy-phenyl)-4-oxo-2,4-dihydro-indeno[1,2-c]pyrazol-5-yl]-urea

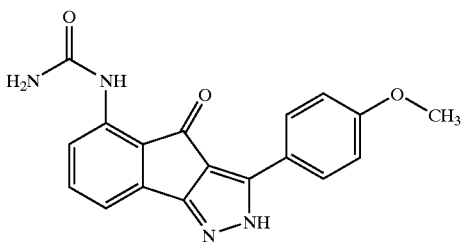

The product prepared in Example CLXXII (0.03 g, 0.072 mmol) in anhydrous DMSO (2 mL) is treated with excess ammonium hydroxide solution and 4-dimethylaminopyridine (0.005 g, 0.04 mmol) and is heated to 80° C. for 3 h. The solvent is removed under reduced pressure and the residue triturated with ethanol to give a dark solid. The solid is collected and washed with ethanol (5 mL) to give urea (0.03 g, 100%). The tricarbonyl urea intermediate (0.03 g, 0.078 mmol) is treated with hydrazine hydrate (0.1 mL, 3.21 mmol) and p-toluenesulfonic acid monohydrate (0.01 g, 0.05 mmol) in refluxing ethanol (4 mL) for a period of 3 h. The reaction mixture is cooled to room temperature, the solid collected, washed with cold ethanol (2×2 mL), and air dried to give the product as a yellowish solid (0.018 g, 62.4%). mp 267–269° C.; $^1$H NMR (DMSO-$d_6$) δ9.35 (s, 1H), 8.22 (m, 3H), 7.38 (m, 1H), 7.10 (d, J=8.8 Hz, 2H), 7.02 (d, J=7 Hz, 1H), 3.81 (s, 3H); HRMS calcd. for $C_{18}H_{15}N_4O_3$ (M+H$^+$) 335.1144; found 335.1162;

EXAMPLE CLXXV

Preparation of 1-(2-amino-cyclohexyl)-3-[3-(4-methoxy-phenyl)-4-oxo-2,4-dihydro-indeno[1,2-c]pyrazol-5-yl]-urea

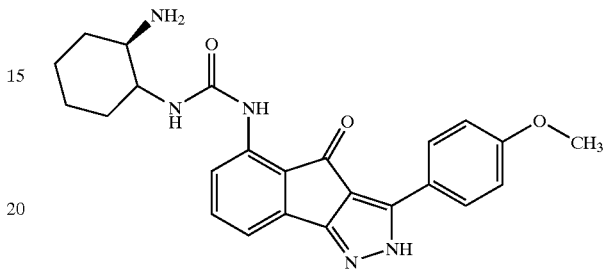

The product prepared in Example CLXXII (0.03 g, 0.072 mmol) in anhydrous DMSO (2 mL) is treated with 1,2-diaminocyclohexane (0.01 g, 0.082 mmol) and 4-dimethylaminopyridine (0.005 g, 0.04 mmol) and heated to 80° C. for 3 h. The solvent is removed under reduced pressure and the residue triturated with ethanol to give a dark solid. The solid is collected and washed with ethanol (5 mL) to give a tricarbonyl urea (0.03 g, 100%). The tricarbonyl urea intermediate (0.03 g, 0.078 mmol) is treated with hydrazine hydrate (0.1 mL, 3.21 mmol) and p-toluenesulfonic acid monohydrate (0.01 g, 0.05 mmol) in refluxing ethanol (4 mL) for a period of 3 h. The reaction mixture is cooled to room temperature, the solid collected, washed with cold ethanol (2×2 mL), and air dried to give the product as a yellowish solid (0.01 g, 30.6%). $^1$HNMR (DMSO-$d_6$) δ9.56 (s, 1H), 8.27 (d, 1H), 8.19 (d, 2H), 7.41 (t, 1H), 7.10 (m, 3H), 4.10 (s, 1H), 3.81 (s, 3H), 3.23 (s, 1H), 1.63 (m, 5H), 1.40 (m, 3H).

EXAMPLE CLXXVI

Preparation of 5-Amino-3-(4-methoxyphenyl)-2-phenyl-2H-indeno-[1,2-c]pyrazol-4-one:

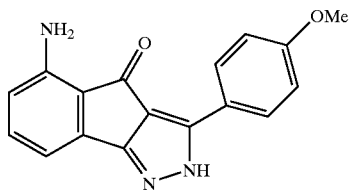

A suspension of N-[3-(4-Methoxy-phenyl)-4-oxo-2,4-dihydro-indeno[1,2-c]pyrazol-5-yl]-acetamide (as produced according to Nugiel, D. A.; Etzkorn, A. M.; Vidwans, A.; Benfield, P. A.; Boisclair, M.; Burton, C. R.; Cox, S.; Czerniak, P. M.; Doleniak, D.; Seitz, S. P. J. Med. Chem. 2001, 44, 1334–1336) (1.0 g, 3.0 mmol) in MeOH (10 mL) was treated with concentrated HCl (1 mL) and heated to reflux. After stirring the mixture for 2 h the reaction was cooled and the product was collected by filtration and obtained as a greenish solid (0.7 g, 81%). mp 273° C.; NMR (DMSO-d$_6$) δ13.6 (bs, 1 H), 8.3 (d, J=8.4 Hz, 1 H), 8.1 (d, J=8.8 Hz, 2 H), 7.5 (t, J=7.7 Hz 1 H), 7.2 (d, J=7.0 Hz, 1 H), 7.1 (d, J=8.8 Hz, 2 H), 3.8 (s, 3 H); HRMS m/e calc'd for C$_{17}$H$_{14}$N$_3$O$_2$ (M+H): 292.1086, found: 292.1080.

EXAMPLE CLXXVII

Preparation of 2-Chloro-N-[3-(4-methoxyphenyl)-4-oxo-2,4-dihydro-indeno[1,2-c]pyrazol-5-yl]-acetamide

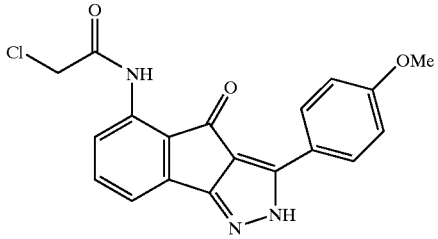

A suspension of the product prepared in Example CLXXVI (0.2 g, 0.7 mmol) in dioxane (10 mL) was treated with aqueous saturated NaHCO$_3$ (3 mL) and chloroacetyl chloride (3 mL, 0.21 mmol). The reaction was heated to 50° C. and stirred for 2 h. The reaction is then cooled, poured into water (20 mL), extracted with EtOAc (100 mL), the organic layer separated, dried (MgSO$_4$) and the solvent removed at reduced pressure. The residue is recrystallized from EtOH to give the product as a yellow solid (0.09 g, 35%). mp >300° C.; NMR (DMSO-d$_6$) δ13.6 (bs, 1 H), 11.3 (s, 1 H), 8.3 (d, J=8.4 Hz, 1 H), 8.1 (d, J=8.8 Hz, 2 H), 7.5 (t, J=7.7 Hz 1 H), 7.2 (d, J=7.0 Hz, 1 H), 7.1 (d, J=8.8 Hz, 2 H), 4.5 (s, 2 H), 3.8 (s, 3 H); HRMS m/e calc'd for C$_{19}$H$_{15}$N$_3$O$_3$Cl (M+H): 368.0802, found: 368.0818.

EXAMPLE CLXXVIII

Preparation of 2-(4-aminomethyl-piperidin-1-yl)-N-[3-(4-methoxy-phenyl)-4-oxo-2,4-dihydro-indeno[1,2-c]pyrazol-5-yl]-acetamide

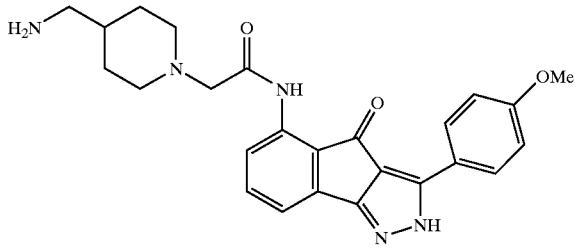

A suspension of product prepared according to Example CLXXVII (0.015 g, 0.04 mmol) in EtOH (1 mL) is treated with 4-aminomethylpiperdine (0.75 mL), placed in a sealed tube and heated to 80° C. for 3 h. The reaction is cooled and the solvent removed at reduced pressure. The residue is recrystallized from EtOH to give the product as a yellow solid (0.009 g, 62%). mp >300° C.; NMR (DMSO-d$_6$) δ13.6 (bs, 1 H), 11.3 (s, 1 H), 8.35 (d, J=8.4 Hz, 1 H), 8.1 (d, J=8.8 Hz, 2 H), 7.5 (t, J=7.7 Hz 1 H), 7.2 (d, J=7.0 Hz, 1 H), 7.1 (d, J=8.8 Hz, 2 H), 3.8 (s, 3 H), 3.2 (bs, 2 H), 2.9(bs, 2 H), 2.5 (d, J=8.0 Hz, 2 H), 2.2 (t, J=8.0 Hz, 2 H), 1.6 (m, 5 H); HRMS m/e calc'd for C$_{25}$H$_{28}$N$_5$O$_3$ (M+H): 446.2192, found: 446.2169; Anal. (C$_{25}$H$_{27}$N$_5$O$_3$) C, H, N.

EXAMPLE CLXXIX

Preparation of 2-(4-Methoxybenzoyl)-3-methoxycarbonylamino-indan-1,3-dione

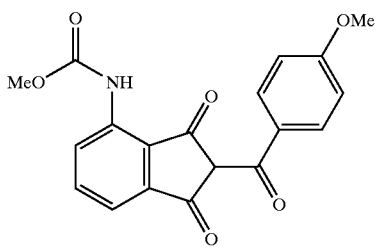

A solution of 3-methoxycarbonylamino-phthalic acid dimethyl ester (1 g, 4.8 mmol) and 4-methoxyacetophenone (0.72 g, 4.8 mmol) in dry DMF (3 mL) was heated to 90° C. Sodium hydride (0.21 g, 60% suspension in oil, 5.2 mmol) is added in one portion and the exothermic reaction turns deep red. After 20 min, the reaction is cooled to room temperature, diluted with water (25 mL) extracted with EtOAc (10 mL) and the aqueous phase separated. The aqueous phase is acidified to pH 2 with 2N HCl and the crude product collected. Recrystallization with ethanol gives the desired product as a yellow solid (0.4 g, 30%). ESIMS 352 (M–H, 100%).

EXAMPLE CLXXX

Preparation of 3-(4-Methoxyphenyl)-5-methoxycarbonylamino-2H-indeno-[1,2-c]pyrazol-4-one

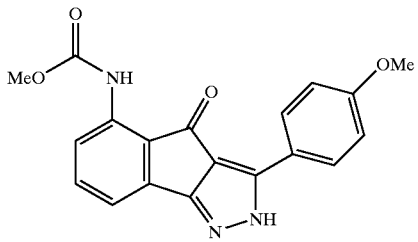

A solution of 2-(4-methoxybenzoyl)-3-methoxycarbonylamino-indan-1,3-dione (0.2 g, 0.6 mmol) in EtOH (5 mL) is treated with hydrazine hydrate (0.1 mL, 1.8 mmol) and p-TsOH (3 mg). The reaction is heated to reflux and stirred for 2 h. The reaction is cooled to room temperature and the product crystallized from the reaction mixture. The product is collected by filtration as a yellow solid (0.1 g, 50%). mp >300° C.; HRMS m/e calc'd for C$_{19}$H$_{16}$N$_3$O$_4$ (M+H): 350.1141, found: 350.1168.

Utility

Inhibition of Kinase/Cyclin Complex Enzymatic Activity

Several of the compounds disclosed in this invention were assayed for their inhibitory activity against cdk4/D1 and cdk2/E kinase complexes. Briefly, the in vitro assays employ cell lysates from insect cells expressing either of the kinases and subsequently their corresponding regulatory units. The cdk2/cyclinE is purified from insect cells expressing His-tagged cdk2 and cyclin E. The cdk/cyclin lysate is combined in a microtitre-type plate along with a kinase compatible buffer, $^{32}$P-labeled ATP at a concentration of 50 mM, a GST-Rb fusion protein and the test compound at varying concentrations. The kinase reaction is allowed to proceeded with the radiolabled ATP, then effectively stopped by the addition of a large excess of EDTA and unlabeled ATP. The GST-Rb labeled protein is sequestered on a GSH-Sepharose bead suspension, washed, resuspended in scintillant, and the $^{32}$P activity detected in a scintillation counter. The compound concentration which inhibits 50% of the kinase activity was calculated for each compound. A compound was considered active if its IC$_{50}$ was found to be less than 1 μM.

Inhibition of HCT 116 Cancer Cell Proliferation

To test the cellular activity of several compounds disclosed in this invention, we examined the effect of these compounds on cultured HCT116 cells and determined their effect on cell-cycle progression by the calorimetric cytotoxcity test using sulforhodamine B (Skehan et al. J. Natl. Cancer Inst. 82:1107–12, 1990). Briefly, HCT116 cells are cultured in the presence of test compounds at increasing concentrations. At selected time points, groups of cells are fixed with trichloroacetic acid and stained with sulforhodamine B (SRB). Unbound dye was removed by washing and protein-bound dye was extracted for determination of optical density. A compound was considered active if its IC$_{50}$ was found to be less than 10 μM.

TABLE 1

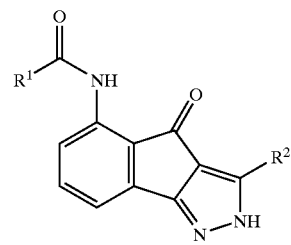

| Example # | R$^1$ | R$^2$ | mass (M$^+$H) | mp (° C.) |
|---|---|---|---|---|
| I | Methyl | 4-MeOC$_6$H$_4$ | 334 | 268 |
| II | ClCH$_2$ | 4-MeOC$_6$H$_4$ | 382 | 274 |
| III | Cyclopropyl | 4-MeOC$_6$H$_4$ | 360 | 289 |
| IV | Isopropyl | 4-MeOC$_6$H$_4$ | 362 | 288 |
| V | Ethyl | 4-MeOC$_6$H$_4$ | 348 | 287 |
| VI | Cyclopentyl | 4-MeOC$_6$H$_4$ | 388 | 267 |
| VII | Cyclobutyl | 4-MeOC$_6$H$_4$ | 374 | 297 |
| VIII | Benzyl | 4-MeOC$_6$H$_4$ | 410 | 280 |
| IX | n-propyl | 4-MeOC$_6$H$_4$ | 362 | 282 |
| X | 4-ClC$_6$H$_4$CH$_2$ | 4-MeOC$_6$H$_4$ | 444 | 238 |
| XI | 3-MeOC$_6$H$_4$CH$_2$ | 4-MeOC$_6$H$_4$ | 440 | >300 |
| XII | 4-MeOC$_6$H$_4$CH$_2$ | 4-MeOC$_6$H$_4$ | 440 | 280 |
| XIII | 3,4-diMeOC$_6$H$_4$CH$_2$ | 4-MeOC$_6$H$_4$ | 470 | >300 |
| XIV | 2,5-diMeOC$_6$H$_4$CH$_2$ | 4-MeOC$_6$H$_4$ | 470 | 226 |
| XV | Methyl | 2-MeOC$_6$H$_4$ | 334 | 276 |
| XVI | Methyl | 3,4-diMeOC$_6$H$_4$ | 364 | >300 |
| XVII | 3,4-(OCH$_2$O)C$_6$H$_4$CH$_2$ | 4-MeOC$_6$H$_4$ | 454 | 297 |
| XVIII | 3-thiophenylCH$_2$ | 4-MeOC$_6$H$_4$ | 416 | 293 |
| XIX | 2-MeOC$_6$H$_4$CH$_2$ | 4-MeOC$_6$H$_4$ | 440 | 255 |
| XX | 3,4-diClOC$_6$H$_4$CH$_2$ | 4-MeOC$_6$H$_4$ | 479 | 299 |
| XXI | 2,4-diClOC$_6$H$_4$CH$_2$ | 4-MeOC$_6$H$_4$ | 479 | 286 |
| XXII | 2-ClC$_6$H$_4$CH$_2$ | 4-MeOC$_6$H$_4$ | 444 | 300 |
| XXIII | H$_2$NCH$_2$ | 4-MeOC$_6$H$_4$ | 349 | >300 |
| XXIV | HOCH$_2$CH$_2$NHCH$_2$ | 4-MeOC$_6$H$_4$ | 393 | 243 |
| XXV | Me$_2$NCH$_2$ | 4-MeOC$_6$H$_4$ | 377 | 279 |
| XXVI | piperazinylCH$_2$ | 4-MeOC$_6$H$_4$ | 418 | 277 |
| XXVII | 4-Me-piperazinylCH$_2$ | 4-MeOC$_6$H$_4$ | 432 | >300 |
| XXVIII | 4-HOCH$_2$CH$_2$-piperazinylCH$_2$ | 4-MeOC$_6$H$_4$ | 462 | >300 |
| XXIX | piperidinylCH$_2$ | 4-MeOC$_6$H$_4$ | 417 | 291 |
| XXX | 4-NH$_2$CH$_2$-piperidinylCH$_2$ | 4-MeOC$_6$H$_4$ | 446 | >300 |
| XXXI | CH$_3$CH$_2$NHCH$_2$ | 4-MeOC$_6$H$_4$ | 377 | 250 |
| XXXII | ThiomorpholinylCH$_2$ | 4-MeOC$_6$H$_4$ | 435 | 298 |
| XXXIII | morpholinylCH$_2$ | 4-MeOC$_6$H$_4$ | 419 | 295 |
| XXXIV | pyrrolidinylCH$_2$ | 4-MeOC$_6$H$_4$ | 403 | 279 |
| XXXV | 4-pyridylCH$_2$NHCH$_2$ | 4-MeOC$_6$H$_4$ | 440 | >300 |
| XXXVI | 4-CH$_3$CONHC$_6$H$_4$CH$_2$ | 4-MeOC$_6$H$_4$ | 467 | 268 |
| XXXVII | 4-CH$_3$OCONHC$_6$H$_4$CH$_2$ | 4-MeOC$_6$H$_4$ | 483 | 257 |
| XXXVIII | 4-NH$_2$CH$_2$CONHC$_6$H$_4$CH$_2$ | 4-MeOC$_6$H$_4$ | 482 | 228 |
| XXXIX | 4-Me$_2$NCH$_2$CONHC$_6$H$_4$CH$_2$ | 4-MeOC$_6$H$_4$ | 510 | >300 |
| XL | 4-N$_3$C$_6$H$_4$CH$_2$ | 4-MeOC$_6$H$_4$ | 451 | >300 |
| XLI | 4-NH$_2$C$_6$H$_4$CH$_2$ | 4-MeOC$_6$H$_4$ | 425 | 283 |
| XLII | C$_6$H$_5$NH | 4-MeOC$_6$H$_4$ | 411 | >300 |
| XLIII | CH$_3$CH$_2$CH$_2$NH | 4-MeOC$_6$H$_4$ | 377 | 252 |
| XLIV | 4-NH$_2$C$_6$H$_4$CH$_2$NH | 4-MeOC$_6$H$_4$ | 440 | >300 |

TABLE 1-continued

[Chemical structure: R¹-C(=O)-NH- substituted indeno-pyrazolone with R² substituent]

| Example # | R¹ | R² | mass (M⁺H) | mp (° C.) |
|---|---|---|---|---|
| XLV | 4-pyridylCH₂NH | 4-MeOC₆H₄ | 426 | >300 |
| XLVI | Methyl | 4-HOC₆H₄ | 320 | >300 |
| XLVII | H | 4-MeOC₆H₄ | 320 | 280 |
| XLVIII | Methyl | 3-pyridyl | 305 | >300 |
| XLIX | Methyl | 4-pyridyl | 305 | >300 |
| L | H | 4-pyridyl | 291 | >300 |
| LI | Methyl | C₆H₅ | 305 | >300 |
| LII | Methyl | 4-MeSC₆H₄ | 351 | 283 |
| LIII | Methyl | 4-MeSO₂C₆H₄ | 383 | >300 |
| LVI | Methyl | 4-Me₂NC₆H₄ | 348 | >300 |
| LV | morpholinylCH₂ | 4-Me₂NC₆H₄ | 432 | >300 |
| LVI | Me₂NCH₂ | 4-Me₂NC₆H₄ | 390 | >300 |
| LVII | Methyl | 4-(piperdinyl)C₆H₄ | 388 | 291 |
| LVIII | Methyl | 4-(morpholinyl)C₆H₄ | 389 | >300 |
| LIX | Methyl | 4-CH₃CH₂OC₆H₄ | 349 | 288 |
| LX | Methyl | 4-CH₃CH₂CH₂CH₂C₆H₄ | 361 | 259 |
| LXI | Methyl | 4-CH₃CH₂C₆H₄ | 332 | 294 |
| LXII | Methyl | 4-CH₃CH₂CH₂C₆H₄ | 347 | 269 |
| LXIII | NH₂ | 4-MeOC₆H₄ | 335 | >300 |
| LXIV | Me2NNH | 4-MeOC₆H₄ | 378 | >300 |
| LXV | MeNH | 4-MeOC₆H₄ | 349 | >300 |
| LXVI | MorpholinylNH | 4-MeOC₆H₄ | 420 | >300 |
| LXVII | cis-1,2-diaminocyclohexanyl | 4-MeOC₆H₄ | 432 | >300 |
| LXVIII | 4-methyl-piperazinylNH | 4-MeOC₆H₄ | 433 | >300 |
| LXVIX | 4-uridomethyl-piperadinylCH₂ | 4-MeOC₆H₄ | 489 | >300 |
| LXX | 4-(2-pyridyl)-piperazinyl CH₂ | 4-MeOC₆H₄ | 495 | >300 |
| LXXI | 4-(aminoethyl)-piperazinyl CH₂ | 4-MeOC₆H₄ | 461 | >300 |
| LXXII | 4-amidopiperidinylCH₂ | 4-MeOC₆H₄ | 460 | >300 |
| LXXIII | 4-hydroxy-piperidinylCH₂ | 4-MeOC₆H₄ | 433 | >300 |
| LXXIV | 4-hydroxy-methylpiperidinylCH₂ | 4-MeOC₆H₄ | 447 | >300 |
| LXXV | 4-amidopiperazinylCH₂ | 4-MeOC₆H₄ | 493 | >300 |
| LXXVI | 4-dimethyl-aminopiperadinylCH₂ | 4-MeOC₆H₄ | 492 | >300 |
| LXXVII | 4-aminopiperadinylCH₂ | 4-MeOC₆H₄ | 464 | >300 |
| LXXVIII | 4-Me-piperazinylCH₂ | 4-Me₂NC₆H₄ | 445 | >300 |
| LXXIX | 4-NH₂CH₂-piperidinylCH₂ | 4-Me₂NC₆H₄ | 459 | NA |
| LXXX | 4-OH-piperidinylCH₂ | 4-Me₂NC₆H₄ | 446 | 267 |
| LXXXI | morpholinylCH₂ | 4-(morpholinyl)C₆H₄ | 474 | 258 |
| LXXXII | 4-Me-piperazinylCH₂ | 4-(morpholinyl)C₆H₄ | 487 | 258 |
| LXXXIII | 4-OH-piperidinylCH₂ | 4-(morpholinyl)C₆H₄ | 488 | 245 |
| LXXXIV | 4-NH₂CH₂-piperidinylCH₂ | 4-(morpholinyl)C₆H₄ | 501 | 240 |
| LXXXV | 4-Me-piperazinylNH | 4-Me₂NC₆H₄ | 446 | >300 |
| LXXXVI | Methyl | i-propyl | 270 | >250 |
| LXXXVII | Methyl | c-propyl | 268 | 220 |
| LXXXVIII | Methyl | t-butyl | 284 | >250 |
| LXXXIX | Methyl | 2-thienyl | 310 | 269 |
| XC | Methyl | 3-Me-2-thienyl | 324 | 275 |
| XCI | NH₂ | Ethyl | 257 | >250 |
| XCII | NH₂ | n-propyl | 271 | 187 |
| XCIII | NH₂ | i-propyl | 271 | >250 |
| XCIV | NH₂ | c-propyl | 267 (M − H) | 252 |
| XCV | NH₂ | c-hexyl | 311 | 178 |
| XCVI | NH₂ | 2-thienyl | 310 | 214 |

TABLE 1-continued

| Example # | R¹ | R² | mass (M⁺H) | mp (° C.) |
|---|---|---|---|---|
| | | | (M+) | |
| XCVII | NH₂ | 3-Me-2-thienyl | 325 | 270 |
| XCVIII | NH₂ | 5-Me-2-thienyl | 325 | >280 |
| XCIX | NH₂ | 5-CO₂Et-2-thienyl | 383 | >280 |
| C | NH₂ | 3-thienyl | 311 | >280 |
| CI | NH₂ | 5-Cl-3-thienyl | 345 | >300 |
| CII | NH₂ | 2,5-diMe-3-thienyl | 339 | >280 |
| CIII | NH₂ | 2-furanyl | 295 | 278 |
| CIV | Me₂NNH | i-propyl | 314 | 231 |
| CV | Me₂NNH | c-propyl | 312 | |
| CVI | Me₂NNH | c-hexyl | 354 | 229 |
| CVII | Me₂NNH | 2-thienyl | 354 | 279 |
| CVIII | Me₂NNH | 5-MeO-2-thienyl | 384 | 280 |
| CIX | Me₂NNH | 5-Me-2-thienyl | 368 | >280 |
| CX | Me₂NNH | 5-CO₂Et-2-thienyl | 426 | 252 |
| CXI | Me₂NNH | 3-thienyl | 354 | 202 |
| CXII | NH₂ | 1-methyl-3-pyrrolyl | 308 | >300 |
| CXIII | Me₂NNH | 2,5-diMe-3-thienyl | 382 | 252 |
| CXIV | Me₂NNH | 2-furanyl | 338 | 202 |
| CXV | 4-NH₂CO-piperidinylCH₂ | i-propyl | 396 | 224 |
| CXVI | 4-NH₂CO-piperidinylCH₂ | c-hexyl | 436 | 228 |
| CXVII | 4-NH₂CH₂-piperidinylCH₂ | ethyl | 368 | 174 |
| CXVIII | 4-NH₂CH₂-piperidinylCH₂ | 1-propyl | 382 | 218 |
| CXVIX | 4-NH₂CH₂-piperidinylCH₂ | c-propyl | 380 | 138 |
| CXX | 4-NH₂CH₂-piperidinylCH₂ | c-hexyl | 422 | 196 |
| CXXI | 4-CH₃-piperazinylNH | i-propyl | 369 | 231 |
| CXXII | 4-CH₃-piperazinylNH | 5-CO₂Et-2-thienyl | 481 | 249 |
| CXXIII | 4-CH₃-piperazinylNH | 5-CO₂H-2-thienyl | 453 | 270 |
| CXXIV | 4-CH₃-piperazinylNH | 2,5-diMe-3-thienyl | 437 | 250 |
| CXXV | MorpholinylNH | i-propyl | 354 | 256 |
| | | | (M − H) | |
| CXXVI | MorpholinylNH | 4-CO₂Me-piperidinyl | 455 | 216 |
| CXXVII | MorpholinylNH | 5-Me-2-thienyl | 410 | 261 |
| CXXVIII | MorpholinylNH | 5-Cl-3-thienyl | 430 | 259 |
| CXXIX | MorpholinylNH | 2,5-diMe-3-thienyl | 424 | >280 |
| CXXX | MorpholinylNH | 5-CO₂Et-2-thienyl | 468 | 258 |
| CXXXI | MorpholinylNH | 5-CO₂H-2-thienyl | 440 | 273 |
| CXXXII | MorpholinylNH | 5-CONHBn-2-thienyl | 529 | 275 |
| CXXXIII | MorpholinylNH | 5-CONH(4-Me-piperazinyl)-2-thienyl | 537 | 190 |
| CXXXIV | MorpholinylNH | 5-CONHCH₂CH₂(1-Me-2-pyrrolidinyl)-2-thienyl | 550 | 235 |
| CXXXV | MorpholinylNH | 5-CONHNMe₂-2-thienyl | 482 | 201 |
| CXXXVI | MorpholinylNH | 5-CONHCH₂CH₂NMe₂-2-thienyl | 510 | 190 |
| CXXXVII | MorpholinylNH | 5-CONHCH₂CH₂(1-pyrrolidinyl)-2-thienyl | 536 | 224 |
| CXXXVIII | MorpholinylNH | 5-CONHCH₂CH₂(1-morpholinyl)-2-thienyl | 552 | 241 |

TABLE 1-continued

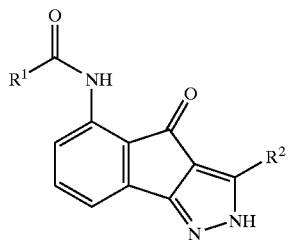

| Example # | R¹ | R² | mass (M+H) | mp (° C.) |
|---|---|---|---|---|
| CXXXIX | MorpholinylNH | 5-CONHmorpholinyl-2-thienyl | 524 | 271 |
| CXL | MorpholinylNH | 5-CONHCH$_2$CH$_2$CH$_2$(1-pyrrolidonyl)-2-thienyl | 564 | 260 |
| CXLI | MorpholinylNH | 5-CONHCH$_2$CH$_2$(3-pyridyl)-2-thienyl | 544 | 203 |
| CXLII | MorpholinylNH | 5-CONHCH$_2$CH$_2$CH$_2$(1-imidazolyl)-2-thienyl | 547 | 263 |
| CXLIII | MorpholinylNH | 5-CONHCH$_2$CH$_2$(2-pyridyl)-2-thienyl | 544 | >280 |
| CXLIV | MorpholinylNH | 5-CONHCH$_2$(3-pyridyl)-2-thienyl | 530 | 239 |
| CXLV | MorpholinylNH | 5-CONHCH$_2$CH$_2$(1-piperidinyl)-2-thienyl | 550 | 228 |
| CXLVI | Methyl | 4-CF$_3$C$_6$H$_4$ | 370 (M − H) | >300 |
| CXLVII | MorpholinylNH | 4-(4-Boc-piperazinyl)C$_6$H$_4$ | 574 | 242 |
| CXLVIII | MorpholinylNH | 4-(piperazinyl)C$_6$H$_4$ | 474 | 263 |
| CXLIX | NH$_2$ | 4-(piperazinyl)C$_6$H$_4$ | 389 | 257 |
| CL | NH$_2$NH | 4-(piperazinyl)C$_6$H$_4$ | 404 | 257 |
| CLI | Me$_2$NCH$_2$ | 4-(piperazinyl)C$_6$H$_4$ | 431 | 243 |
| CLII | morpholinylCH$_2$ | 4-(piperazinyl)C$_6$H$_4$ | 473 | 259 |
| CLIII | 4-Me-piperazinylCH$_2$ | 4-(piperazinyl)C$_6$H$_4$ | 486 | NA |
| CLIV | 4-NH$_2$CH$_2$-piperidinylCH$_2$ | 4-(piperazinyl)C$_6$H$_4$ | 500 | 239 |
| CLV | MorpholinylNH | 4-(4-Me-piperazinyl)C$_6$H$_4$ | 488 | 245 |
| CLVI | MorpholinylNH | 4-(4-Et-piperazinyl)C$_6$H$_4$ | 502 | 245 |
| CLVII | MorpholinylNH | 4-(4-i-Pr-piperazinyl)C$_6$H$_4$ | 516 | 253 |
| CLVIII | C$_6$H$_5$C(O)NHNH | 4-MeOC$_6$H$_4$ | 459 | >300 |
| CLIX | 4-pyridylC(O)NHNH | 4-MeOC$_6$H$_4$ | 455 | 248 |
| CLX | 3-pyridylC(O)NHNH | 4-MeOC$_6$H$_4$ | 455 | 227 |
| CLXI | 3,4-dihydroxy-C$_6$H$_3$C(O)NHNH | 4-MeOC$_6$H$_4$ | 486 | >300 |
| CLXII | 4-hydroxy-C$_6$H$_4$C(O)NHNH | 4-MeOC$_6$H$_4$ | 470 | 283 |
| CLXIII | 3-amino-C$_6$H$_4$C(O)NHNH | 4-MeOC$_6$H$_4$ | 469 | 250 |
| CLXIV | 4-amino-C$_6$H$_4$C(O)NHNH | 4-MeOC$_6$H$_4$ | 469 | 247 |
| CLXV | 2-amino-C$_6$H$_4$C(O)NHNH | 4-MeOC$_6$H$_4$ | 469 | 257 |
| CLXVI | 4-N,N-dimethylamino-C$_6$H$_4$C(O)NHNH | 4-MeOC$_6$H$_4$ | 497 | 259 |
| CLXVII | C$_6$H$_5$CH$_2$C(O)NHNH | 4-MeOC$_6$H$_4$ | 468 | 269 |
| CLXVIII | 2-hydroxy-C$_6$H$_4$C(O)NHNH | 4-MeOC$_6$H$_4$ | 470 | 280 |
| CLXIX | MeOC(O)NHNH | 4-MeOC$_6$H$_4$ | 408 | >300 |

TABLE 2

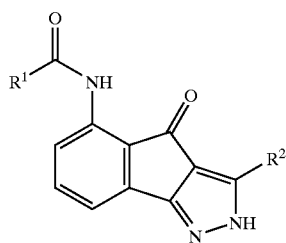

| Example Number | R¹ | R² |
|---|---|---|
| 100 | 2-pyridylmethyl | 4-MeOC$_6$H$_4$ |
| 101 | 2-pyridylmethyl | 3-MeOC$_6$H$_4$ |
| 102 | 2-pyridylmethyl | 4-NH$_2$C$_6$H$_4$ |
| 103 | 2-pyridylmethyl | 3-NH$_2$C$_6$H$_4$ |
| 104 | 2-pyridylmethyl | 2-NH$_2$C$_6$H$_4$ |
| 105 | 2-pyridylmethyl | 4-Me$_2$NC$_6$H$_4$ |
| 106 | 2-pyridylmethyl | 3-Me$_2$NC$_6$H$_4$ |
| 107 | 2-pyridylmethyl | 2-Me$_2$NC$_6$H$_4$ |
| 108 | 2-pyridylmethyl | 4-pyridyl |
| 109 | 2-pyridylmethyl | 3-pyridyl |
| 110 | 2-pyridylmethyl | 2-pyridyl |
| 111 | 2-pyridylmethyl | 2-thiazolyl |
| 112 | 2-pyridylmethyl | 2-pyrazolyl |
| 113 | 2-pyridylmethyl | 5-isoquinolyl |
| 114 | 2-pyridylmethyl | 3,4-methylenedioxyC$_6$H$_3$ |
| 115 | 2-pyridylmethyl | 3,4-ethylenedioxyC$_6$H$_3$ |
| 116 | 2-pyridylmethyl | 2-imidazolyl |
| 117 | 2-pyridylmethyl | 2-oxazolyl |
| 118 | 2-pyridylmethyl | 4-isoxazolyl |
| 119 | 2-pyridylmethyl | 4-HOC$_6$H$_4$ |
| 120 | 2-pyridylmethyl | 3-HOC$_6$H$_4$ |
| 121 | 2-pyridylmethyl | 3,4-diHOC$_6$H$_4$ |
| 122 | 2-pyridylmethyl | 4-NH$_2$CH$_2$C$_6$H$_4$ |
| 123 | 2-pyridylmethyl | 3-NH$_2$CH$_2$C$_6$H$_4$ |
| 124 | 3-pyridylmethyl | 4-MeOC$_6$H$_4$ |
| 125 | 3-pyridylmethyl | 3-MeOC$_6$H$_4$ |
| 126 | 3-pyridylmethyl | 4-NH$_2$C$_6$H$_4$ |
| 127 | 3-pyridylmethyl | 3-NH$_2$C$_6$H$_4$ |
| 128 | 3-pyridylmethyl | 2-NH$_2$C$_6$H$_4$ |
| 129 | 3-pyridylmethyl | 4-Me$_2$NC$_6$H$_4$ |
| 130 | 3-pyridylmethyl | 3-Me$_2$NC$_6$H$_4$ |
| 131 | 3-pyridylmethyl | 2-Me$_2$NC$_6$H$_4$ |
| 132 | 3-pyridylmethyl | 4-pyridyl |
| 133 | 3-pyridylmethyl | 3-pyridyl |
| 134 | 3-pyridylmethyl | 2-pyridyl |
| 135 | 3-pyridylmethyl | 2-thiazolyl |
| 136 | 3-pyridylmethyl | 2-pyrazolyl |
| 137 | 3-pyridylmethyl | 5-isoquinolyl |
| 138 | 3-pyridylmethyl | 3,4-methylenedioxyC$_6$H$_3$ |
| 139 | 3-pyridylmethyl | 3,4-ethylenedioxyC$_6$H$_3$ |
| 140 | 3-pyridylmethyl | 2-imidazolyl |
| 141 | 3-pyridylmethyl | 2-oxazolyl |
| 142 | 3-pyridylmethyl | 4-isoxazolyl |
| 143 | 3-pyridylmethyl | 4-HOC$_6$H$_4$ |
| 144 | 3-pyridylmethyl | 3-HOC$_6$H$_4$ |
| 145 | 3-pyridylmethyl | 3,4-diHOC$_6$H$_4$ |
| 146 | 3-pyridylmethyl | 4-NH$_2$CH$_2$C$_6$H$_4$ |
| 147 | 3-pyridylmethyl | 3-NH$_2$CH$_2$C$_6$H$_4$ |
| 148 | 4-pyridylmethyl | 4-MeOC$_6$H$_4$ |
| 149 | 4-pyridylmethyl | 3-MeOC$_6$H$_4$ |
| 150 | 4-pyridylmethyl | 4-NH$_2$C$_6$H$_4$ |
| 151 | 4-pyridylmethyl | 3-NH$_2$C$_6$H$_4$ |
| 152 | 4-pyridylmethyl | 2-NH$_2$C$_6$H$_4$ |
| 153 | 4-pyridylmethyl | 4-Me$_2$NC$_6$H$_4$ |
| 154 | 4-pyridylmethyl | 3-Me$_2$NC$_6$H$_4$ |
| 155 | 4-pyridylmethyl | 2-Me$_2$NC$_6$H$_4$ |
| 156 | 4-pyridylmethyl | 4-pyridyl |
| 157 | 4-pyridylmethyl | 3-pyridyl |
| 158 | 4-pyridylmethyl | 2-pyridyl |
| 159 | 4-pyridylmethyl | 2-thiazolyl |
| 160 | 4-pyridylmethyl | 2-pyrazolyl |
| 161 | 4-pyridylmethyl | 5-isoquinolyl |
| 162 | 4-pyridylmethyl | 3,4-methylenedioxyC$_6$H$_3$ |

TABLE 2-continued

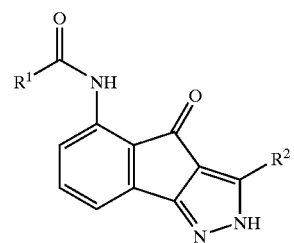

| Example Number | R¹ | R² |
|---|---|---|
| 163 | 4-pyridylmethyl | 3,4-ethylenedioxyC$_6$H$_3$ |
| 164 | 4-pyridylmethyl | 2-imidazolyl |
| 165 | 4-pyridylmethyl | 2-oxazolyl |
| 166 | 4-pyridylmethyl | 4-isoxazolyl |
| 167 | 4-pyridylmethyl | 4-HOC$_6$H$_4$ |
| 168 | 4-pyridylmethyl | 3-HOC$_6$H$_4$ |
| 169 | 4-pyridylmethyl | 3,4-diHOC$_6$H$_4$ |
| 170 | 4-pyridylmethyl | 4-NH$_2$CH$_2$C$_6$H$_4$ |
| 171 | 4-pyridylmethyl | 3-NH$_2$CH$_2$C$_6$H$_4$ |
| 172 | 2-NH$_2$C$_6$H$_4$CH$_2$ | 4-MeOC$_6$H$_4$ |
| 173 | 2-NH$_2$C$_6$H$_4$CH$_2$ | 3-MeOC$_6$H$_4$ |
| 174 | 2-NH$_2$C$_6$H$_4$CH$_2$ | 4-NH$_2$C$_6$H$_4$ |
| 175 | 2-NH$_2$C$_6$H$_4$CH$_2$ | 3-NH$_2$C$_6$H$_4$ |
| 176 | 2-NH$_2$C$_6$H$_4$CH$_2$ | 2-NH$_2$C$_6$H$_4$ |
| 177 | 2-NH$_2$C$_6$H$_4$CH$_2$ | 4-Me$_2$NC$_6$H$_4$ |
| 178 | 2-NH$_2$C$_6$H$_4$CH$_2$ | 3-Me$_2$NC$_6$H$_4$ |
| 179 | 2-NH$_2$C$_6$H$_4$CH$_2$ | 2-Me$_2$NC$_6$H$_4$ |
| 180 | 2-NH$_2$C$_6$H$_4$CH$_2$ | 4-pyridyl |
| 181 | 2-NH$_2$C$_6$H$_4$CH$_2$ | 3-pyridyl |
| 182 | 2-NH$_2$C$_6$H$_4$CH$_2$ | 2-pyridyl |
| 183 | 2-NH$_2$C$_6$H$_4$CH$_2$ | 2-thiazolyl |
| 184 | 2-NH$_2$C$_6$H$_4$CH$_2$ | 2-pyrazolyl |
| 185 | 2-NH$_2$C$_6$H$_4$CH$_2$ | 5-isoquinolyl |
| 186 | 2-NH$_2$C$_6$H$_4$CH$_2$ | 3,4-methylenedioxyC$_6$H$_3$ |
| 187 | 2-NH$_2$C$_6$H$_4$CH$_2$ | 3,4-ethylenedioxyC$_6$H$_3$ |
| 188 | 2-NH$_2$C$_6$H$_4$CH$_2$ | 2-imidazolyl |
| 189 | 2-NH$_2$C$_6$H$_4$CH$_2$ | 2-oxazolyl |
| 190 | 2-NH$_2$C$_6$H$_4$CH$_2$ | 4-isoxazolyl |
| 191 | 2-NH$_2$C$_6$H$_4$CH$_2$ | 4-HOC$_6$H$_4$ |
| 192 | 2-NH$_2$C$_6$H$_4$CH$_2$ | 3-HOC$_6$H$_4$ |
| 193 | 2-NH$_2$C$_6$H$_4$CH$_2$ | 3,4-diHOC$_6$H$_4$ |
| 194 | 2-NH$_2$C$_6$H$_4$CH$_2$ | 4-NH$_2$CH$_2$C$_6$H$_4$ |
| 195 | 2-NH$_2$C$_6$H$_4$CH$_2$ | 3-NH$_2$CH$_2$C$_6$H$_4$ |
| 196 | 3-NH$_2$C$_6$H$_4$CH$_2$ | 3-MeOC$_6$H$_4$ |
| 197 | 3-NH$_2$C$_6$H$_4$CH$_2$ | 4-NH$_2$C$_6$H$_4$ |
| 198 | 3-NH$_2$C$_6$H$_4$CH$_2$ | 3-NH$_2$C$_6$H$_4$ |
| 199 | 3-NH$_2$C$_6$H$_4$CH$_2$ | 2-NH$_2$C$_6$H$_4$ |
| 200 | 3-NH$_2$C$_6$H$_4$CH$_2$ | 4-Me$_2$NC$_6$H$_4$ |
| 201 | 3-NH$_2$C$_6$H$_4$CH$_2$ | 3-Me$_2$NC$_6$H$_4$ |
| 202 | 3-NH$_2$C$_6$H$_4$CH$_2$ | 2-Me$_2$NC$_6$H$_4$ |
| 203 | 3-NH$_2$C$_6$H$_4$CH$_2$ | 4-pyridyl |
| 204 | 3-NH$_2$C$_6$H$_4$CH$_2$ | 3-pyridyl |
| 205 | 3-NH$_2$C$_6$H$_4$CH$_2$ | 2-pyridyl |
| 206 | 3-NH$_2$C$_6$H$_4$CH$_2$ | 2-thiazolyl |
| 207 | 3-NH$_2$C$_6$H$_4$CH$_2$ | 2-pyrazolyl |
| 208 | 3-NH$_2$C$_6$H$_4$CH$_2$ | 5-isoquinolyl |
| 209 | 3-NH$_2$C$_6$H$_4$CH$_2$ | 3,4-methylenedioxyC$_6$H$_3$ |
| 210 | 3-NH$_2$C$_6$H$_4$CH$_2$ | 3,4-ethylenedioxyC$_6$H$_3$ |
| 211 | 3-NH$_2$C$_6$H$_4$CH$_2$ | 2-imidazolyl |
| 212 | 3-NH$_2$C$_6$H$_4$CH$_2$ | 2-oxazolyl |
| 213 | 3-NH$_2$C$_6$H$_4$CH$_2$ | 4-isoxazolyl |
| 214 | 3-NH$_2$C$_6$H$_4$CH$_2$ | 4-HOC$_6$H$_4$ |
| 215 | 3-NH$_2$C$_6$H$_4$CH$_2$ | 3-HOC$_6$H$_4$ |
| 216 | 3-NH$_2$C$_6$H$_4$CH$_2$ | 3,4-diHOC$_6$H$_4$ |
| 217 | 3-NH$_2$C$_6$H$_4$CH$_2$ | 4-NH$_2$CH$_2$C$_6$H$_4$ |
| 218 | 3-NH$_2$C$_6$H$_4$CH$_2$ | 3-NH$_2$CH$_2$C$_6$H$_4$ |
| 219 | 4-NH$_2$C$_6$H$_4$CH$_2$ | 3-MeOC$_6$H$_4$ |
| 220 | 4-NH$_2$C$_6$H$_4$CH$_2$ | 4-NH$_2$C$_6$H$_4$ |
| 221 | 4-NH$_2$C$_6$H$_4$CH$_2$ | 3-NH$_2$C$_6$H$_4$ |
| 222 | 4-NH$_2$C$_6$H$_4$CH$_2$ | 2-NH$_2$C$_6$H$_4$ |
| 223 | 4-NH$_2$C$_6$H$_4$CH$_2$ | 4-Me$_2$NC$_6$H$_4$ |
| 224 | 4-NH$_2$C$_6$H$_4$CH$_2$ | 3-Me$_2$NC$_6$H$_4$ |
| 225 | 4-NH$_2$C$_6$H$_4$CH$_2$ | 2-Me$_2$NC$_6$H$_4$ |

TABLE 2-continued

R¹–C(=O)–NH– attached to indeno-pyrazolone with R² substituent

| Example Number | R¹ | R² |
|---|---|---|
| 226 | 4-NH$_2$C$_6$H$_4$CH$_2$ | 4-pyridyl |
| 227 | 4-NH$_2$C$_6$H$_4$CH$_2$ | 3-pyridyl |
| 228 | 4-NH$_2$C$_6$H$_4$CH$_2$ | 2-pyridyl |
| 229 | 4-NH$_2$C$_6$H$_4$CH$_2$ | 2-thiazolyl |
| 230 | 4-NH$_2$C$_6$H$_4$CH$_2$ | 2-pyrazolyl |
| 231 | 4-NH$_2$C$_6$H$_4$CH$_2$ | 5-isoquinolyl |
| 232 | 4-NH$_2$C$_6$H$_4$CH$_2$ | 3,4-methylenedioxyC$_6$H$_3$ |
| 233 | 4-NH$_2$C$_6$H$_4$CH$_2$ | 3,4-ethylenedioxyC$_6$H$_3$ |
| 234 | 4-NH$_2$C$_6$H$_4$CH$_2$ | 2-imidazolyl |
| 235 | 4-NH$_2$C$_6$H$_4$CH$_2$ | 2-oxazolyl |
| 236 | 4-NH$_2$C$_6$H$_4$CH$_2$ | 4-isoxazolyl |
| 237 | 4-NH$_2$C$_6$H$_4$CH$_2$ | 4-HOC$_6$H$_4$ |
| 238 | 4-NH$_2$C$_6$H$_4$CH$_2$ | 3-HOC$_6$H$_4$ |
| 239 | 4-NH$_2$C$_6$H$_4$CH$_2$ | 3,4-diHOC$_6$H$_4$ |
| 240 | 4-NH$_2$C$_6$H$_4$CH$_2$ | 4-NH$_2$CH$_2$C$_6$H$_4$ |
| 241 | 4-NH$_2$C$_6$H$_4$CH$_2$ | 3-NH$_2$CH$_2$C$_6$H$_4$ |
| 242 | 2-MeOC$_6$H$_4$CH$_2$ | 3-MeOC$_6$H$_4$ |
| 243 | 2-MeOC$_6$H$_4$CH$_2$ | 4-NH$_2$C$_6$H$_4$ |
| 244 | 2-MeOC$_6$H$_4$CH$_2$ | 3-NH$_2$C$_6$H$_4$ |
| 245 | 2-MeOC$_6$H$_4$CH$_2$ | 2-NH$_2$C$_6$H$_4$ |
| 246 | 2-MeOC$_6$H$_4$CH$_2$ | 4-Me$_2$NC$_6$H$_4$ |
| 247 | 2-MeOC$_6$H$_4$CH$_2$ | 3-Me$_2$NC$_6$H$_4$ |
| 248 | 2-MeOC$_6$H$_4$CH$_2$ | 2-Me$_2$NC$_6$H$_4$ |
| 249 | 2-MeOC$_6$H$_4$CH$_2$ | 4-pyridyl |
| 250 | 2-MeOC$_6$H$_4$CH$_2$ | 3-pyridyl |
| 251 | 2-MeOC$_6$H$_4$CH$_2$ | 2-pyridyl |
| 252 | 2-MeOC$_6$H$_4$CH$_2$ | 2-thiazolyl |
| 253 | 2-MeOC$_6$H$_4$CH$_2$ | 2-pyrazolyl |
| 254 | 2-MeOC$_6$H$_4$CH$_2$ | 5-isoquinolyl |
| 255 | 2-MeOC$_6$H$_4$CH$_2$ | 3,4-methylenedioxyC$_6$H$_3$ |
| 256 | 2-MeOC$_6$H$_4$CH$_2$ | 3,4-ethylenedioxyC$_6$H$_3$ |
| 257 | 2-MeOC$_6$H$_4$CH$_2$ | 2-imidazolyl |
| 258 | 2-MeOC$_6$H$_4$CH$_2$ | 2-oxazolyl |
| 259 | 2-MeOC$_6$H$_4$CH$_2$ | 4-isoxazolyl |
| 260 | 2-MeOC$_6$H$_4$CH$_2$ | 4-HOC$_6$H$_4$ |
| 261 | 2-MeOC$_6$H$_4$CH$_2$ | 3-HOC$_6$H$_4$ |
| 262 | 2-MeOC$_6$H$_4$CH$_2$ | 3,4-diHOC$_6$H$_4$ |
| 263 | 2-MeOC$_6$H$_4$CH$_2$ | 4-NH$_2$CH$_2$C$_6$H$_4$ |
| 264 | 2-MeOC$_6$H$_4$CH$_2$ | 3-NH$_2$CH$_2$C$_6$H$_4$ |
| 265 | 3-MeOC$_6$H$_4$CH$_2$ | 3-MeOC$_6$H$_4$ |
| 266 | 3-MeOC$_6$H$_4$CH$_2$ | 4-NH$_2$C$_6$H$_4$ |
| 267 | 3-MeOC$_6$H$_4$CH$_2$ | 3-NH$_2$C$_6$H$_4$ |
| 268 | 3-MeOC$_6$H$_4$CH$_2$ | 2-NH$_2$C$_6$H$_4$ |
| 269 | 3-MeOC$_6$H$_4$CH$_2$ | 4-Me$_2$NC$_6$H$_4$ |
| 270 | 3-MeOC$_6$H$_4$CH$_2$ | 3-Me$_2$NC$_6$H$_4$ |
| 271 | 3-MeOC$_6$H$_4$CH$_2$ | 2-Me$_2$NC$_6$H$_4$ |
| 272 | 3-MeOC$_6$H$_4$CH$_2$ | 4-pyridyl |
| 273 | 3-MeOC$_6$H$_4$CH$_2$ | 3-pyridyl |
| 274 | 3-MeOC$_6$H$_4$CH$_2$ | 2-pyridyl |
| 275 | 3-MeOC$_6$H$_4$CH$_2$ | 2-thiazolyl |
| 276 | 3-MeOC$_6$H$_4$CH$_2$ | 2-pyrazolyl |
| 277 | 3-MeOC$_6$H$_4$CH$_2$ | 5-isoquinolyl |
| 278 | 3-MeOC$_6$H$_4$CH$_2$ | 3,4-methylenedioxyC$_6$H$_3$ |
| 279 | 3-MeOC$_6$H$_4$CH$_2$ | 3,4-ethylenedioxyC$_6$H$_3$ |
| 280 | 3-MeOC$_6$H$_4$CH$_2$ | 2-imidazolyl |
| 281 | 3-MeOC$_6$H$_4$CH$_2$ | 2-oxazolyl |
| 282 | 3-MeOC$_6$H$_4$CH$_2$ | 4-isoxazolyl |
| 283 | 3-MeOC$_6$H$_4$CH$_2$ | 4-HOC$_6$H$_4$ |
| 284 | 3-MeOC$_6$H$_4$CH$_2$ | 3-HOC$_6$H$_4$ |
| 285 | 3-MeOC$_6$H$_4$CH$_2$ | 3,4-diHOC$_6$H$_4$ |
| 286 | 3-MeOC$_6$H$_4$CH$_2$ | 4-NH$_2$CH$_2$C$_6$H$_4$ |
| 287 | 3-MeOC$_6$H$_4$CH$_2$ | 3-NH$_2$CH$_2$C$_6$H$_4$ |
| 288 | 4-MeOC$_6$H$_4$CH$_2$ | 3-MeOC$_6$H$_4$ |
| 289 | 4-MeOC$_6$H$_4$CH$_2$ | 4-NH$_2$C$_6$H$_4$ |
| 290 | 4-MeOC$_6$H$_4$CH$_2$ | 3-NH$_2$C$_6$H$_4$ |
| 291 | 4-MeOC$_6$H$_4$CH$_2$ | 2-NH$_2$C$_6$H$_4$ |
| 292 | 4-MeOC$_6$H$_4$CH$_2$ | 4-Me$_2$NC$_6$H$_4$ |
| 293 | 4-MeOC$_6$H$_4$CH$_2$ | 3-Me$_2$NC$_6$H$_4$ |
| 294 | 4-MeOC$_6$H$_4$CH$_2$ | 2-Me$_2$NC$_6$H$_4$ |
| 295 | 4-MeOC$_6$H$_4$CH$_2$ | 4-pyridyl |
| 296 | 4-MeOC$_6$H$_4$CH$_2$ | 3-pyridyl |
| 297 | 4-MeOC$_6$H$_4$CH$_2$ | 2-pyridyl |
| 298 | 4-MeOC$_6$H$_4$CH$_2$ | 2-thiazolyl |
| 299 | 4-MeOC$_6$H$_4$CH$_2$ | 2-pyrazolyl |
| 300 | 4-MeOC$_6$H$_4$CH$_2$ | 5-isoquinolyl |
| 301 | 4-MeOC$_6$H$_4$CH$_2$ | 3,4-methylenedioxyC$_6$H$_3$ |
| 302 | 4-MeOC$_6$H$_4$CH$_2$ | 3,4-ethylenedioxyC$_6$H$_3$ |
| 303 | 4-MeOC$_6$H$_4$CH$_2$ | 2-imidazolyl |
| 304 | 4-MeOC$_6$H$_4$CH$_2$ | 2-oxazolyl |
| 305 | 4-MeOC$_6$H$_4$CH$_2$ | 4-isoxazolyl |
| 306 | 4-MeOC$_6$H$_4$CH$_2$ | 4-HOC$_6$H$_4$ |
| 307 | 4-MeOC$_6$H$_4$CH$_2$ | 3-HOC$_6$H$_4$ |
| 308 | 4-MeOC$_6$H$_4$CH$_2$ | 3,4-diHOC$_6$H$_4$ |
| 309 | 4-MeOC$_6$H$_4$CH$_2$ | 4-NH$_2$CH$_2$C$_6$H$_4$ |
| 310 | 4-MeOC$_6$H$_4$CH$_2$ | 3-NH$_2$CH$_2$C$_6$H$_4$ |
| 311 | 2-HOC$_6$H$_4$CH$_2$ | 4-MeOC$_6$H$_4$ |
| 312 | 2-HOC$_6$H$_4$CH$_2$ | 3-MeOC$_6$H$_4$ |
| 313 | 2-HOC$_6$H$_4$CH$_2$ | 4-NH$_2$C$_6$H$_4$ |
| 314 | 2-HOC$_6$H$_4$CH$_2$ | 3-NH$_2$C$_6$H$_4$ |
| 315 | 2-HOC$_6$H$_4$CH$_2$ | 2-NH$_2$C$_6$H$_4$ |
| 316 | 2-HOC$_6$H$_4$CH$_2$ | 4-Me$_2$NC$_6$H$_4$ |
| 317 | 2-HOC$_6$H$_4$CH$_2$ | 3-Me$_2$NC$_6$H$_4$ |
| 318 | 2-HOC$_6$H$_4$CH$_2$ | 2-Me$_2$NC$_6$H$_4$ |
| 319 | 2-HOC$_6$H$_4$CH$_2$ | 4-pyridyl |
| 320 | 2-HOC$_6$H$_4$CH$_2$ | 3-pyridyl |
| 321 | 2-HOC$_6$H$_4$CH$_2$ | 2-pyridyl |
| 322 | 2-HOC$_6$H$_4$CH$_2$ | 2-thiazolyl |
| 323 | 2-HOC$_6$H$_4$CH$_2$ | 2-pyrazolyl |
| 324 | 2-HOC$_6$H$_4$CH$_2$ | 5-isoquinolyl |
| 325 | 2-HOC$_6$H$_4$CH$_2$ | 3,4-methylenedioxyC$_6$H$_3$ |
| 326 | 2-HOC$_6$H$_4$CH$_2$ | 3,4-ethylenedioxyC$_6$H$_3$ |
| 327 | 2-HOC$_6$H$_4$CH$_2$ | 2-imidazolyl |
| 328 | 2-HOC$_6$H$_4$CH$_2$ | 2-oxazolyl |
| 329 | 2-HOC$_6$H$_4$CH$_2$ | 4-isoxazolyl |
| 330 | 2-HOC$_6$H$_4$CH$_2$ | 4-HOC$_6$H$_4$ |
| 331 | 2-HOC$_6$H$_4$CH$_2$ | 3-HOC$_6$H$_4$ |
| 332 | 2-HOC$_6$H$_4$CH$_2$ | 3,4-diHOC$_6$H$_4$ |
| 333 | 2-HOC$_6$H$_4$CH$_2$ | 4-NH$_2$CH$_2$C$_6$H$_4$ |
| 334 | 2-HOC$_6$H$_4$CH$_2$ | 3-NH$_2$CH$_2$C$_6$H$_4$ |
| 335 | 3-HOC$_6$H$_4$CH$_2$ | 4-MeOC$_6$H$_4$ |
| 336 | 3-HOC$_6$H$_4$CH$_2$ | 3-MeOC$_6$H$_4$ |
| 337 | 3-HOC$_6$H$_4$CH$_2$ | 4-NH$_2$C$_6$H$_4$ |
| 338 | 3-HOC$_6$H$_4$CH$_2$ | 3-NH$_2$C$_6$H$_4$ |
| 339 | 3-HOC$_6$H$_4$CH$_2$ | 2-NH$_2$C$_6$H$_4$ |
| 340 | 3-HOC$_6$H$_4$CH$_2$ | 4-Me$_2$NC$_6$H$_4$ |
| 341 | 3-HOC$_6$H$_4$CH$_2$ | 3-Me$_2$NC$_6$H$_4$ |
| 342 | 3-HOC$_6$H$_4$CH$_2$ | 2-Me$_2$NC$_6$H$_4$ |
| 343 | 3-HOC$_6$H$_4$CH$_2$ | 4-pyridyl |
| 344 | 3-HOC$_6$H$_4$CH$_2$ | 3-pyridyl |
| 345 | 3-HOC$_6$H$_4$CH$_2$ | 2-pyridyl |
| 346 | 3-HOC$_6$H$_4$CH$_2$ | 2-thiazolyl |
| 347 | 3-HOC$_6$H$_4$CH$_2$ | 2-pyrazolyl |
| 348 | 3-HOC$_6$H$_4$CH$_2$ | 5-isoquinolyl |
| 349 | 3-HOC$_6$H$_4$CH$_2$ | 3,4-methylenedioxyC$_6$H$_3$ |
| 350 | 3-HOC$_6$H$_4$CH$_2$ | 3,4-ethylenedioxyC$_6$H$_3$ |
| 351 | 3-HOC$_6$H$_4$CH$_2$ | 2-imidazolyl |

TABLE 2-continued

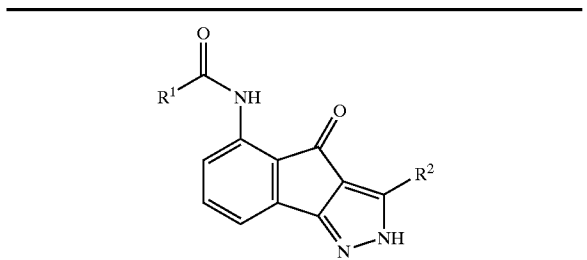

| Example Number | R¹ | R² |
|---|---|---|
| 352 | 3-HOC$_6$H$_4$CH$_2$ | 2-oxazolyl |
| 353 | 3-HOC$_6$H$_4$CH$_2$ | 4-isoxazolyl |
| 354 | 3-HOC$_6$H$_4$CH$_2$ | 4-HOC$_6$H$_4$ |
| 355 | 3-HOC$_6$H$_4$CH$_2$ | 3-HOC$_6$H$_4$ |
| 356 | 3-HOC$_6$H$_4$CH$_2$ | 3,4-diHOC$_6$H$_4$ |
| 357 | 3-HOC$_6$H$_4$CH$_2$ | 4-NH$_2$CH$_2$C$_6$H$_4$ |
| 358 | 3-HOC$_6$H$_4$CH$_2$ | 3-NH$_2$CH$_2$C$_6$H$_4$ |
| 359 | 4-HOC$_6$H$_4$CH$_2$ | 4-MeOC$_6$H$_4$ |
| 360 | 4-HOC$_6$H$_4$CH$_2$ | 3-MeOC$_6$H$_4$ |
| 361 | 4-HOC$_6$H$_4$CH$_2$ | 4-NH$_2$C$_6$H$_4$ |
| 362 | 4-HOC$_6$H$_4$CH$_2$ | 3-NH$_2$C$_6$H$_4$ |
| 363 | 4-HOC$_6$H$_4$CH$_2$ | 2-NH$_2$C$_6$H$_4$ |
| 364 | 4-HOC$_6$H$_4$CH$_2$ | 4-Me$_2$NC$_6$H$_4$ |
| 365 | 4-HOC$_6$H$_4$CH$_2$ | 3-Me$_2$NC$_6$H$_4$ |
| 366 | 4-HOC$_6$H$_4$CH$_2$ | 2-Me$_2$NC$_6$H$_4$ |
| 367 | 4-HOC$_6$H$_4$CH$_2$ | 4-pyridyl |
| 368 | 4-HOC$_6$H$_4$CH$_2$ | 3-pyridyl |
| 369 | 4-HOC$_6$H$_4$CH$_2$ | 2-pyridyl |
| 370 | 4-HOC$_6$H$_4$CH$_2$ | 2-thiazolyl |
| 371 | 4-HOC$_6$H$_4$CH$_2$ | 2-pyrazolyl |
| 372 | 4-HOC$_6$H$_4$CH$_2$ | 5-isoquinolyl |
| 373 | 4-HOC$_6$H$_4$CH$_2$ | 3,4-methylenedioxyC$_6$H$_3$ |
| 374 | 4-HOC$_6$H$_4$CH$_2$ | 3,4-ethylenedioxyC$_6$H$_3$ |
| 375 | 4-HOC$_6$H$_4$CH$_2$ | 2-imidazolyl |
| 376 | 4-HOC$_6$H$_4$CH$_2$ | 2-oxazolyl |
| 377 | 4-HOC$_6$H$_4$CH$_2$ | 4-isoxazolyl |
| 378 | 4-HOC$_6$H$_4$CH$_2$ | 4-HOC$_6$H$_4$ |
| 379 | 4-HOC$_6$H$_4$CH$_2$ | 3-HOC$_6$H$_4$ |
| 380 | 4-HOC$_6$H$_4$CH$_2$ | 3,4-diHOC$_6$H$_4$ |
| 381 | 4-HOC$_6$H$_4$CH$_2$ | 4-NH$_2$CH$_2$C$_6$H$_4$ |
| 382 | 4-HOC$_6$H$_4$CH$_2$ | 3-NH$_2$CH$_2$C$_6$H$_4$ |
| 383 | 4-ClC$_6$H$_4$CH$_2$ | 3-MeOC$_6$H$_4$ |
| 384 | 4-ClC$_6$H$_4$CH$_2$ | 4-NH$_2$C$_6$H$_4$ |
| 385 | 4-ClC$_6$H$_4$CH$_2$ | 3-NH$_2$C$_6$H$_4$ |
| 386 | 4-ClC$_6$H$_4$CH$_2$ | 2-NH$_2$C$_6$H$_4$ |
| 387 | 4-ClC$_6$H$_4$CH$_2$ | 4-Me$_2$NC$_6$H$_4$ |
| 388 | 4-ClC$_6$H$_4$CH$_2$ | 3-Me$_2$NC$_6$H$_4$ |
| 389 | 4-ClC$_6$H$_4$CH$_2$ | 2-Me$_2$NC$_6$H$_4$ |
| 390 | 4-ClC$_6$H$_4$CH$_2$ | 4-pyridyl |
| 391 | 4-ClC$_6$H$_4$CH$_2$ | 3-pyridyl |
| 392 | 4-ClC$_6$H$_4$CH$_2$ | 2-pyridyl |
| 393 | 4-ClC$_6$H$_4$CH$_2$ | 2-thiazolyl |
| 394 | 4-ClC$_6$H$_4$CH$_2$ | 2-pyrazolyl |
| 395 | 4-ClC$_6$H$_4$CH$_2$ | 5-isoquinolyl |
| 396 | 4-ClC$_6$H$_4$CH$_2$ | 3,4-methylenedioxyC$_6$H$_3$ |
| 397 | 4-ClC$_6$H$_4$CH$_2$ | 3,4-ethylenedioxyC$_6$H$_3$ |
| 398 | 4-ClC$_6$H$_4$CH$_2$ | 2-imidazolyl |
| 399 | 4-ClC$_6$H$_4$CH$_2$ | 2-oxazolyl |
| 400 | 4-ClC$_6$H$_4$CH$_2$ | 4-isoxazolyl |
| 401 | 4-ClC$_6$H$_4$CH$_2$ | 4-HOC$_6$H$_4$ |
| 402 | 4-ClC$_6$H$_4$CH$_2$ | 3-HOC$_6$H$_4$ |
| 403 | 4-ClC$_6$H$_4$CH$_2$ | 3,4-diHOC$_6$H$_4$ |
| 404 | 4-ClC$_6$H$_4$CH$_2$ | 4-NH$_2$CH$_2$C$_6$H$_4$ |
| 405 | 4-ClC$_6$H$_4$CH$_2$ | 3-NH$_2$CH$_2$C$_6$H$_4$ |
| 406 | 2-NH$_2$CH$_2$C$_6$H$_4$CH$_2$ | 4-MeOC$_6$H$_4$ |
| 407 | 2-NH$_2$CH$_2$C$_6$H$_4$CH$_2$ | 3-MeOC$_6$H$_4$ |
| 408 | 2-NH$_2$CH$_2$C$_6$H$_4$CH$_2$ | 4-NH$_2$C$_6$H$_4$ |
| 409 | 2-NH$_2$CH$_2$C$_6$H$_4$CH$_2$ | 3-NH$_2$C$_6$H$_4$ |
| 410 | 2-NH$_2$CH$_2$C$_6$H$_4$CH$_2$ | 2-NH$_2$C$_6$H$_4$ |
| 411 | 2-NH$_2$CH$_2$C$_6$H$_4$CH$_2$ | 4-Me$_2$NC$_6$H$_4$ |
| 412 | 2-NH$_2$CH$_2$C$_6$H$_4$CH$_2$ | 3-Me$_2$NC$_6$H$_4$ |
| 413 | 2-NH$_2$CH$_2$C$_6$H$_4$CH$_2$ | 2-Me$_2$NC$_6$H$_4$ |
| 414 | 2-NH$_2$CH$_2$C$_6$H$_4$CH$_2$ | 4-pyridyl |

TABLE 2-continued

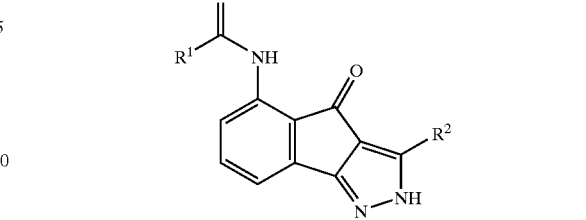

| Example Number | R¹ | R² |
|---|---|---|
| 415 | 2-NH$_2$CH$_2$C$_6$H$_4$CH$_2$ | 3-pyridyl |
| 416 | 2-NH$_2$CH$_2$C$_6$H$_4$CH$_2$ | 2-pyridyl |
| 417 | 2-NH$_2$CH$_2$C$_6$H$_4$CH$_2$ | 2-thiazolyl |
| 418 | 2-NH$_2$CH$_2$C$_6$H$_4$CH$_2$ | 2-pyrazolyl |
| 419 | 2-NH$_2$CH$_2$C$_6$H$_4$CH$_2$ | 5-isoquinolyl |
| 420 | 2-NH$_2$CH$_2$C$_6$H$_4$CH$_2$ | 3,4-methylenedioxyC$_6$H$_3$ |
| 421 | 2-NH$_2$CH$_2$C$_6$H$_4$CH$_2$ | 3,4-ethylenedioxyC$_6$H$_3$ |
| 422 | 2-NH$_2$CH$_2$C$_6$H$_4$CH$_2$ | 2-imidazolyl |
| 423 | 2-NH$_2$CH$_2$C$_6$H$_4$CH$_2$ | 2-oxazolyl |
| 424 | 2-NH$_2$CH$_2$C$_6$H$_4$CH$_2$ | 4-isoxazolyl |
| 425 | 2-NH$_2$CH$_2$C$_6$H$_4$CH$_2$ | 4-HOC$_6$H$_4$ |
| 426 | 2-NH$_2$CH$_2$C$_6$H$_4$CH$_2$ | 3-HOC$_6$H$_4$ |
| 427 | 2-NH$_2$CH$_2$C$_6$H$_4$CH$_2$ | 3,4-diHOC$_6$H$_4$ |
| 428 | 2-NH$_2$CH$_2$C$_6$H$_4$CH$_2$ | 4-NH$_2$CH$_2$C$_6$H$_4$ |
| 429 | 2-NH$_2$CH$_2$C$_6$H$_4$CH$_2$ | 3-NH$_2$CH$_2$C$_6$H$_4$ |
| 430 | 3-NH$_2$CH$_2$C$_6$H$_4$CH$_2$ | 4-MeOC$_6$H$_4$ |
| 431 | 3-NH$_2$CH$_2$C$_6$H$_4$CH$_2$ | 3-MeOC$_6$H$_4$ |
| 432 | 3-NH$_2$CH$_2$C$_6$H$_4$CH$_2$ | 4-NH$_2$C$_6$H$_4$ |
| 433 | 3-NH$_2$CH$_2$C$_6$H$_4$CH$_2$ | 3-NH$_2$C$_6$H$_4$ |
| 434 | 3-NH$_2$CH$_2$C$_6$H$_4$CH$_2$ | 2-NH$_2$C$_6$H$_4$ |
| 435 | 3-NH$_2$CH$_2$C$_6$H$_4$CH$_2$ | 4-Me$_2$NC$_6$H$_4$ |
| 436 | 3-NH$_2$CH$_2$C$_6$H$_4$CH$_2$ | 3-Me$_2$NC$_6$H$_4$ |
| 437 | 3-NH$_2$CH$_2$C$_6$H$_4$CH$_2$ | 2-Me$_2$NC$_6$H$_4$ |
| 438 | 3-NH$_2$CH$_2$C$_6$H$_4$CH$_2$ | 4-pyridyl |
| 439 | 3-NH$_2$CH$_2$C$_6$H$_4$CH$_2$ | 3-pyridyl |
| 440 | 3-NH$_2$CH$_2$C$_6$H$_4$CH$_2$ | 2-pyridyl |
| 441 | 3-NH$_2$CH$_2$C$_6$H$_4$CH$_2$ | 2-thiazolyl |
| 442 | 3-NH$_2$CH$_2$C$_6$H$_4$CH$_2$ | 2-pyrazolyl |
| 443 | 3-NH$_2$CH$_2$C$_6$H$_4$CH$_2$ | 5-isoquinolyl |
| 444 | 3-NH$_2$CH$_2$C$_6$H$_4$CH$_2$ | 3,4-methylenedioxyC$_6$H$_3$ |
| 445 | 3-NH$_2$CH$_2$C$_6$H$_4$CH$_2$ | 3,4-ethylenedioxyC$_6$H$_3$ |
| 446 | 3-NH$_2$CH$_2$C$_6$H$_4$CH$_2$ | 2-imidazolyl |
| 447 | 3-NH$_2$CH$_2$C$_6$H$_4$CH$_2$ | 2-oxazolyl |
| 448 | 3-NH$_2$CH$_2$C$_6$H$_4$CH$_2$ | 4-isoxazolyl |
| 449 | 3-NH$_2$CH$_2$C$_6$H$_4$CH$_2$ | 4-HOC$_6$H$_4$ |
| 450 | 3-NH$_2$CH$_2$C$_6$H$_4$CH$_2$ | 3-HOC$_6$H$_4$ |
| 451 | 3-NH$_2$CH$_2$C$_6$H$_4$CH$_2$ | 3,4-diHOC$_6$H$_4$ |
| 452 | 3-NH$_2$CH$_2$C$_6$H$_4$CH$_2$ | 4-NH$_2$CH$_2$C$_6$H$_4$ |
| 453 | 3-NH$_2$CH$_2$C$_6$H$_4$CH$_2$ | 3-NH$_2$CH$_2$C$_6$H$_4$ |
| 454 | 4-NH$_2$CH$_2$C$_6$H$_4$CH$_2$ | 4-MeOC$_6$H$_4$ |
| 455 | 4-NH$_2$CH$_2$C$_6$H$_4$CH$_2$ | 3-MeOC$_6$H$_4$ |
| 456 | 4-NH$_2$CH$_2$C$_6$H$_4$CH$_2$ | 4-NH$_2$C$_6$H$_4$ |
| 457 | 4-NH$_2$CH$_2$C$_6$H$_4$CH$_2$ | 3-NH$_2$C$_6$H$_4$ |
| 458 | 4-NH$_2$CH$_2$C$_6$H$_4$CH$_2$ | 2-NH$_2$C$_6$H$_4$ |
| 459 | 4-NH$_2$CH$_2$C$_6$H$_4$CH$_2$ | 4-Me$_2$NC$_6$H$_4$ |
| 460 | 4-NH$_2$CH$_2$C$_6$H$_4$CH$_2$ | 3-Me$_2$NC$_6$H$_4$ |
| 461 | 4-NH$_2$CH$_2$C$_6$H$_4$CH$_2$ | 2-Me$_2$NC$_6$H$_4$ |
| 462 | 4-NH$_2$CH$_2$C$_6$H$_4$CH$_2$ | 4-pyridyl |
| 463 | 4-NH$_2$CH$_2$C$_6$H$_4$CH$_2$ | 3-pyridyl |
| 464 | 4-NH$_2$CH$_2$C$_6$H$_4$CH$_2$ | 2-pyridyl |
| 465 | 4-NH$_2$CH$_2$C$_6$H$_4$CH$_2$ | 2-thiazolyl |
| 466 | 4-NH$_2$CH$_2$C$_6$H$_4$CH$_2$ | 2-pyrazolyl |
| 467 | 4-NH$_2$CH$_2$C$_6$H$_4$CH$_2$ | 5-isoquinolyl |
| 468 | 4-NH$_2$CH$_2$C$_6$H$_4$CH$_2$ | 3,4-methylenedioxyC$_6$H$_3$ |
| 469 | 4-NH$_2$CH$_2$C$_6$H$_4$CH$_2$ | 3,4-ethylenedioxyC$_6$H$_3$ |
| 470 | 4-NH$_2$CH$_2$C$_6$H$_4$CH$_2$ | 2-imidazolyl |
| 471 | 4-NH$_2$CH$_2$C$_6$H$_4$CH$_2$ | 2-oxazolyl |
| 472 | 4-NH$_2$CH$_2$C$_6$H$_4$CH$_2$ | 4-isoxazolyl |
| 473 | 4-NH$_2$CH$_2$C$_6$H$_4$CH$_2$ | 4-HOC$_6$H$_4$ |
| 474 | 4-NH$_2$CH$_2$C$_6$H$_4$CH$_2$ | 3-HOC$_6$H$_4$ |
| 475 | 4-NH$_2$CH$_2$C$_6$H$_4$CH$_2$ | 3,4-diHOC$_6$H$_4$ |
| 476 | 4-NH$_2$CH$_2$C$_6$H$_4$CH$_2$ | 4-NH$_2$CH$_2$C$_6$H$_4$ |
| 477 | 4-NH$_2$CH$_2$C$_6$H$_4$CH$_2$ | 3-NH$_2$CH$_2$C$_6$H$_4$ |

TABLE 2-continued

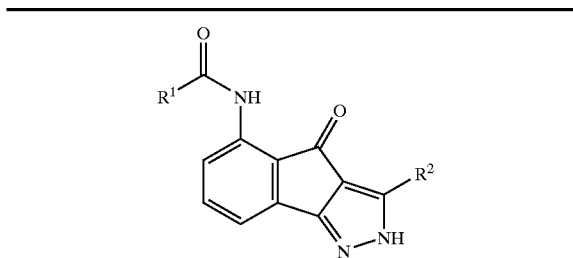

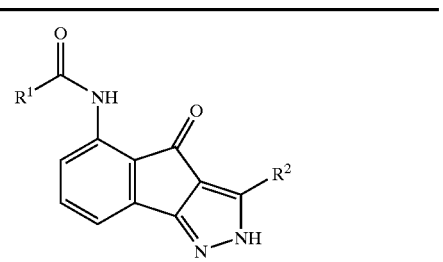

| Example Number | R¹ | R² |
|---|---|---|
| 478 | 2-Me₂NCH₂C₆H₄CH₂ | 4-MeOC₆H₄ |
| 479 | 2-Me₂NCH₂C₆H₄CH₂ | 3-MeOC₆H₄ |
| 480 | 2-Me₂NCH₂C₆H₄CH₂ | 4-NH₂C₆H₄ |
| 481 | 2-Me₂NCH₂C₆H₄CH₂ | 3-NH₂C₆H₄ |
| 482 | 2-Me₂NCH₂C₆H₄CH₂ | 2-NH₂C₆H₄ |
| 483 | 2-Me₂NCH₂C₆H₄CH₂ | 4-Me₂NC₆H₄ |
| 484 | 2-Me₂NCH₂C₆H₄CH₂ | 3-Me₂NC₆H₄ |
| 485 | 2-Me₂NCH₂C₆H₄CH₂ | 2-Me₂NC₆H₄ |
| 486 | 2-Me₂NCH₂C₆H₄CH₂ | 4-pyridyl |
| 487 | 2-Me₂NCH₂C₆H₄CH₂ | 3-pyridyl |
| 488 | 2-Me₂NCH₂C₆H₄CH₂ | 2-pyridyl |
| 489 | 2-Me₂NCH₂C₆H₄CH₂ | 2-thiazolyl |
| 490 | 2-Me₂NCH₂C₆H₄CH₂ | 2-pyrazolyl |
| 491 | 2-Me₂NCH₂C₆H₄CH₂ | 5-isoquinolyl |
| 492 | 2-Me₂NCH₂C₆H₄CH₂ | 3,4-methylenedioxyC₆H₃ |
| 493 | 2-Me₂NCH₂C₆H₄CH₂ | 3,4-ethylenedioxyC₆H₃ |
| 494 | 2-Me₂NCH₂C₆H₄CH₂ | 2-imidazolyl |
| 495 | 2-Me₂NCH₂C₆H₄CH₂ | 2-oxazolyl |
| 496 | 2-Me₂NCH₂C₆H₄CH₂ | 4-isoxazolyl |
| 497 | 2-Me₂NCH₂C₆H₄CH₂ | 4-HOC₆H₄ |
| 498 | 2-Me₂NCH₂C₆H₄CH₂ | 3-HOC₆H₄ |
| 499 | 2-Me₂NCH₂C₆H₄CH₂ | 3,4-diHOC₆H₄ |
| 500 | 2-Me₂NCH₂C₆H₄CH₂ | 4-NH₂CH₂C₆H₄ |
| 501 | 2-Me₂NCH₂C₆H₄CH₂ | 3-NH₂CH₂C₆H₄ |
| 502 | 3-Me₂NCH₂C₆H₄CH₂ | 4-MeOC₆H₄ |
| 503 | 3-Me₂NCH₂C₆H₄CH₂ | 3-MeOC₆H₄ |
| 504 | 3-Me₂NCH₂C₆H₄CH₂ | 4-NH₂C₆H₄ |
| 505 | 3-Me₂NCH₂C₆H₄CH₂ | 3-NH₂C₆H₄ |
| 506 | 3-Me₂NCH₂C₆H₄CH₂ | 2-NH₂C₆H₄ |
| 507 | 3-Me₂NCH₂C₆H₄CH₂ | 4-Me₂NC₆H₄ |
| 508 | 3-Me₂NCH₂C₆H₄CH₂ | 3-Me₂NC₆H₄ |
| 509 | 3-Me₂NCH₂C₆H₄CH₂ | 2-Me₂NC₆H₄ |
| 510 | 3-Me₂NCH₂C₆H₄CH₂ | 4-pyridyl |
| 511 | 3-Me₂NCH₂C₆H₄CH₂ | 3-pyridyl |
| 512 | 3-Me₂NCH₂C₆H₄CH₂ | 2-pyridyl |
| 513 | 3-Me₂NCH₂C₆H₄CH₂ | 2-thiazolyl |
| 514 | 3-Me₂NCH₂C₆H₄CH₂ | 2-pyrazolyl |
| 515 | 3-Me₂NCH₂C₆H₄CH₂ | 5-isoquinolyl |
| 516 | 3-Me₂NCH₂C₆H₄CH₂ | 3,4-methylenedioxyC₆H₃ |
| 517 | 3-Me₂NCH₂C₆H₄CH₂ | 3,4-ethylenedioxyC₆H₃ |
| 518 | 3-Me₂NCH₂C₆H₄CH₂ | 2-imidazolyl |
| 519 | 3-Me₂NCH₂C₆H₄CH₂ | 2-oxazolyl |
| 520 | 3-Me₂NCH₂C₆H₄CH₂ | 4-isoxazolyl |
| 521 | 3-Me₂NCH₂C₆H₄CH₂ | 4-HOC₆H₄ |
| 522 | 3-Me₂NCH₂C₆H₄CH₂ | 3-HOC₆H₄ |
| 523 | 3-Me₂NCH₂C₆H₄CH₂ | 3,4-diHOC₆H₄ |
| 524 | 3-Me₂NCH₂C₆H₄CH₂ | 4-NH₂CH₂C₆H₄ |
| 525 | 3-Me₂NCH₂C₆H₄CH₂ | 3-NH₂CH₂C₆H₄ |
| 526 | 4-Me₂NCH₂C₆H₄CH₂ | 4-MeOC₆H₄ |
| 527 | 4-Me₂NCH₂C₆H₄CH₂ | 3-MeOC₆H₄ |
| 528 | 4-Me₂NCH₂C₆H₄CH₂ | 4-NH₂C₆H₄ |
| 529 | 4-Me₂NCH₂C₆H₄CH₂ | 3-NH₂C₆H₄ |
| 530 | 4-Me₂NCH₂C₆H₄CH₂ | 2-NH₂C₆H₄ |
| 531 | 4-Me₂NCH₂C₆H₄CH₂ | 4-Me₂NC₆H₄ |
| 532 | 4-Me₂NCH₂C₆H₄CH₂ | 3-Me₂NC₆H₄ |
| 533 | 4-Me₂NCH₂C₆H₄CH₂ | 2-Me₂NC₆H₄ |
| 534 | 4-Me₂NCH₂C₆H₄CH₂ | 4-pyridyl |
| 535 | 4-Me₂NCH₂C₆H₄CH₂ | 3-pyridyl |
| 536 | 4-Me₂NCH₂C₆H₄CH₂ | 2-pyridyl |
| 537 | 4-Me₂NCH₂C₆H₄CH₂ | 2-thiazolyl |
| 538 | 4-Me₂NCH₂C₆H₄CH₂ | 2-pyrazolyl |
| 539 | 4-Me₂NCH₂C₆H₄CH₂ | 5-isoquinolyl |
| 540 | 4-Me₂NCH₂C₆H₄CH₂ | 3,4-methylenedioxyC₆H₃ |
| 541 | 4-Me₂NCH₂C₆H₄CH₂ | 3,4-ethylenedioxyC₆H₃ |
| 542 | 4-Me₂NCH₂C₆H₄CH₂ | 2-imidazolyl |
| 543 | 4-Me₂NCH₂C₆H₄CH₂ | 2-oxazolyl |
| 545 | 4-Me₂NCH₂C₆H₄CH₂ | 4-isoxazolyl |
| 546 | 4-Me₂NCH₂C₆H₄CH₂ | 4-HOC₆H₄ |
| 547 | 4-Me₂NCH₂C₆H₄CH₂ | 3-HOC₆H₄ |
| 548 | 4-Me₂NCH₂C₆H₄CH₂ | 3,4-diHOC₆H₄ |
| 549 | 4-Me₂NCH₂C₆H₄CH₂ | 4-NH₂CH₂C₆H₄ |
| 550 | 4-Me₂NCH₂C₆H₄CH₂ | 3-NH₂CH₂C₆H₄ |
| 551 | H | 3-MeOC₆H₄ |
| 552 | H | 4-NH₂C₆H₄ |
| 553 | H | 3-NH₂C₆H₄ |
| 554 | H | 2-NH₂C₆H₄ |
| 555 | H | 4-Me₂NC₆H₄ |
| 556 | H | 3-Me₂NC₆H₄ |
| 557 | H | 2-Me₂NC₆H₄ |
| 558 | H | 3-pyridyl |
| 559 | H | 2-pyridyl |
| 560 | H | 2-thiazolyl |
| 561 | H | 2-pyrazolyl |
| 562 | H | 5-isoquinolyl |
| 563 | H | 3,4-methylenedioxyC₆H₃ |
| 564 | H | 3,4-ethylenedioxyC₆H₃ |
| 565 | H | 2-imidazolyl |
| 566 | H | 2-oxazolyl |
| 567 | H | 4-isoxazolyl |
| 568 | H | 4-HOC₆H₄ |
| 569 | H | 3-HOC₆H₄ |
| 570 | H | 3,4-diHOC₆H₄ |
| 571 | H | 4-NH₂CH₂C₆H₄ |
| 572 | H | 3-NH₂CH₂C₆H₄ |
| 573 | Me | 3-MeOC₆H₄ |
| 574 | Me | 4-NH₂C₆H₄ |
| 575 | Me | 3-NH₂C₆H₄ |
| 576 | Me | 2-NH₂C₆H₄ |
| 577 | Me | 4-Me₂NC₆H₄ |
| 578 | Me | 3-Me₂NC₆H₄ |
| 579 | Me | 2-Me₂NC₆H₄ |
| 580 | Me | 3-pyridyl |
| 581 | Me | 2-pyridyl |
| 582 | Me | 2-thiazolyl |
| 583 | Me | 2-pyrazolyl |
| 584 | Me | 5-isoquinolyl |
| 585 | Me | 3,4-ethylenedioxyC₆H₃ |
| 586 | Me | 2-imidazolyl |
| 587 | Me | 2-oxazolyl |
| 588 | Me | 4-isoxazolyl |
| 589 | Me | 3-HOC₆H₄ |
| 590 | Me | 3,4-diHOC₆H₄ |
| 591 | Me | 4-NH₂CH₂C₆H₄ |
| 592 | Me | 3-NH₂CH₂C₆H₄ |
| 593 | Et | 3-MeOC₆H₄ |
| 594 | Et | 4-NH₂C₆H₄ |
| 595 | Et | 3-NH₂C₆H₄ |
| 596 | Et | 2-NH₂C₆H₄ |
| 597 | Et | 4-Me₂NC₆H₄ |
| 598 | Et | 3-Me₂NC₆H₄ |
| 599 | Et | 2-Me₂NC₆H₄ |
| 600 | Et | 4-pyridyl |
| 601 | Et | 3-pyridyl |
| 602 | Et | 2-pyridyl |
| 603 | Et | 2-thiazolyl |
| 604 | Et | 2-pyrazolyl |

TABLE 2-continued

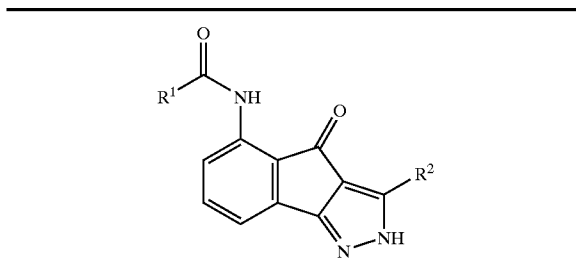

| Example Number | R¹ | R² |
|---|---|---|
| 605 | Et | 5-isoquinolyl |
| 606 | Et | 3,4-methylenedioxyC₆H₃ |
| 607 | Et | 3,4-ethylenedioxyC₆H₃ |
| 608 | Et | 2-imidazolyl |
| 609 | Et | 2-oxazolyl |
| 610 | Et | 4-isoxazolyl |
| 611 | Et | 4-HOC₆H₄ |
| 612 | Et | 3-HOC₆H₄ |
| 613 | Et | 3,4-diHOC₆H₄ |
| 614 | Et | 4-NH₂CH₂C₆H₄ |
| 615 | Et | 3-NH₂CH₂C₆H₄ |
| 616 | Me₂NCH₂ | 3-MeOC₆H₄ |
| 617 | Me₂NCH₂ | 4-NH₂C₆H₄ |
| 618 | Me₂NCH₂ | 3-NH₂C₆H₄ |
| 619 | Me₂NCH₂ | 2-NH₂C₆H₄ |
| 620 | Me₂NCH₂ | 4-Me₂NC₆H₄ |
| 621 | Me₂NCH₂ | 3-Me₂NC₆H₄ |
| 622 | Me₂NCH₂ | 2-Me₂NC₆H₄ |
| 623 | Me₂NCH₂ | 4-pyridyl |
| 624 | Me₂NCH₂ | 3-pyridyl |
| 625 | Me₂NCH₂ | 2-pyridyl |
| 626 | Me₂NCH₂ | 2-thiazolyl |
| 627 | Me₂NCH₂ | 2-pyrazolyl |
| 628 | Me₂NCH₂ | 5-isoquinolyl |
| 629 | Me₂NCH₂ | 3,4-methylenedioxyC₆H₃ |
| 630 | Me₂NCH₂ | 3,4-ethylenedioxyC₆H₃ |
| 631 | Me₂NCH₂ | 2-imidazolyl |
| 632 | Me₂NCH₂ | 2-oxazolyl |
| 633 | Me₂NCH₂ | 4-isoxazolyl |
| 634 | Me₂NCH₂ | 4-HOC₆H₄ |
| 635 | Me₂NCH₂ | 3-HOC₆H₄ |
| 636 | Me₂NCH₂ | 3,4-diHOC₆H₄ |
| 637 | Me₂NCH₂ | 4-NH₂CH₂C₆H₄ |
| 638 | Me₂NCH₂ | 3-NH₂CH₂C₆H₄ |
| 639 | EtNHCH₂ | 3-MeOC₆H₄ |
| 640 | EtNHCH₂ | 4-NH₂C₆H₄ |
| 641 | EtNHCH₂ | 3-NH₂C₆H₄ |
| 642 | EtNHCH₂ | 2-NH₂C₆H₄ |
| 643 | EtNHCH₂ | 4-Me₂NC₆H₄ |
| 644 | EtNHCH₂ | 3-Me₂NC₆H₄ |
| 645 | EtNHCH₂ | 2-Me₂NC₆H₄ |
| 646 | EtNHCH₂ | 4-pyridyl |
| 647 | EtNHCH₂ | 3-pyridyl |
| 648 | EtNHCH₂ | 2-pyridyl |
| 649 | EtNHCH₂ | 2-thiazolyl |
| 650 | EtNHCH₂ | 2-pyrazolyl |
| 651 | EtNHCH₂ | 5-isoquinolyl |
| 652 | EtNHCH₂ | 3,4-methylenedioxyC₆H₃ |
| 653 | EtNHCH₂ | 3,4-ethylenedioxyC₆H₃ |
| 654 | EtNHCH₂ | 2-imidazolyl |
| 655 | EtNHCH₂ | 2-oxazolyl |
| 656 | EtNHCH₂ | 4-isoxazolyl |
| 657 | EtNHCH₂ | 4-HOC₆H₄ |
| 658 | EtNHCH₂ | 3-HOC₆H₄ |
| 659 | EtNHCH₂ | 3,4-diHOC₆H₄ |
| 660 | EtNHCH₂ | 4-NH₂CH₂C₆H₄ |
| 661 | EtNHCH₂ | 3-NH₂CH₂C₆H₄ |
| 662 | HOCH₂CH₂NHCH₂ | 3-MeOC₆H₄ |
| 663 | HOCH₂CH₂NHCH₂ | 4-NH₂C₆H₄ |
| 664 | HOCH₂CH₂NHCH₂ | 3-NH₂C₆H₄ |
| 665 | HOCH₂CH₂NHCH₂ | 2-NH₂C₆H₄ |
| 666 | HOCH₂CH₂NHCH₂ | 4-Me₂NC₆H₄ |
| 667 | HOCH₂CH₂NHCH₂ | 3-Me₂NC₆H₄ |
| 668 | HOCH₂CH₂NHCH₂ | 2-Me₂NC₆H₄ |
| 669 | HOCH₂CH₂NHCH₂ | 4-pyridyl |
| 670 | HOCH₂CH₂NHCH₂ | 3-pyridyl |
| 671 | HOCH₂CH₂NHCH₂ | 2-pyridyl |
| 672 | HOCH₂CH₂NHCH₂ | 2-thiazolyl |
| 673 | HOCH₂CH₂NHCH₂ | 2-pyrazolyl |
| 674 | HOCH₂CH₂NHCH₂ | 5-isoquinolyl |
| 675 | HOCH₂CH₂NHCH₂ | 3,4-methylenedioxyC₆H₃ |
| 676 | HOCH₂CH₂NHCH₂ | 3,4-ethylenedioxyC₆H₃ |
| 677 | HOCH₂CH₂NHCH₂ | 2-imidazolyl |
| 678 | HOCH₂CH₂NHCH₂ | 2-oxazolyl |
| 679 | HOCH₂CH₂NHCH₂ | 4-isoxazolyl |
| 680 | HOCH₂CH₂NHCH₂ | 4-HOC₆H₄ |
| 681 | HOCH₂CH₂NHCH₂ | 3-HOC₆H₄ |
| 682 | HOCH₂CH₂NHCH₂ | 3,4-diHOC₆H₄ |
| 683 | HOCH₂CH₂NHCH₂ | 4-NH₂CH₂C₆H₄ |
| 684 | HOCH₂CH₂NHCH₂ | 3-NH₂CH₂C₆H₄ |
| 685 | H₂NCH₂CH₂NHCH₂ | 4-MeOC₆H₄ |
| 686 | H₂NCH₂CH₂NHCH₂ | 3-MeOC₆H₄ |
| 687 | H₂NCH₂CH₂NHCH₂ | 4-NH₂C₆H₄ |
| 688 | H₂NCH₂CH₂NHCH₂ | 3-NH₂C₆H₄ |
| 689 | H₂NCH₂CH₂NHCH₂ | 2-NH₂C₆H₄ |
| 690 | H₂NCH₂CH₂NHCH₂ | 4-Me₂NC₆H₄ |
| 691 | H₂NCH₂CH₂NHCH₂ | 3-Me₂NC₆H₄ |
| 692 | H₂NCH₂CH₂NHCH₂ | 2-Me₂NC₆H₄ |
| 693 | H₂NCH₂CH₂NHCH₂ | 4-pyridyl |
| 694 | H₂NCH₂CH₂NHCH₂ | 3-pyridyl |
| 695 | H₂NCH₂CH₂NHCH₂ | 2-pyridyl |
| 696 | H₂NCH₂CH₂NHCH₂ | 2-thiazolyl |
| 697 | H₂NCH₂CH₂NHCH₂ | 2-pyrazolyl |
| 698 | H₂NCH₂CH₂NHCH₂ | 5-isoquinolyl |
| 699 | H₂NCH₂CH₂NHCH₂ | 3,4-methylenedioxyC₆H₃ |
| 700 | H₂NCH₂CH₂NHCH₂ | 3,4-ethylenedioxyC₆H₃ |
| 701 | H₂NCH₂CH₂NHCH₂ | 2-imidazolyl |
| 702 | H₂NCH₂CH₂NHCH₂ | 2-oxazolyl |
| 703 | H₂NCH₂CH₂NHCH₂ | 4-isoxazolyl |
| 704 | H₂NCH₂CH₂NHCH₂ | 4-HOC₆H₄ |
| 705 | H₂NCH₂CH₂NHCH₂ | 3-HOC₆H₄ |
| 706 | H₂NCH₂CH₂NHCH₂ | 3,4-diHOC₆H₄ |
| 707 | H₂NCH₂CH₂NHCH₂ | 4-NH₂CH₂C₆H₄ |
| 708 | H₂NCH₂CH₂NHCH₂ | 3-NH₂CH₂C₆H₄ |
| 709 | Me₂NCH₂CH₂NHCH₂ | 4-MeOC₆H₄ |
| 710 | Me₂NCH₂CH₂NHCH₂ | 3-MeOC₆H₄ |
| 711 | Me₂NCH₂CH₂NHCH₂ | 4-NH₂C₆H₄ |
| 712 | Me₂NCH₂CH₂NHCH₂ | 3-NH₂C₆H₄ |
| 713 | Me₂NCH₂CH₂NHCH₂ | 2-NH₂C₆H₄ |
| 714 | Me₂NCH₂CH₂NHCH₂ | 4-Me₂NC₆H₄ |
| 715 | Me₂NCH₂CH₂NHCH₂ | 3-Me₂NC₆H₄ |
| 716 | Me₂NCH₂CH₂NHCH₂ | 2-Me₂NC₆H₄ |
| 717 | Me₂NCH₂CH₂NHCH₂ | 4-pyridyl |
| 718 | Me₂NCH₂CH₂NHCH₂ | 3-pyridyl |
| 719 | Me₂NCH₂CH₂NHCH₂ | 2-pyridyl |
| 720 | Me₂NCH₂CH₂NHCH₂ | 2-thiazolyl |
| 721 | Me₂NCH₂CH₂NHCH₂ | 2-pyrazolyl |
| 722 | Me₂NCH₂CH₂NHCH₂ | 5-isoquinolyl |
| 723 | Me₂NCH₂CH₂NHCH₂ | 3,4-methylenedioxyC₆H₃ |
| 724 | Me₂NCH₂CH₂NHCH₂ | 3,4-ethylenedioxyC₆H₃ |
| 725 | Me₂NCH₂CH₂NHCH₂ | 2-imidazolyl |
| 726 | Me₂NCH₂CH₂NHCH₂ | 2-oxazolyl |
| 727 | Me₂NCH₂CH₂NHCH₂ | 4-isoxazolyl |
| 728 | Me₂NCH₂CH₂NHCH₂ | 4-HOC₆H₄ |
| 729 | Me₂NCH₂CH₂NHCH₂ | 3-HOC₆H₄ |
| 730 | Me₂NCH₂CH₂NHCH₂ | 3,4-diHOC₆H₄ |

TABLE 2-continued

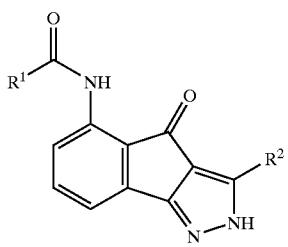

| Example Number | R¹ | R² |
|---|---|---|
| 731 | Me₂NCH₂CH₂NHCH₂ | 4-NH₂CH₂C₆H₄ |
| 732 | Me₂NCH₂CH₂NHCH₂ | 3-NH₂CH₂C₆H₄ |
| 733 | 1-morpholinylmethyl | 3-MeOC₆H₄ |
| 734 | 1-morpholinylmethyl | 4-NH₂C₆H₄ |
| 735 | 1-morpholinylmethyl | 3-NH₂C₆H₄ |
| 736 | 1-morpholinylmethyl | 2-NH₂C₆H₄ |
| 737 | 1-morpholinylmethyl | 4-Me₂NC₆H₄ |
| 738 | 1-morpholinylmethyl | 3-Me₂NC₆H₄ |
| 739 | 1-morpholinylmethyl | 2-Me₂NC₆H₄ |
| 740 | 1-morpholinylmethyl | 4-pyridyl |
| 741 | 1-morpholinylmethyl | 3-pyridyl |
| 742 | 1-morpholinylmethyl | 2-pyridyl |
| 743 | 1-morpholinylmethyl | 2-thiazolyl |
| 744 | 1-morpholinylmethyl | 2-pyrazolyl |
| 745 | 1-morpholinylmethyl | 5-isoquinolyl |
| 746 | 1-morpholinylmethyl | 3,4-methylenedioxyC₆H₃ |
| 747 | 1-morpholinylmethyl | 3,4-ethylenedioxyC₆H₃ |
| 748 | 1-morpholinylmethyl | 2-imidazolyl |
| 749 | 1-morpholinylmethyl | 2-oxazolyl |
| 750 | 1-morpholinylmethyl | 4-isoxazolyl |
| 751 | 1-morpholinylmethyl | 4-HOC₆H₄ |
| 752 | 1-morpholinylmethyl | 3-HOC₆H₄ |
| 753 | 1-morpholinylmethyl | 3,4-diHOC₆H₄ |
| 754 | 1-morpholinylmethyl | 4-NH₂CH₂C₆H₄ |
| 755 | 1-morpholinylmethyl | 3-NH₂CH₂C₆H₄ |
| 756 | 1-thiomorpholinylmethyl | 3-MeOC₆H₄ |
| 757 | 1-thiomorpholinylmethyl | 4-NH₂C₆H₄ |
| 758 | 1-thiomorpholinylmethyl | 3-NH₂C₆H₄ |
| 759 | 1-thiomorpholinylmethyl | 2-NH₂C₆H₄ |
| 760 | 1-thiomorpholinylmethyl | 4-Me₂NC₆H₄ |
| 761 | 1-thiomorpholinylmethyl | 3-Me₂NC₆H₄ |
| 762 | 1-thiomorpholinylmethyl | 2-Me₂NC₆H₄ |
| 763 | 1-thiomorpholinylmethyl | 4-pyridyl |
| 764 | 1-thiomorpholinylmethyl | 3-pyridyl |
| 765 | 1-thiomorpholinylmethyl | 2-pyridyl |
| 766 | 1-thiomorpholinylmethyl | 2-thiazolyl |
| 767 | 1-thiomorpholinylmethyl | 2-pyrazolyl |
| 768 | 1-thiomorpholinylmethyl | 5-isoquinolyl |
| 769 | 1-thiomorpholinylmethyl | 3,4-methylenedioxyC₆H₃ |
| 770 | 1-thiomorpholinylmethyl | 3,4-ethylenedioxyC₆H₃ |
| 771 | 1-thiomorpholinylmethyl | 2-imidazolyl |
| 772 | 1-thiomorpholinylmethyl | 2-oxazolyl |
| 773 | 1-thiomorpholinylmethyl | 4-isoxazolyl |
| 774 | 1-thiomorpholinylmethyl | 4-HOC₆H₄ |
| 775 | 1-thiomorpholinylmethyl | 3-HOC₆H₄ |
| 776 | 1-thiomorpholinylmethyl | 3,4-diHOC₆H₄ |
| 777 | 1-thiomorpholinylmethyl | 4-NH₂CH₂C₆H₄ |
| 778 | 1-thiomorpholinylmethyl | 3-NH₂CH₂C₆H₄ |
| 779 | 1-piperazinylmethyl | 3-MeOC₆H₄ |
| 780 | 1-piperazinylmethyl | 4-NH₂C₆H₄ |
| 781 | 1-piperazinylmethyl | 3-NH₂C₆H₄ |
| 782 | 1-piperazinylmethyl | 2-NH₂C₆H₄ |
| 783 | 1-piperazinylmethyl | 4-Me₂NC₆H₄ |
| 784 | 1-piperazinylmethyl | 3-Me₂NC₆H₄ |
| 785 | 1-piperazinylmethyl | 2-Me₂NC₆H₄ |
| 786 | 1-piperazinylmethyl | 4-pyridyl |
| 787 | 1-piperazinylmethyl | 3-pyridyl |
| 788 | 1-piperazinylmethyl | 2-pyridyl |
| 789 | 1-piperazinylmethyl | 2-thiazolyl |
| 790 | 1-piperazinylmethyl | 2-pyrazolyl |
| 791 | 1-piperazinylmethyl | 5-isoquinolyl |
| 792 | 1-piperazinylmethyl | 3,4-methylenedioxyC₆H₃ |
| 793 | 1-piperazinylmethyl | 3,4-ethylenedioxyC₆H₃ |

TABLE 2-continued

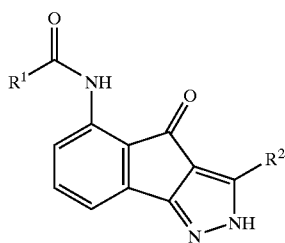

| Example Number | R¹ | R² |
|---|---|---|
| 794 | 1-piperazinylmethyl | 2-imidazolyl |
| 795 | 1-piperazinylmethyl | 2-oxazolyl |
| 796 | 1-piperazinylmethyl | 4-isoxazolyl |
| 797 | 1-piperazinylmethyl | 4-HOC₆H₄ |
| 798 | 1-piperazinylmethyl | 3-HOC₆H₄ |
| 799 | 1-piperazinylmethyl | 3,4-diHOC₆H₄ |
| 800 | 1-piperazinylmethyl | 4-NH₂CH₂C₆H₄ |
| 801 | 1-piperazinylmethyl | 3-NH₂CH₂C₆H₄ |

TABLE 3

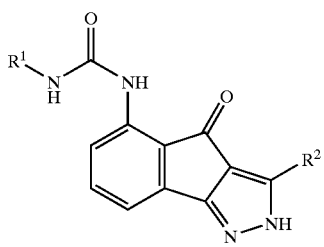

| Example Number | R¹ | R² |
|---|---|---|
| 802 | 2-pyridylmethyl | 4-MeOC₆H₄ |
| 803 | 2-pyridylmethyl | 3-MeOC₆H₄ |
| 804 | 2-pyridylmethyl | 4-NH₂C₆H₄ |
| 805 | 2-pyridylmethyl | 3-NH₂C₆H₄ |
| 806 | 2-pyridylmethyl | 2-NH₂C₆H₄ |
| 807 | 2-pyridylmethyl | 4-Me₂NC₆H₄ |
| 808 | 2-pyridylmethyl | 3-Me₂NC₆H₄ |
| 809 | 2-pyridylmethyl | 2-Me₂NC₆H₄ |
| 810 | 2-pyridylmethyl | 4-pyridyl |
| 811 | 2-pyridylmethyl | 3-pyridyl |
| 812 | 2-pyridylmethyl | 2-pyridyl |
| 813 | 2-pyridylmethyl | 2-thiazolyl |
| 814 | 2-pyridylmethyl | 2-pyrazolyl |
| 815 | 2-pyridylmethyl | 5-isoquinolyl |
| 816 | 2-pyridylmethyl | 3,4-methylenedioxyC₆H₃ |
| 817 | 2-pyridylmethyl | 3,4-ethylenedioxyC₆H₃ |
| 818 | 2-pyridylmethyl | 2-imidazolyl |
| 819 | 2-pyridylmethyl | 2-oxazolyl |
| 820 | 2-pyridylmethyl | 4-isoxazolyl |
| 821 | 2-pyridylmethyl | 4-HOC₆H₄ |
| 822 | 2-pyridylmethyl | 3-HOC₆H₄ |
| 823 | 2-pyridylmethyl | 3,4-diHOC₆H₄ |
| 824 | 2-pyridylmethyl | 4-NH₂CH₂C₆H₄ |
| 825 | 2-pyridylmethyl | 3-NH₂CH₂C₆H₄ |
| 826 | 3-pyridylmethyl | 4-MeOC₆H₄ |
| 827 | 3-pyridylmethyl | 3-MeOC₆H₄ |
| 828 | 3-pyridylmethyl | 4-NH₂C₆H₄ |
| 829 | 3-pyridylmethyl | 3-NH₂C₆H₄ |
| 830 | 3-pyridylmethyl | 2-NH₂C₆H₄ |
| 831 | 3-pyridylmethyl | 4-Me₂NC₆H₄ |
| 832 | 3-pyridylmethyl | 3-Me₂NC₆H₄ |
| 833 | 3-pyridylmethyl | 2-Me₂NC₆H₄ |
| 834 | 3-pyridylmethyl | 4-pyridyl |
| 835 | 3-pyridylmethyl | 3-pyridyl |
| 836 | 3-pyridylmethyl | 2-pyridyl |

TABLE 3-continued

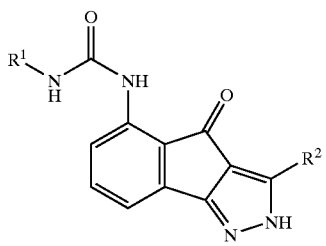

| Example Number | R¹ | R² |
|---|---|---|
| 837 | 3-pyridylmethyl | 2-thiazolyl |
| 838 | 3-pyridylmethyl | 2-pyrazolyl |
| 839 | 3-pyridylmethyl | 5-isoquinolyl |
| 840 | 3-pyridylmethyl | 3,4-methylenedioxyC$_6$H$_3$ |
| 841 | 3-pyridylmethyl | 3,4-ethylenedioxyC$_6$H$_3$ |
| 842 | 3-pyridylmethyl | 2-imidazolyl |
| 843 | 3-pyridylmethyl | 2-oxazolyl |
| 844 | 3-pyridylmethyl | 4-isoxazolyl |
| 845 | 3-pyridylmethyl | 4-HOC$_6$H$_4$ |
| 846 | 3-pyridylmethyl | 3-HOC$_6$H$_4$ |
| 847 | 3-pyridylmethyl | 3,4-diHOC$_6$H$_4$ |
| 848 | 3-pyridylmethyl | 4-NH$_2$CH$_2$C$_6$H$_4$ |
| 849 | 3-pyridylmethyl | 3-NH$_2$CH$_2$C$_6$H$_4$ |
| 850 | 4-pyridylmethyl | 4-MeOC$_6$H$_4$ |
| 851 | 4-pyridylmethyl | 3-MeOC$_6$H$_4$ |
| 852 | 4-pyridylmethyl | 4-NH$_2$C$_6$H$_4$ |
| 853 | 4-pyridylmethyl | 3-NH$_2$C$_6$H$_4$ |
| 854 | 4-pyridylmethyl | 2-NH$_2$C$_6$H$_4$ |
| 855 | 4-pyridylmethyl | 4-Me$_2$NC$_6$H$_4$ |
| 856 | 4-pyridylmethyl | 3-Me$_2$NC$_6$H$_4$ |
| 857 | 4-pyridylmethyl | 2-Me$_2$NC$_6$H$_4$ |
| 858 | 4-pyridylmethyl | 4-pyridyl |
| 859 | 4-pyridylmethyl | 3-pyridyl |
| 860 | 4-pyridylmethyl | 2-pyridyl |
| 861 | 4-pyridylmethyl | 2-thiazolyl |
| 862 | 4-pyridylmethyl | 2-pyrazolyl |
| 863 | 4-pyridylmethyl | 5-isoquinolyl |
| 864 | 4-pyridylmethyl | 3,4-methylenedioxyC$_6$H$_3$ |
| 865 | 4-pyridylmethyl | 3,4-ethylenedioxyC$_6$H$_3$ |
| 866 | 4-pyridylmethyl | 2-imidazolyl |
| 867 | 4-pyridylmethyl | 2-oxazolyl |
| 868 | 4-pyridylmethyl | 4-isoxazolyl |
| 869 | 4-pyridylmethyl | 4-HOC$_6$H$_4$ |
| 870 | 4-pyridylmethyl | 3-HOC$_6$H$_4$ |
| 871 | 4-pyridylmethyl | 3,4-diHOC$_6$H$_4$ |
| 872 | 4-pyridylmethyl | 4-NH$_2$CH$_2$C$_6$H$_4$ |
| 873 | 4-pyridylmethyl | 3-NH$_2$CH$_2$C$_6$H$_4$ |
| 874 | 2-NH$_2$C$_6$H$_4$ | 4-MeOC$_6$H$_4$ |
| 875 | 2-NH$_2$C$_6$H$_4$ | 3-MeOC$_6$H$_4$ |
| 876 | 2-NH$_2$C$_6$H$_4$ | 4-NH$_2$C$_6$H$_4$ |
| 877 | 2-NH$_2$C$_6$H$_4$ | 3-NH$_2$C$_6$H$_4$ |
| 878 | 2-NH$_2$C$_6$H$_4$ | 2-NH$_2$C$_6$H$_4$ |
| 879 | 2-NH$_2$C$_6$H$_4$ | 4-Me$_2$NC$_6$H$_4$ |
| 880 | 2-NH$_2$C$_6$H$_4$ | 3-Me$_2$NC$_6$H$_4$ |
| 881 | 2-NH$_2$C$_6$H$_4$ | 2-Me$_2$NC$_6$H$_4$ |
| 882 | 2-NH$_2$C$_6$H$_4$ | 4-pyridyl |
| 883 | 2-NH$_2$C$_6$H$_4$ | 3-pyridyl |
| 884 | 2-NH$_2$C$_6$H$_4$ | 2-pyridyl |
| 885 | 2-NH$_2$C$_6$H$_4$ | 2-thiazolyl |
| 886 | 2-NH$_2$C$_6$H$_4$ | 2-pyrazolyl |
| 887 | 2-NH$_2$C$_6$H$_4$ | 5-isoquinolyl |
| 888 | 2-NH$_2$C$_6$H$_4$ | 3,4-methylenedioxyC$_6$H$_3$ |
| 889 | 2-NH$_2$C$_6$H$_4$ | 3,4-ethylenedioxyC$_6$H$_3$ |
| 890 | 2-NH$_2$C$_6$H$_4$ | 2-imidazolyl |
| 891 | 2-NH$_2$C$_6$H$_4$ | 2-oxazolyl |
| 892 | 2-NH$_2$C$_6$H$_4$ | 4-isoxazolyl |
| 893 | 2-NH$_2$C$_6$H$_4$ | 4-HOC$_6$H$_4$ |
| 894 | 2-NH$_2$C$_6$H$_4$ | 3-HOC$_6$H$_4$ |
| 895 | 2-NH$_2$C$_6$H$_4$ | 3,4-diHOC$_6$H$_4$ |
| 896 | 2-NH$_2$C$_6$H$_4$ | 4-NH$_2$CH$_2$C$_6$H$_4$ |
| 897 | 2-NH$_2$C$_6$H$_4$ | 3-NH$_2$CH$_2$C$_6$H$_4$ |
| 898 | 3-NH$_2$C$_6$H$_4$ | 4-MeOC$_6$H$_4$ |
| 899 | 3-NH$_2$C$_6$H$_4$ | 3-MeOC$_6$H$_4$ |

TABLE 3-continued

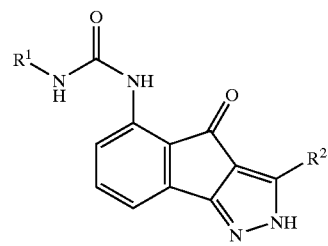

| Example Number | R¹ | R² |
|---|---|---|
| 900 | 3-NH$_2$C$_6$H$_4$ | 4-NH$_2$C$_6$H$_4$ |
| 901 | 3-NH$_2$C$_6$H$_4$ | 3-NH$_2$C$_6$H$_4$ |
| 902 | 3-NH$_2$C$_6$H$_4$ | 2-NH$_2$C$_6$H$_4$ |
| 903 | 3-NH$_2$C$_6$H$_4$ | 4-Me$_2$NC$_6$H$_4$ |
| 904 | 3-NH$_2$C$_6$H$_4$ | 3-Me$_2$NC$_6$H$_4$ |
| 905 | 3-NH$_2$C$_6$H$_4$ | 2-Me$_2$NC$_6$H$_4$ |
| 906 | 3-NH$_2$C$_6$H$_4$ | 4-pyridyl |
| 907 | 3-NH$_2$C$_6$H$_4$ | 3-pyridyl |
| 908 | 3-NH$_2$C$_6$H$_4$ | 2-pyridyl |
| 909 | 3-NH$_2$C$_6$H$_4$ | 2-thiazolyl |
| 910 | 3-NH$_2$C$_6$H$_4$ | 2-pyrazolyl |
| 911 | 3-NH$_2$C$_6$H$_4$ | 5-isoquinolyl |
| 912 | 3-NH$_2$C$_6$H$_4$ | 3,4-methylenedioxyC$_6$H$_3$ |
| 913 | 3-NH$_2$C$_6$H$_4$ | 3,4-ethylenedioxyC$_6$H$_3$ |
| 914 | 3-NH$_2$C$_6$H$_4$ | 2-imidazolyl |
| 915 | 3-NH$_2$C$_6$H$_4$ | 2-oxazolyl |
| 916 | 3-NH$_2$C$_6$H$_4$ | 4-isoxazolyl |
| 917 | 3-NH$_2$C$_6$H$_4$ | 4-HOC$_6$H$_4$ |
| 918 | 3-NH$_2$C$_6$H$_4$ | 3-HOC$_6$H$_4$ |
| 919 | 3-NH$_2$C$_6$H$_4$ | 3,4-diHOC$_6$H$_4$ |
| 920 | 3-NH$_2$C$_6$H$_4$ | 4-NH$_2$CH$_2$C$_6$H$_4$ |
| 921 | 3-NH$_2$C$_6$H$_4$ | 3-NH$_2$CH$_2$C$_6$H$_4$ |
| 922 | 4-NH$_2$C$_6$H$_4$ | 4-MeOC$_6$H$_4$ |
| 923 | 4-NH$_2$C$_6$H$_4$ | 3-MeOC$_6$H$_4$ |
| 924 | 4-NH$_2$C$_6$H$_4$ | 4-NH$_2$C$_6$H$_4$ |
| 925 | 4-NH$_2$C$_6$H$_4$ | 3-NH$_2$C$_6$H$_4$ |
| 926 | 4-NH$_2$C$_6$H$_4$ | 2-NH$_2$C$_6$H$_4$ |
| 927 | 4-NH$_2$C$_6$H$_4$ | 4-Me$_2$NC$_6$H$_4$ |
| 928 | 4-NH$_2$C$_6$H$_4$ | 3-Me$_2$NC$_6$H$_4$ |
| 930 | 4-NH$_2$C$_6$H$_4$ | 2-Me$_2$NC$_6$H$_4$ |
| 931 | 4-NH$_2$C$_6$H$_4$ | 4-pyridyl |
| 932 | 4-NH$_2$C$_6$H$_4$ | 3-pyridyl |
| 933 | 4-NH$_2$C$_6$H$_4$ | 2-pyridyl |
| 934 | 4-NH$_2$C$_6$H$_4$ | 2-thiazolyl |
| 935 | 4-NH$_2$C$_6$H$_4$ | 2-pyrazolyl |
| 936 | 4-NH$_2$C$_6$H$_4$ | 5-isoquinolyl |
| 937 | 4-NH$_2$C$_6$H$_4$ | 3,4-methylenedioxyC$_6$H$_3$ |
| 938 | 4-NH$_2$C$_6$H$_4$ | 3,4-ethylenedioxyC$_6$H$_3$ |
| 939 | 4-NH$_2$C$_6$H$_4$ | 2-imidazolyl |
| 940 | 4-NH$_2$C$_6$H$_4$ | 2-oxazolyl |
| 941 | 4-NH$_2$C$_6$H$_4$ | 4-isoxazolyl |
| 942 | 4-NH$_2$C$_6$H$_4$ | 4-HOC$_6$H$_4$ |
| 943 | 4-NH$_2$C$_6$H$_4$ | 3-HOC$_6$H$_4$ |
| 944 | 4-NH$_2$C$_6$H$_4$ | 3,4-diHOC$_6$H$_4$ |
| 945 | 4-NH$_2$C$_6$H$_4$ | 4-NH$_2$CH$_2$C$_6$H$_4$ |
| 946 | 4-NH$_2$C$_6$H$_4$ | 3-NH$_2$CH$_2$C$_6$H$_4$ |
| 947 | 2-MeOC$_6$H$_4$ | 4-MeOC$_6$H$_4$ |
| 948 | 2-MeOC$_6$H$_4$ | 3-MeOC$_6$H$_4$ |
| 949 | 2-MeOC$_6$H$_4$ | 4-NH$_2$C$_6$H$_4$ |
| 950 | 2-MeOC$_6$H$_4$ | 3-NH$_2$C$_6$H$_4$ |
| 951 | 2-MeOC$_6$H$_4$ | 2-NH$_2$C$_6$H$_4$ |
| 952 | 2-MeOC$_6$H$_4$ | 4-Me$_2$NC$_6$H$_4$ |
| 953 | 2-MeOC$_6$H$_4$ | 3-Me$_2$NC$_6$H$_4$ |
| 954 | 2-MeOC$_6$H$_4$ | 2-Me$_2$NC$_6$H$_4$ |
| 955 | 2-MeOC$_6$H$_4$ | 4-pyridyl |
| 956 | 2-MeOC$_6$H$_4$ | 3-pyridyl |
| 957 | 2-MeOC$_6$H$_4$ | 2-pyridyl |
| 958 | 2-MeOC$_6$H$_4$ | 2-thiazolyl |
| 959 | 2-MeOC$_6$H$_4$ | 2-pyrazolyl |
| 960 | 2-MeOC$_6$H$_4$ | 5-isoquinolyl |
| 961 | 2-MeOC$_6$H$_4$ | 3,4-methylenedioxyC$_6$H$_3$ |
| 962 | 2-MeOC$_6$H$_4$ | 3-4-ethylenedioxyC$_6$H$_3$ |
| 963 | 2-MeOC$_6$H$_4$ | 2-imidazolyl |

TABLE 3-continued

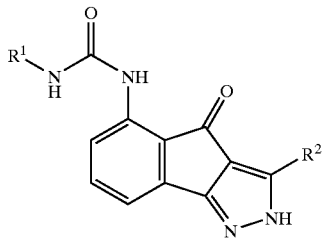

| Example Number | R¹ | R² |
|---|---|---|
| 964 | 2-MeOC$_6$H$_4$ | 2-oxazolyl |
| 965 | 2-MeOC$_6$H$_4$ | 4-isoxazolyl |
| 966 | 2-MeOC$_6$H$_4$ | 4-HOC$_6$H$_4$ |
| 967 | 2-MeOC$_6$H$_4$ | 3-HOC$_6$H$_4$ |
| 968 | 2-MeOC$_6$H$_4$ | 3,4-diHOC$_6$H$_4$ |
| 969 | 2-MeOC$_6$H$_4$ | 4-NH$_2$CH$_2$C$_6$H$_4$ |
| 970 | 2-MeOC$_6$H$_4$ | 3-NH$_2$CH$_2$C$_6$H$_4$ |
| 971 | 3-MeOC$_6$H$_4$ | 4-MeOC$_6$H$_4$ |
| 972 | 3-MeOC$_6$H$_4$ | 3-MeOC$_6$H$_4$ |
| 973 | 3-MeOC$_6$H$_4$ | 4-NH$_2$C$_6$H$_4$ |
| 974 | 3-MeOC$_6$H$_4$ | 3-NH$_2$C$_6$H$_4$ |
| 975 | 3-MeOC$_6$H$_4$ | 2-NH$_2$C$_6$H$_4$ |
| 976 | 3-MeOC$_6$H$_4$ | 4-Me$_2$NC$_6$H$_4$ |
| 977 | 3-MeOC$_6$H$_4$ | 3-Me$_2$NC$_6$H$_4$ |
| 978 | 3-MeOC$_6$H$_4$ | 2-Me$_2$NC$_6$H$_4$ |
| 979 | 3-MeOC$_6$H$_4$ | 4-pyridyl |
| 980 | 3-MeOC$_6$H$_4$ | 3-pyridyl |
| 981 | 3-MeOC$_6$H$_4$ | 2-pyridyl |
| 982 | 3-MeOC$_6$H$_4$ | 2-thiazolyl |
| 983 | 3-MeOC$_6$H$_4$ | 2-pyrazolyl |
| 984 | 3-MeOC$_6$H$_4$ | 5-isoquinolyl |
| 985 | 3-MeOC$_6$H$_4$ | 3,4-methylenedioxyC$_6$H$_3$ |
| 986 | 3-MeOC$_6$H$_4$ | 3,4-ethylenedioxyC$_6$H$_3$ |
| 987 | 3-MeOC$_6$H$_4$ | 2-imidazolyl |
| 988 | 3-MeOC$_6$H$_4$ | 2-oxazolyl |
| 989 | 3-MeOC$_6$H$_4$ | 4-isoxazolyl |
| 990 | 3-MeOC$_6$H$_4$ | 4-HOC$_6$H$_4$ |
| 991 | 3-MeOC$_6$H$_4$ | 3-HOC$_6$H$_4$ |
| 992 | 3-MeOC$_6$H$_4$ | 3,4-diHOC$_6$H$_4$ |
| 993 | 3-MeOC$_6$H$_4$ | 4-NH$_2$CH$_2$C$_6$H$_4$ |
| 994 | 3-MeOC$_6$H$_4$ | 3-NH$_2$CH$_2$C$_6$H$_4$ |
| 995 | 4-MeOC$_6$H$_4$ | 4-MeOC$_6$H$_4$ |
| 996 | 4-MeOC$_6$H$_4$ | 3-MeOC$_6$H$_4$ |
| 997 | 4-MeOC$_6$H$_4$ | 4-NH$_2$C$_6$H$_4$ |
| 998 | 4-MeOC$_6$H$_4$ | 3-NH$_2$C$_6$H$_4$ |
| 999 | 4-MeOC$_6$H$_4$ | 2-NH$_2$C$_6$H$_4$ |
| 1000 | 4-MeOC$_6$H$_4$ | 4-Me$_2$NC$_6$H$_4$ |
| 1001 | 4-MeOC$_6$H$_4$ | 3-Me$_2$NC$_6$H$_4$ |
| 1002 | 4-MeOC$_6$H$_4$ | 2-Me$_2$NC$_6$H$_4$ |
| 1003 | 4-MeOC$_6$H$_4$ | 4-pyridyl |
| 1004 | 4-MeOC$_6$H$_4$ | 3-pyridyl |
| 1005 | 4-MeOC$_6$H$_4$ | 2-pyridyl |
| 1006 | 4-MeOC$_6$H$_4$ | 2-thiazolyl |
| 1007 | 4-MeOC$_6$H$_4$ | 2-pyrazolyl |
| 1008 | 4-MeOC$_6$H$_4$ | 5-isoquinolyl |
| 1009 | 4-MeOC$_6$H$_4$ | 3,4-methylenedioxyC$_6$H$_3$ |
| 1010 | 4-MeOC$_6$H$_4$ | 3,4-ethylenedioxyC$_6$H$_3$ |
| 1011 | 4-MeOC$_6$H$_4$ | 2-imidazolyl |
| 1012 | 4-MeOC$_6$H$_4$ | 2-oxazolyl |
| 1013 | 4-MeOC$_6$H$_4$ | 4-isoxazolyl |
| 1014 | 4-MeOC$_6$H$_4$ | 4-HOC$_6$H$_4$ |
| 1015 | 4-MeOC$_6$H$_4$ | 3-HOC$_6$H$_4$ |
| 1016 | 4-MeOC$_6$H$_4$ | 3,4-diHOC$_6$H$_4$ |
| 1017 | 4-MeOC$_6$H$_4$ | 4-NH$_2$CH$_2$C$_6$H$_4$ |
| 1018 | 4-MeOC$_6$H$_4$ | 3-NH$_2$CH$_2$C$_6$H$_4$ |
| 1019 | 2-HOC$_6$H$_4$ | 4-MeOC$_6$H$_4$ |
| 1020 | 2-HOC$_6$H$_4$ | 3-MeOC$_6$H$_4$ |
| 1021 | 2-HOC$_6$H$_4$ | 4-NH$_2$C$_6$H$_4$ |
| 1022 | 2-HOC$_6$H$_4$ | 3-NH$_2$C$_6$H$_4$ |
| 1023 | 2-HOC$_6$H$_4$ | 2-NH$_2$C$_6$H$_4$ |
| 1024 | 2-HOC$_6$H$_4$ | 4-Me$_2$NC$_6$H$_4$ |
| 1025 | 2-HOC$_6$H$_4$ | 3-Me$_2$NC$_6$H$_4$ |
| 1026 | 2-HOC$_6$H$_4$ | 2-Me$_2$NC$_6$H$_4$ |

TABLE 3-continued

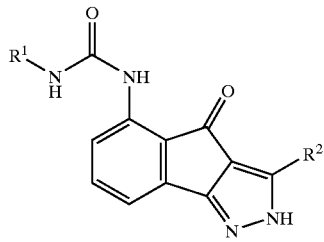

| Example Number | R¹ | R² |
|---|---|---|
| 1027 | 2-HOC$_6$H$_4$ | 4-pyridyl |
| 1028 | 2-HOC$_6$H$_4$ | 3-pyridyl |
| 1029 | 2-HOC$_6$H$_4$ | 2-pyridyl |
| 1030 | 2-HOC$_6$H$_4$ | 2-thiazolyl |
| 1031 | 2-HOC$_6$H$_4$ | 2-pyrazolyl |
| 1032 | 2-HOC$_6$H$_4$ | 5-isoquinolyl |
| 1033 | 2-HOC$_6$H$_4$ | 3,4-methylenedioxyC$_6$H$_3$ |
| 1034 | 2-HOC$_6$H$_4$ | 3,4-ethylenedioxyC$_6$H$_3$ |
| 1035 | 2-HOC$_6$H$_4$ | 2-imidazolyl |
| 1036 | 2-HOC$_6$H$_4$ | 2-oxazolyl |
| 1037 | 2-HOC$_6$H$_4$ | 4-isoxazolyl |
| 1038 | 2-HOC$_6$H$_4$ | 4-HOC$_6$H$_4$ |
| 1039 | 2-HOC$_6$H$_4$ | 3-HOC$_6$H$_4$ |
| 1040 | 2-HOC$_6$H$_4$ | 3,4-diHOC$_6$H$_4$ |
| 1041 | 2-HOC$_6$H$_4$ | 4-NH$_2$CH$_2$C$_6$H$_4$ |
| 1042 | 2-HOC$_6$H$_4$ | 3-NH$_2$CH$_2$C$_6$H$_4$ |
| 1043 | 3-HOC$_6$H$_4$ | 4-MeOC$_6$H$_4$ |
| 1044 | 3-HOC$_6$H$_4$ | 3-MeOC$_6$H$_4$ |
| 1045 | 3-HOC$_6$H$_4$ | 4-NH$_2$C$_6$H$_4$ |
| 1046 | 3-HOC$_6$H$_4$ | 3-NH$_2$C$_6$H$_4$ |
| 1047 | 3-HOC$_6$H$_4$ | 2-NH$_2$C$_6$H$_4$ |
| 1048 | 3-HOC$_6$H$_4$ | 4-Me$_2$NC$_6$H$_4$ |
| 1049 | 3-HOC$_6$H$_4$ | 3-Me$_2$NC$_6$H$_4$ |
| 1050 | 3-HOC$_6$H$_4$ | 2-Me$_2$NC$_6$H$_4$ |
| 1051 | 3-HOC$_6$H$_4$ | 4-pyridyl |
| 1052 | 3-HOC$_6$H$_4$ | 3-pyridyl |
| 1053 | 3-HOC$_6$H$_4$ | 2-pyridyl |
| 1054 | 3-HOC$_6$H$_4$ | 2-thiazolyl |
| 1055 | 3-HOC$_6$H$_4$ | 2-pyrazolyl |
| 1056 | 3-HOC$_6$H$_4$ | 5-isoquinolyl |
| 1057 | 3-HOC$_6$H$_4$ | 3,4-methylenedioxyC$_6$H$_3$ |
| 1058 | 3-HOC$_6$H$_4$ | 3,4-ethylenedioxyC$_6$H$_3$ |
| 1059 | 3-HOC$_6$H$_4$ | 2-imidazolyl |
| 1060 | 3-HOC$_6$H$_4$ | 2-oxazolyl |
| 1061 | 3-HOC$_6$H$_4$ | 4-isoxazolyl |
| 1062 | 3-HOC$_6$H$_4$ | 4-HOC$_6$H$_4$ |
| 1063 | 3-HOC$_6$H$_4$ | 3-HOC$_6$H$_4$ |
| 1064 | 3-HOC$_6$H$_4$ | 3,4-diHOC$_6$H$_4$ |
| 1065 | 3-HOC$_6$H$_4$ | 4-NH$_2$CH$_2$C$_6$H$_4$ |
| 1066 | 3-HOC$_6$H$_4$ | 3-NH$_2$CH$_2$C$_6$H$_4$ |
| 1067 | 4-HOC$_6$H$_4$ | 4-MeOC$_6$H$_4$ |
| 1068 | 4-HOC$_6$H$_4$ | 3-MeOC$_6$H$_4$ |
| 1069 | 4-HOC$_6$H$_4$ | 4-NH$_2$C$_6$H$_4$ |
| 1070 | 4-HOC$_6$H$_4$ | 3-NH$_2$C$_6$H$_4$ |
| 1071 | 4-HOC$_6$H$_4$ | 2-NH$_2$C$_6$H$_4$ |
| 1072 | 4-HOC$_6$H$_4$ | 4-Me$_2$NC$_6$H$_4$ |
| 1073 | 4-HOC$_6$H$_4$ | 3-Me$_2$NC$_6$H$_4$ |
| 1074 | 4-HOC$_6$H$_4$ | 2-Me$_2$NC$_6$H$_4$ |
| 1075 | 4-HOC$_6$H$_4$ | 4-pyridyl |
| 1076 | 4-HOC$_6$H$_4$ | 3-pyridyl |
| 1077 | 4-HOC$_6$H$_4$ | 2-pyridyl |
| 1078 | 4-HOC$_6$H$_4$ | 2-thiazolyl |
| 1079 | 4-HOC$_6$H$_4$ | 2-pyrazolyl |
| 1080 | 4-HOC$_6$H$_4$ | 5-isoquinolyl |
| 1081 | 4-HOC$_6$H$_4$ | 3,4-methylenedioxyC$_6$H$_3$ |
| 1082 | 4-HOC$_6$H$_4$ | 3,4-ethylenedioxyC$_6$H$_3$ |
| 1083 | 4-HOC$_6$H$_4$ | 2-imidazolyl |
| 1084 | 4-HOC$_6$H$_4$ | 2-oxazolyl |
| 1085 | 4-HOC$_6$H$_4$ | 4-isoxazolyl |
| 1086 | 4-HOC$_6$H$_4$ | 4-HOC$_6$H$_4$ |
| 1087 | 4-HOC$_6$H$_4$ | 3-HOC$_6$H$_4$ |
| 1088 | 4-HOC$_6$H$_4$ | 3,4-diHOC$_6$H$_4$ |
| 1089 | 4-HOC$_6$H$_4$ | 4-NH$_2$CH$_2$C$_6$H$_4$ |

TABLE 3-continued

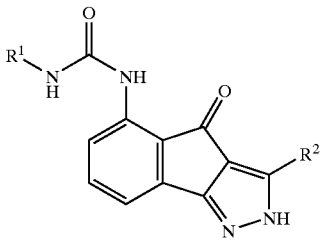

| Example Number | R¹ | R² |
|---|---|---|
| 1090 | 4-HOC₆H₄ | 3-NH₂CH₂C₆H₄ |
| 1091 | 4-ClC₆H₄ | 4-MeOC₆H₄ |
| 1092 | 4-ClC₆H₄ | 3-MeOC₆H₄ |
| 1093 | 4-ClC₆H₄ | 4-NH₂C₆H₄ |
| 1094 | 4-ClC₆H₄ | 3-NH₂C₆H₄ |
| 1095 | 4-ClC₆H₄ | 2-NH₂C₆H₄ |
| 1096 | 4-ClC₆H₄ | 4-Me₂NC₆H₄ |
| 1097 | 4-ClC₆H₄ | 3-Me₂NC₆H₄ |
| 1098 | 4-ClC₆H₄ | 2-Me₂NC₆H₄ |
| 1099 | 4-ClC₆H₄ | 4-pyridyl |
| 1100 | 4-ClC₆H₄ | 3-pyridyl |
| 1101 | 4-ClC₆H₄ | 2-pyridyl |
| 1102 | 4-ClC₆H₄ | 2-thiazolyl |
| 1103 | 4-ClC₆H₄ | 2-pyrazolyl |
| 1104 | 4-ClC₆H₄ | 5-isoquinolyl |
| 1105 | 4-ClC₆H₄ | 3,4-methylenedioxyC₆H₃ |
| 1106 | 4-ClC₆H₄ | 3,4-ethylenedioxyC₆H₃ |
| 1107 | 4-ClC₆H₄ | 2-imidazolyl |
| 1108 | 4-ClC₆H₄ | 2-oxazolyl |
| 1109 | 4-ClC₆H₄ | 4-isoxazolyl |
| 1110 | 4-ClC₆H₄ | 4-HOC₆H₄ |
| 1111 | 4-ClC₆H₄ | 3-HOC₆H₄ |
| 1112 | 4-ClC₆H₄ | 3,4-diHOC₆H₄ |
| 1113 | 4-ClC₆H₄ | 4-NH₂CH₂C₆H₄ |
| 1114 | 4-ClC₆H₄ | 3-NH₂CH₂C₆H₄ |
| 1115 | 2-NH₂CH₂C₆H₄ | 4-MeOC₆H₄ |
| 1116 | 2-NH₂CH₂C₆H₄ | 3-MeOC₆H₄ |
| 1117 | 2-NH₂CH₂C₆H₄ | 4-NH₂C₆H₄ |
| 1118 | 2-NH₂CH₂C₆H₄ | 3-NH₂C₆H₄ |
| 1119 | 2-NH₂CH₂C₆H₄ | 2-NH₂C₆H₄ |
| 1120 | 2-NH₂CH₂C₆H₄ | 4-Me₂NC₆H₄ |
| 1121 | 2-NH₂CH₂C₆H₄ | 3-Me₂NC₆H₄ |
| 1122 | 2-NH₂CH₂C₆H₄ | 2-Me₂NC₆H₄ |
| 1123 | 2-NH₂CH₂C₆H₄ | 4-pyridyl |
| 1124 | 2-NH₂CH₂C₆H₄ | 3-pyridyl |
| 1125 | 2-NH₂CH₂C₆H₄ | 2-pyridyl |
| 1126 | 2-NH₂CH₂C₆H₄ | 2-thiazolyl |
| 1127 | 2-NH₂CH₂C₆H₄ | 2-pyrazolyl |
| 1128 | 2-NH₂CH₂C₆H₄ | 5-isoquinolyl |
| 1129 | 2-NH₂CH₂C₆H₄ | 3,4-methylenedioxyC₆H₃ |
| 1130 | 2-NH₂CH₂C₆H₄ | 3,4-ethylenedioxyC₆H₃ |
| 1131 | 2-NH₂CH₂C₆H₄ | 2-imidazolyl |
| 1132 | 2-NH₂CH₂C₆H₄ | 2-oxazolyl |
| 1133 | 2-NH₂CH₂C₆H₄ | 4-isoxazolyl |
| 1134 | 2-NH₂CH₂C₆H₄ | 4-HOC₆H₄ |
| 1135 | 2-NH₂CH₂C₆H₄ | 3-HOC₆H₄ |
| 1136 | 2-NH₂CH₂C₆H₄ | 3,4-diHOC₆H₄ |
| 1137 | 2-NH₂CH₂C₆H₄ | 4-NH₂CH₂C₆H₄ |
| 1138 | 2-NH₂CH₂C₆H₄ | 3-NH₂CH₂C₆H₄ |
| 1139 | 3-NH₂CH₂C₆H₄ | 4-MeOC₆H₄ |
| 1140 | 3-NH₂CH₂C₆H₄ | 3-MeOC₆H₄ |
| 1141 | 3-NH₂CH₂C₆H₄ | 4-NH₂C₆H₄ |
| 1142 | 3-NH₂CH₂C₆H₄ | 3-NH₂C₆H₄ |
| 1143 | 3-NH₂CH₂C₆H₄ | 2-NH₂C₆H₄ |
| 1144 | 3-NH₂CH₂C₆H₄ | 4-Me₂NC₆H₄ |
| 1145 | 3-NH₂CH₂C₆H₄ | 3-Me₂NC₆H₄ |
| 1146 | 3-NH₂CH₂C₆H₄ | 2-Me₂NC₆H₄ |
| 1147 | 3-NH₂CH₂C₆H₄ | 4-pyridyl |
| 1148 | 3-NH₂CH₂C₆H₄ | 3-pyridyl |
| 1149 | 3-NH₂CH₂C₆H₄ | 2-pyridyl |
| 1150 | 3-NH₂CH₂C₆H₄ | 2-thiazolyl |
| 1151 | 3-NH₂CH₂C₆H₄ | 2-pyrazolyl |
| 1152 | 3-NH₂CH₂C₆H₄ | 5-isoquinolyl |
| 1153 | 3-NH₂CH₂C₆H₄ | 3,4-methylenedioxyC₆H₃ |
| 1154 | 3-NH₂CH₂C₆H₄ | 3,4-ethylenedioxyC₆H₃ |
| 1155 | 3-NH₂CH₂C₆H₄ | 2-imidazolyl |
| 1156 | 3-NH₂CH₂C₆H₄ | 2-oxazolyl |
| 1157 | 3-NH₂CH₂C₆H₄ | 4-isoxazolyl |
| 1158 | 3-NH₂CH₂C₆H₄ | 4-HOC₆H₄ |
| 1159 | 3-NH₂CH₂C₆H₄ | 3-HOC₆H₄ |
| 1160 | 3-NH₂CH₂C₆H₄ | 3,4-diHOC₆H₄ |
| 1161 | 3-NH₂CH₂C₆H₄ | 4-NH₂CH₂C₆H₄ |
| 1162 | 3-NH₂CH₂C₆H₄ | 3-NH₂CH₂C₆H₄ |
| 1163 | 4-NH₂CH₂C₆H₄ | 4-MeOC₆H₄ |
| 1164 | 4-NH₂CH₂C₆H₄ | 3-MeOC₆H₄ |
| 1165 | 4-NH₂CH₂C₆H₄ | 4-NH₂C₆H₄ |
| 1166 | 4-NH₂CH₂C₆H₄ | 3-NH₂C₆H₄ |
| 1167 | 4-NH₂CH₂C₆H₄ | 2-NH₂C₆H₄ |
| 1168 | 4-NH₂CH₂C₆H₄ | 4-Me₂NC₆H₄ |
| 1169 | 4-NH₂CH₂C₆H₄ | 3-Me₂NC₆H₄ |
| 1170 | 4-NH₂CH₂C₆H₄ | 2-Me₂NC₆H₄ |
| 1171 | 4-NH₂CH₂C₆H₄ | 4-pyridyl |
| 1172 | 4-NH₂CH₂C₆H₄ | 3-pyridyl |
| 1173 | 4-NH₂CH₂C₆H₄ | 2-pyridyl |
| 1174 | 4-NH₂CH₂C₆H₄ | 2-thiazolyl |
| 1175 | 4-NH₂CH₂C₆H₄ | 2-pyrazolyl |
| 1176 | 4-NH₂CH₂C₆H₄ | 5-isoquinolyl |
| 1177 | 4-NH₂CH₂C₆H₄ | 3,4-methylenedioxyC₆H₃ |
| 1178 | 4-NH₂CH₂C₆H₄ | 3,4-ethylenedioxyC₆H₃ |
| 1179 | 4-NH₂CH₂C₆H₄ | 2-imidazolyl |
| 1180 | 4-NH₂CH₂C₆H₄ | 2-oxazolyl |
| 1181 | 4-NH₂CH₂C₆H₄ | 4-isoxazolyl |
| 1182 | 4-NH₂CH₂C₆H₄ | 4-HOC₆H₄ |
| 1183 | 4-NH₂CH₂C₆H₄ | 3-HOC₆H₄ |
| 1184 | 4-NH₂CH₂C₆H₄ | 3,4-diHOC₆H₄ |
| 1185 | 4-NH₂CH₂C₆H₄ | 4-NH₂CH₂C₆H₄ |
| 1186 | 4-NH₂CH₂C₆H₄ | 3-NH₂CH₂C₆H₄ |
| 1187 | 2-Me₂NCH₂C₆H₄ | 4-MeOC₆H₄ |
| 1188 | 2-Me₂NCH₂C₆H₄ | 3-MeOC₆H₄ |
| 1189 | 2-Me₂NCH₂C₆H₄ | 4-NH₂C₆H₄ |
| 1190 | 2-Me₂NCH₂C₆H₄ | 3-NH₂C₆H₄ |
| 1191 | 2-Me₂NCH₂C₆H₄ | 2-NH₂C₆H₄ |
| 1192 | 2-Me₂NCH₂C₆H₄ | 4-Me₂NC₆H₄ |
| 1193 | 2-Me₂NCH₂C₆H₄ | 3-Me₂NC₆H₄ |
| 1194 | 2-Me₂NCH₂C₆H₄ | 2-Me₂NC₆H₄ |
| 1195 | 2-Me₂NCH₂C₆H₄ | 4-pyridyl |
| 1196 | 2-Me₂NCH₂C₆H₄ | 3-pyridyl |
| 1197 | 2-Me₂NCH₂C₆H₄ | 2-pyridyl |
| 1198 | 2-Me₂NCH₂C₆H₄ | 2-thiazolyl |
| 1199 | 2-Me₂NCH₂C₆H₄ | 2-pyrazolyl |
| 1200 | 2-Me₂NCH₂C₆H₄ | 5-isoquinolyl |
| 1201 | 2-Me₂NCH₂C₆H₄ | 3,4-methylenedioxyC₆H₃ |
| 1202 | 2-Me₂NCH₂C₆H₄ | 3,4-ethylenedioxyC₆H₃ |
| 1203 | 2-Me₂NCH₂C₆H₄ | 2-imidazolyl |
| 1204 | 2-Me₂NCH₂C₆H₄ | 2-oxazolyl |
| 1205 | 2-Me₂NCH₂C₆H₄ | 4-isoxazolyl |
| 1206 | 2-Me₂NCH₂C₆H₄ | 4-HOC₆H₄ |
| 1207 | 2-Me₂NCH₂C₆H₄ | 3-HOC₆H₄ |
| 1208 | 2-Me₂NCH₂C₆H₄ | 3,4-diHOC₆H₄ |
| 1209 | 2-Me₂NCH₂C₆H₄ | 4-NH₂CH₂C₆H₄ |
| 1210 | 2-Me₂NCH₂C₆H₄ | 3-NH₂CH₂C₆H₄ |
| 1211 | 3-Me₂NCH₂C₆H₄ | 4-MeOC₆H₄ |
| 1212 | 3-Me₂NCH₂C₆H₄ | 3-MeOC₆H₄ |
| 1213 | 3-Me₂NCH₂C₆H₄ | 4-NH₂C₆H₄ |
| 1214 | 3-Me₂NCH₂C₆H₄ | 3-NH₂C₆H₄ |
| 1215 | 3-Me₂NCH₂C₆H₄ | 2-NH₂C₆H₄ |

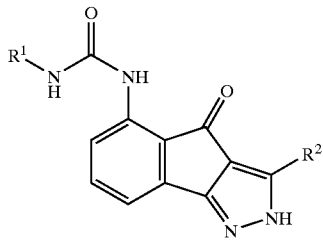

TABLE 3-continued

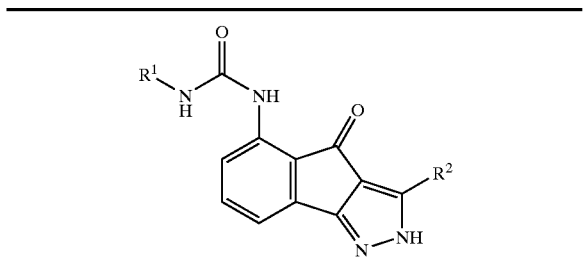

| Example Number | R¹ | R² |
|---|---|---|
| 1216 | 3-Me₂NCH₂C₆H₄ | 4-Me₂NC₆H₄ |
| 1217 | 3-Me₂NCH₂C₆H₄ | 3-Me₂NC₆H₄ |
| 1218 | 3-Me₂NCH₂C₆H₄ | 2-Me₂NC₆H₄ |
| 1219 | 3-Me₂NCH₂C₆H₄ | 4-pyridyl |
| 1220 | 3-Me₂NCH₂C₆H₄ | 3-pyridyl |
| 1221 | 3-Me₂NCH₂C₆H₄ | 2-pyridyl |
| 1222 | 3-Me₂NCH₂C₆H₄ | 2-thiazolyl |
| 1223 | 3-Me₂NCH₂C₆H₄ | 2-pyrazolyl |
| 1224 | 3-Me₂NCH₂C₆H₄ | 5-isoquinolyl |
| 1225 | 3-Me₂NCH₂C₆H₄ | 3,4-methylenedioxyC₆H₃ |
| 1226 | 3-Me₂NCH₂C₆H₄ | 3,4-ethylenedioxyC₆H₃ |
| 1227 | 3-Me₂NCH₂C₆H₄ | 2-imidazolyl |
| 1228 | 3-Me₂NCH₂C₆H₄ | 2-oxazolyl |
| 1229 | 3-Me₂NCH₂C₆H₄ | 4-isoxazolyl |
| 1230 | 3-Me₂NCH₂C₆H₄ | 4-HOC₆H₄ |
| 1231 | 3-Me₂NCH₂C₆H₄ | 3-HOC₆H₄ |
| 1232 | 3-Me₂NCH₂C₆H₄ | 3,4-diHOC₆H₄ |
| 1233 | 3-Me₂NCH₂C₆H₄ | 4-NH₂CH₂C₆H₄ |
| 1234 | 3-Me₂NCH₂C₆H₄ | 3-NH₂CH₂C₆H₄ |
| 1235 | 4-Me₂NCH₂C₆H₄ | 4-MeOC₆H₄ |
| 1236 | 4-Me₂NCH₂C₆H₄ | 3-MeOC₆H₄ |
| 1237 | 4-Me₂NCH₂C₆H₄ | 4-NH₂C₆H₄ |
| 1238 | 4-Me₂NCH₂C₆H₄ | 3-NH₂C₆H₄ |
| 1239 | 4-Me₂NCH₂C₆H₄ | 2-NH₂C₆H₄ |
| 1240 | 4-Me₂NCH₂C₆H₄ | 4-Me₂NC₆H₄ |
| 1241 | 4-Me₂NCH₂C₆H₄ | 3-Me₂NC₆H₄ |
| 1242 | 4-Me₂NCH₂C₆H₄ | 2-Me₂NC₆H₄ |
| 1243 | 4-Me₂NCH₂C₆H₄ | 4-pyridyl |
| 1244 | 4-Me₂NCH₂C₆H₄ | 3-pyridyl |
| 1245 | 4-Me₂NCH₂C₆H₄ | 2-pyridyl |
| 1246 | 4-Me₂NCH₂C₆H₄ | 2-thiazolyl |
| 1247 | 4-Me₂NCH₂C₆H₄ | 2-pyrazolyl |
| 1248 | 4-Me₂NCH₂C₆H₄ | 5-isoquinolyl |
| 1249 | 4-Me₂NCH₂C₆H₄ | 3,4-methylenedioxyC₆H₃ |
| 1250 | 4-Me₂NCH₂C₆H₄ | 3,4-ethylenedioxyC₆H₃ |
| 1251 | 4-Me₂NCH₂C₆H₄ | 2-imidazolyl |
| 1252 | 4-Me₂NCH₂C₆H₄ | 2-oxazolyl |
| 1253 | 4-Me₂NCH₂C₆H₄ | 4-isoxazolyl |
| 1254 | 4-Me₂NCH₂C₆H₄ | 4-HOC₆H₄ |
| 1255 | 4-Me₂NCH₂C₆H₄ | 3-HOC₆H₄ |
| 1256 | 4-Me₂NCH₂C₆H₄ | 3,4-diHOC₆H₄ |
| 1257 | 4-Me₂NCH₂C₆H₄ | 4-NH₂CH₂C₆H₄ |
| 1258 | 4-Me₂NCH₂C₆H₄ | 3-NH₂CH₂C₆H₄ |
| 1259 | H | 4-MeOC₆H₄ |
| 1260 | H | 3-MeOC₆H₄ |
| 1261 | H | 4-NH₂C₆H₄ |
| 1262 | H | 3-NH₂C₆H₄ |
| 1263 | H | 2-NH₂C₆H₄ |
| 1264 | H | 4-Me₂NC₆H₄ |
| 1265 | H | 3-Me₂NC₆H₄ |
| 1266 | H | 2-Me₂NC₆H₄ |
| 1267 | H | 4-pyridyl |
| 1268 | H | 3-pyridyl |
| 1269 | H | 2-pyridyl |
| 1270 | H | 2-thiazolyl |
| 1271 | H | 2-pyrazolyl |
| 1272 | H | 5-isoquinolyl |
| 1273 | H | 3,4-methylenedioxyC₆H₃ |
| 1274 | H | 3,4-ethylenedioxyC₆H₃ |
| 1275 | H | 2-imidazolyl |
| 1276 | H | 2-oxazolyl |
| 1277 | H | 4-isoxazolyl |
| 1278 | H | 4-HOC₆H₄ |

TABLE 3-continued

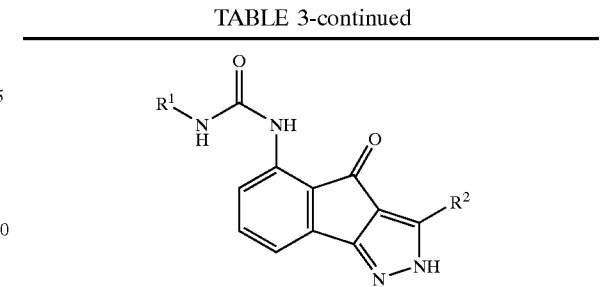

| Example Number | R¹ | R² |
|---|---|---|
| 1279 | H | 3-HOC₆H₄ |
| 1280 | H | 3,4-diHOC₆H₄ |
| 1281 | H | 4-NH₂CH₂C₆H₄ |
| 1282 | H | 3-NH₂CH₂C₆H₄ |
| 1283 | Me | 4-MeOC₆H₄ |
| 1284 | Me | 3-MeOC₆H₄ |
| 1285 | Me | 4-NH₂C₆H₄ |
| 1286 | Me | 3-NH₂C₆H₄ |
| 1287 | Me | 2-NH₂C₆H₄ |
| 1288 | Me | 4-Me₂NC₆H₄ |
| 1289 | Me | 3-Me₂NC₆H₄ |
| 1290 | Me | 2-Me₂NC₆H₄ |
| 1291 | Me | 4-pyridyl |
| 1292 | Me | 3-pyridyl |
| 1293 | Me | 2-pyridyl |
| 1294 | Me | 2-thiazolyl |
| 1295 | Me | 2-pyrazolyl |
| 1296 | Me | 5-isoquinolyl |
| 1297 | Me | 3,4-methylenedioxyC₆H₃ |
| 1298 | Me | 3,4-ethylenedioxyC₆H₃ |
| 1299 | Me | 2-imidazolyl |
| 1300 | Me | 2-oxazolyl |
| 1301 | Me | 4-isoxazolyl |
| 1302 | Me | 4-HOC₆H₄ |
| 1303 | Me | 3-HOC₆H₄ |
| 1304 | Me | 3,4-diHOC₆H₄ |
| 1305 | Me | 4-NH₂CH₂C₆H₄ |
| 1306 | Me | 3-NH₂CH₂C₆H₄ |
| 1307 | Et | 4-MeOC₆H₄ |
| 1308 | Et | 3-MeOC₆H₄ |
| 1309 | Et | 4-NH₂C₆H₄ |
| 1310 | Et | 3-NH₂C₆H₄ |
| 1311 | Et | 2-NH₂C₆H₄ |
| 1312 | Et | 4-Me₂NC₆H₄ |
| 1313 | Et | 3-Me₂NC₆H₄ |
| 1314 | Et | 2-Me₂NC₆H₄ |
| 1315 | Et | 4-pyridyl |
| 1316 | Et | 3-pyridyl |
| 1317 | Et | 2-pyridyl |
| 1318 | Et | 2-thiazolyl |
| 1319 | Et | 2-pyrazolyl |
| 1320 | Et | 5-isoquinolyl |
| 1321 | Et | 3,4-methylenedioxyC₆H₃ |
| 1322 | Et | 3,4-ethylenedioxyC₆H₃ |
| 1323 | Et | 2-imidazolyl |
| 1324 | Et | 2-oxazolyl |
| 1325 | Et | 4-isoxazolyl |
| 1326 | Et | 4-HOC₆H₄ |
| 1327 | Et | 3-HOC₆H₄ |
| 1328 | Et | 3,4-diHOC₆H₄ |
| 1329 | Et | 4-NH₂CH₂C₆H₄ |
| 1330 | Et | 3-NH₂CH₂C₆H₄ |
| 1331 | 2-NH₂C₆H₄CH₂ | 4-MeOC₆H₄ |
| 1332 | 2-NH₂C₆H₄CH₂ | 3-MeOC₆H₄ |
| 1333 | 2-NH₂C₆H₄CH₂ | 4-NH₂C₆H₄ |
| 1334 | 2-NH₂C₆H₄CH₂ | 3-NH₂C₆H₄ |
| 1335 | 2-NH₂C₆H₄CH₂ | 2-NH₂C₆H₄ |
| 1336 | 2-NH₂C₆H₄CH₂ | 4-Me₂NC₆H₄ |
| 1337 | 2-NH₂C₆H₄CH₂ | 3-Me₂NC₆H₄ |
| 1338 | 2-NH₂C₆H₄CH₂ | 2-Me₂NC₆H₄ |
| 1339 | 2-NH₂C₆H₄CH₂ | 4-pyridyl |
| 1340 | 2-NH₂C₆H₄CH₂ | 3-pyridyl |
| 1341 | 2-NH₂C₆H₄CH₂ | 2-pyridyl |

TABLE 3-continued

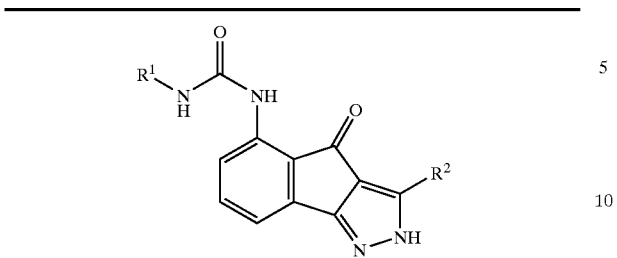

| Example Number | R¹ | R² |
| --- | --- | --- |
| 1342 | 2-NH₂C₆H₄CH₂ | 2-thiazolyl |
| 1343 | 2-NH₂C₆H₄CH₂ | 2-pyrazolyl |
| 1344 | 2-NH₂C₆H₄CH₂ | 5-isoquinolyl |
| 1345 | 2-NH₂C₆H₄CH₂ | 3,4-methylenedioxyC₆H₃ |
| 1346 | 2-NH₂C₆H₄CH₂ | 3-4-ethylenedioxyC₆H₃ |
| 1347 | 2-NH₂C₆H₄CH₂ | 2-imidazolyl |
| 1348 | 2-NH₂C₆H₄CH₂ | 2-oxazolyl |
| 1349 | 2-NH₂C₆H₄CH₂ | 4-isoxazolyl |
| 1350 | 2-NH₂C₆H₄CH₂ | 4-HOC₆H₄ |
| 1351 | 2-NH₂C₆H₄CH₂ | 3-HOC₆H₄ |
| 1352 | 2-NH₂C₆H₄CH₂ | 3,4-diHOC₆H₄ |
| 1353 | 2-NH₂C₆H₄CH₂ | 4-NH₂CH₂C₆H₄ |
| 1354 | 2-NH₂C₆H₄CH₂ | 3-NH₂CH₂C₆H₄ |
| 1355 | 3-NH₂C₆H₄CH₂ | 4-MeOC₆H₄ |
| 1356 | 3-NH₂C₆H₄CH₂ | 3-MeOC₆H₄ |
| 1357 | 3-NH₂C₆H₄CH₂ | 4-NH₂C₆H₄ |
| 1358 | 3-NH₂C₆H₄CH₂ | 3-NH₂C₆H₄ |
| 1359 | 3-NH₂C₆H₄CH₂ | 2-NH₂C₆H₄ |
| 1360 | 3-NH₂C₆H₄CH₂ | 4-Me₂NC₆H₄ |
| 1361 | 3-NH₂C₆H₄CH₂ | 3-Me₂NC₆H₄ |
| 1362 | 3-NH₂C₆H₄CH₂ | 2-Me₂NC₆H₄ |
| 1363 | 3-NH₂C₆H₄CH₂ | 4-pyridyl |
| 1364 | 3-NH₂C₆H₄CH₂ | 3-pyridyl |
| 1365 | 3-NH₂C₆H₄CH₂ | 2-pyridyl |
| 1366 | 3-NH₂C₆H₄CH₂ | 2-thiazolyl |
| 1367 | 3-NH₂C₆H₄CH₂ | 2-pyrazolyl |
| 1367 | 3-NH₂C₆H₄CH₂ | 5-isoquinolyl |
| 1369 | 3-NH₂C₆H₄CH₂ | 3,4-methylenedioxyC₆H₃ |
| 1370 | 3-NH₂C₆H₄CH₂ | 3,4-ethylenedioxyC₆H₃ |
| 1371 | 3-NH₂C₆H₄CH₂ | 2-imidazolyl |
| 1372 | 3-NH₂C₆H₄CH₂ | 2-oxazolyl |
| 1373 | 3-NH₂C₆H₄CH₂ | 4-isoxazolyl |
| 1374 | 3-NH₂C₆H₄CH₂ | 4-HOC₆H₄ |
| 1375 | 3-NH₂C₆H₄CH₂ | 3-HOC₆H₄ |
| 1376 | 3-NH₂C₆H₄CH₂ | 3,4-diHOC₆H₄ |
| 1377 | 3-NH₂C₆H₄CH₂ | 4-NH₂CH₂C₆H₄ |
| 1378 | 3-NH₂C₆H₄CH₂ | 3-NH₂CH₂C₆H₄ |
| 1379 | 4-NH₂C₆H₄CH₂ | 4-MeOC₆H₄ |
| 1380 | 4-NH₂C₆H₄CH₂ | 3-MeOC₆H₄ |
| 1381 | 4-NH₂C₆H₄CH₂ | 4-NH₂C₆H₄ |
| 1382 | 4-NH₂C₆H₄CH₂ | 3-NH₂C₆H₄ |
| 1383 | 4-NH₂C₆H₄CH₂ | 2-NH₂C₆H₄ |
| 1384 | 4-NH₂C₆H₄CH₂ | 4-Me₂NC₆H₄ |
| 1385 | 4-NH₂C₆H₄CH₂ | 3-Me₂NC₆H₄ |
| 1386 | 4-NH₂C₆H₄CH₂ | 2-Me₂NC₆H₄ |
| 1387 | 4-NH₂C₆H₄CH₂ | 4-pyridyl |
| 1388 | 4-NH₂C₆H₄CH₂ | 3-pyridyl |
| 1389 | 4-NH₂C₆H₄CH₂ | 2-pyridyl |
| 1390 | 4-NH₂C₆H₄CH₂ | 2-thiazolyl |
| 1391 | 4-NH₂C₆H₄CH₂ | 2-pyrazolyl |
| 1392 | 4-NH₂C₆H₄CH₂ | 5-isoquinolyl |
| 1393 | 4-NH₂C₆H₄CH₂ | 3,4-methylenedioxyC₆H₃ |
| 1394 | 4-NH₂C₆H₄CH₂ | 3,4-ethylenedioxyC₆H₃ |
| 1395 | 4-NH₂C₆H₄CH₂ | 2-imidazolyl |
| 1396 | 4-NH₂C₆H₄CH₂ | 2-oxazolyl |
| 1397 | 4-NH₂C₆H₄CH₂ | 4-isoxazolyl |
| 1398 | 4-NH₂C₆H₄CH₂ | 4-HOC₆H₄ |
| 1399 | 4-NH₂C₆H₄CH₂ | 3-HOC₆H₄ |
| 1400 | 4-NH₂C₆H₄CH₂ | 3,4-diHOC₆H₄ |
| 1401 | 4-NH₂C₆H₄CH₂ | 4-NH₂CH₂C₆H₄ |
| 1402 | 4-NH₂C₆H₄CH₂ | 3-NH₂CH₂C₆H₄ |
| 1403 | 2-MeOC₆H₄CH₂ | 4-MeOC₆H₄ |
| 1404 | 2-MeOC₆H₄CH₂ | 3-MeOC₆H₄ |

TABLE 3-continued

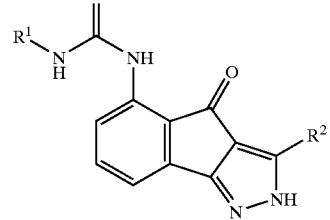

| Example Number | R¹ | R² |
| --- | --- | --- |
| 1405 | 2-MeOC₆H₄CH₂ | 4-NH₂C₆H₄ |
| 1406 | 2-MeOC₆H₄CH₂ | 3-NH₂C₆H₄ |
| 1407 | 2-MeOC₆H₄CH₂ | 2-NH₂C₆H₄ |
| 1408 | 2-MeOC₆H₄CH₂ | 4-Me₂NC₆H₄ |
| 1409 | 2-MeOC₆H₄CH₂ | 3-Me₂NC₆H₄ |
| 1410 | 2-MeOC₆H₄CH₂ | 2-Me₂NC₆H₄ |
| 1411 | 2-MeOC₆H₄CH₂ | 4-pyridyl |
| 1412 | 2-MeOC₆H₄CH₂ | 3-pyridyl |
| 1413 | 2-MeOC₆H₄CH₂ | 2-pyridyl |
| 1414 | 2-MeOC₆H₄CH₂ | 2-thiazolyl |
| 1415 | 2-MeOC₆H₄CH₂ | 2-pyrazolyl |
| 1416 | 2-MeOC₆H₄CH₂ | 5-isoquinolyl |
| 1417 | 2-MeOC₆H₄CH₂ | 3,4-methylenedioxyC₆H₃ |
| 1418 | 2-MeOC₆H₄CH₂ | 3,4-ethylenedioxyC₆H₃ |
| 1419 | 2-MeOC₆H₄CH₂ | 2-imidazolyl |
| 1420 | 2-MeOC₆H₄CH₂ | 2-oxazolyl |
| 1421 | 2-MeOC₆H₄CH₂ | 4-isoxazolyl |
| 1422 | 2-MeOC₆H₄CH₂ | 4-HOC₆H₄ |
| 1423 | 2-MeOC₆H₄CH₂ | 3-HOC₆H₄ |
| 1424 | 2-MeOC₆H₄CH₂ | 3,4-diHOC₆H₄ |
| 1425 | 2-MeOC₆H₄CH₂ | 4-NH₂CH₂C₆H₄ |
| 1426 | 2-MeOC₆H₄CH₂ | 3-NH₂CH₂C₆H₄ |
| 1427 | 3-MeOC₆H₄CH₂ | 4-MeOC₆H₄ |
| 1428 | 3-MeOC₆H₄CH₂ | 3-MeOC₆H₄ |
| 1429 | 3-MeOC₆H₄CH₂ | 4-NH₂C₆H₄ |
| 1430 | 3-MeOC₆H₄CH₂ | 3-NH₂C₆H₄ |
| 1431 | 3-MeOC₆H₄CH₂ | 2-NH₂C₆H₄ |
| 1432 | 3-MeOC₆H₄CH₂ | 4-Me₂NC₆H₄ |
| 1433 | 3-MeOC₆H₄CH₂ | 3-Me₂NC₆H₄ |
| 1434 | 3-MeOC₆H₄CH₂ | 2-Me₂NC₆H₄ |
| 1435 | 3-MeOC₆H₄CH₂ | 4-pyridyl |
| 1436 | 3-MeOC₆H₄CH₂ | 3-pyridyl |
| 1437 | 3-MeOC₆H₄CH₂ | 2-pyridyl |
| 1438 | 3-MeOC₆H₄CH₂ | 2-thiazolyl |
| 1439 | 3-MeOC₆H₄CH₂ | 2-pyrazolyl |
| 1440 | 3-MeOC₆H₄CH₂ | 5-isoquinolyl |
| 1441 | 3-MeOC₆H₄CH₂ | 3,4-methylenedioxyC₆H₃ |
| 1442 | 3-MeOC₆H₄CH₂ | 3,4-ethylenedioxyC₆H₃ |
| 1443 | 3-MeOC₆H₄CH₂ | 2-imidazolyl |
| 1444 | 3-MeOC₆H₄CH₂ | 2-oxazolyl |
| 1445 | 3-MeOC₆H₄CH₂ | 4-isoxazolyl |
| 1446 | 3-MeOC₆H₄CH₂ | 4-HOC₆H₄ |
| 1447 | 3-MeOC₆H₄CH₂ | 3-HOC₆H₄ |
| 1448 | 3-MeOC₆H₄CH₂ | 3,4-diHOC₆H₄ |
| 1449 | 3-MeOC₆H₄CH₂ | 4-NH₂CH₂C₆H₄ |
| 1450 | 3-MeOC₆H₄CH₂ | 3-NH₂CH₂C₆H₄ |
| 1451 | 4-MeOC₆H₄CH₂ | 4-MeOC₆H₄ |
| 1452 | 4-MeOC₆H₄CH₂ | 3-MeOC₆H₄ |
| 1453 | 4-MeOC₆H₄CH₂ | 4-NH₂C₆H₄ |
| 1454 | 4-MeOC₆H₄CH₂ | 3-NH₂C₆H₄ |
| 1455 | 4-MeOC₆H₄CH₂ | 2-NH₂C₆H₄ |
| 1456 | 4-MeOC₆H₄CH₂ | 4-Me₂NC₆H₄ |
| 1457 | 4-MeOC₆H₄CH₂ | 3-Me₂NC₆H₄ |
| 1458 | 4-MeOC₆H₄CH₂ | 2-Me₂NC₆H₄ |
| 1459 | 4-MeOC₆H₄CH₂ | 4-pyridyl |
| 1460 | 4-MeOC₆H₄CH₂ | 3-pyridyl |
| 1461 | 4-MeOC₆H₄CH₂ | 2-pyridyl |
| 1462 | 4-MeOC₆H₄CH₂ | 2-thiazolyl |
| 1463 | 4-MeOC₆H₄CH₂ | 2-pyrazolyl |
| 1464 | 4-MeOC₆H₄CH₂ | 5-isoquinolyl |
| 1465 | 4-MeOC₆H₄CH₂ | 3,4-methylenedioxyC₆H₃ |
| 1466 | 4-MeOC₆H₄CH₂ | 3,4-ethylenedioxyC₆H₃ |
| 1467 | 4-MeOC₆H₄CH₂ | 2-imidazolyl |

TABLE 3-continued

| Example Number | R$^1$ | R$^2$ |
|---|---|---|
| 1468 | 4-MeOC$_6$H$_4$CH$_2$ | 2-oxazolyl |
| 1469 | 4-MeOC$_6$H$_4$CH$_2$ | 4-isoxazolyl |
| 1470 | 4-MeOC$_6$H$_4$CH$_2$ | 4-HOC$_6$H$_4$ |
| 1471 | 4-MeOC$_6$H$_4$CH$_2$ | 3-HOC$_6$H$_4$ |
| 1472 | 4-MeOC$_6$H$_4$CH$_2$ | 3,4-diHOC$_6$H$_4$ |
| 1473 | 4-MeOC$_6$H$_4$CH$_2$ | 4-NH$_2$CH$_2$C$_6$H$_4$ |
| 1474 | 4-MeOC$_6$H$_4$CH$_2$ | 3-NH$_2$CH$_2$C$_6$H$_4$ |
| 1475 | 2-HOC$_6$H$_4$CH$_2$ | 4-MeOC$_6$H$_4$ |
| 1476 | 2-HOC$_6$H$_4$CH$_2$ | 3-MeOC$_6$H$_4$ |
| 1477 | 2-HOC$_6$H$_4$CH$_2$ | 4-NH$_2$C$_6$H$_4$ |
| 1478 | 2-HOC$_6$H$_4$CH$_2$ | 3-NH$_2$C$_6$H$_4$ |
| 1479 | 2-HOC$_6$H$_4$CH$_2$ | 2-NH$_2$C$_6$H$_4$ |
| 1480 | 2-HOC$_6$H$_4$CH$_2$ | 4-Me$_2$NC$_6$H$_4$ |
| 1481 | 2-HOC$_6$H$_4$CH$_2$ | 3-Me$_2$NC$_6$H$_4$ |
| 1482 | 2-HOC$_6$H$_4$CH$_2$ | 2-Me$_2$NC$_6$H$_4$ |
| 1483 | 2-HOC$_6$H$_4$CH$_2$ | 4-pyridyl |
| 1484 | 2-HOC$_6$H$_4$CH$_2$ | 3-pyridyl |
| 1485 | 2-HOC$_6$H$_4$CH$_2$ | 2-pyridyl |
| 1486 | 2-HOC$_6$H$_4$CH$_2$ | 2-thiazolyl |
| 1487 | 2-HOC$_6$H$_4$CH$_2$ | 2-pyrazolyl |
| 1488 | 2-HOC$_6$H$_4$CH$_2$ | 5-isoquinolyl |
| 1489 | 2-HOC$_6$H$_4$CH$_2$ | 3,4-methylenedioxyC$_6$H$_3$ |
| 1490 | 2-HOC$_6$H$_4$CH$_2$ | 3,4-ethylenedioxyC$_6$H$_3$ |
| 1491 | 2-HOC$_6$H$_4$CH$_2$ | 2-imidazolyl |
| 1492 | 2-HOC$_6$H$_4$CH$_2$ | 2-oxazolyl |
| 1493 | 2-HOC$_6$H$_4$CH$_2$ | 4-isoxazolyl |
| 1494 | 2-HOC$_6$H$_4$CH$_2$ | 4-HOC$_6$H$_4$ |
| 1495 | 2-HOC$_6$H$_4$CH$_2$ | 3-HOC$_6$H$_4$ |
| 1496 | 2-HOC$_6$H$_4$CH$_2$ | 3,4-diHOC$_6$H$_4$ |
| 1497 | 2-HOC$_6$H$_4$CH$_2$ | 4-NH$_2$CH$_2$C$_6$H$_4$ |
| 1498 | 2-HOC$_6$H$_4$CH$_2$ | 3-NH$_2$CH$_2$C$_6$H$_4$ |
| 1499 | 3-HOC$_6$H$_4$CH$_2$ | 4-MeOC$_6$H$_4$ |
| 1500 | 3-HOC$_6$H$_4$CH$_2$ | 3-MeOC$_6$H$_4$ |
| 1501 | 3-HOC$_6$H$_4$CH$_2$ | 4-NH$_2$C$_6$H$_4$ |
| 1502 | 3-HOC$_6$H$_4$CH$_2$ | 3-NH$_2$C$_6$H$_4$ |
| 1503 | 3-HOC$_6$H$_4$CH$_2$ | 2-NH$_2$C$_6$H$_4$ |
| 1504 | 3-HOC$_6$H$_4$CH$_2$ | 4-Me$_2$NC$_6$H$_4$ |
| 1505 | 3-HOC$_6$H$_4$CH$_2$ | 3-Me$_2$NC$_6$H$_4$ |
| 1506 | 3-HOC$_6$H$_4$CH$_2$ | 2-Me$_2$NC$_6$H$_4$ |
| 1507 | 3-HOC$_6$H$_4$CH$_2$ | 4-pyridyl |
| 1508 | 3-HOC$_6$H$_4$CH$_2$ | 3-pyridyl |
| 1509 | 3-HOC$_6$H$_4$CH$_2$ | 2-pyridyl |
| 1510 | 3-HOC$_6$H$_4$CH$_2$ | 2-thiazolyl |
| 1511 | 3-HOC$_6$H$_4$CH$_2$ | 2-pyrazolyl |
| 1512 | 3-HOC$_6$H$_4$CH$_2$ | 5-isoquinolyl |
| 1513 | 3-HOC$_6$H$_4$CH$_2$ | 3,4-methylenedioxyC$_6$H$_3$ |
| 1514 | 3-HOC$_6$H$_4$CH$_2$ | 3,4-ethylenedioxyC$_6$H$_3$ |
| 1514 | 3-HOC$_6$H$_4$CH$_2$ | 2-imidazolyl |
| 1516 | 3-HOC$_6$H$_4$CH$_2$ | 2-oxazolyl |
| 1517 | 3-HOC$_6$H$_4$CH$_2$ | 4-isoxazolyl |
| 1518 | 3-HOC$_6$H$_4$CH$_2$ | 4-HOC$_6$H$_4$ |
| 1519 | 3-HOC$_6$H$_4$CH$_2$ | 3-HOC$_6$H$_4$ |
| 1520 | 3-HOC$_6$H$_4$CH$_2$ | 3,4-diHOC$_6$H$_4$ |
| 1521 | 3-HOC$_6$H$_4$CH$_2$ | 4-NH$_2$CH$_2$C$_6$H$_4$ |
| 1522 | 3-HOC$_6$H$_4$CH$_2$ | 3-NH$_2$CH$_2$C$_6$H$_4$ |
| 1523 | 4-HOC$_6$H$_4$CH$_2$ | 4-MeOC$_6$H$_4$ |
| 1524 | 4-HOC$_6$H$_4$CH$_2$ | 3-MeOC$_6$H$_4$ |
| 1525 | 4-HOC$_6$H$_4$CH$_2$ | 4-NH$_2$C$_6$H$_4$ |
| 1526 | 4-HOC$_6$H$_4$CH$_2$ | 3-NH$_2$C$_6$H$_4$ |
| 1527 | 4-HOC$_6$H$_4$CH$_2$ | 2-NH$_2$C$_6$H$_4$ |
| 1528 | 4-HOC$_6$H$_4$CH$_2$ | 4-Me$_2$NC$_6$H$_4$ |
| 1529 | 4-HOC$_6$H$_4$CH$_2$ | 3-Me$_2$NC$_6$H$_4$ |
| 1530 | 4-HOC$_6$H$_4$CH$_2$ | 2-Me$_2$NC$_6$H$_4$ |
| 1531 | 4-HOC$_6$H$_4$CH$_2$ | 4-pyridyl |
| 1532 | 4-HOC$_6$H$_4$CH$_2$ | 3-pyridyl |
| 1533 | 4-HOC$_6$H$_4$CH$_2$ | 2-pyridyl |
| 1534 | 4-HOC$_6$H$_4$CH$_2$ | 2-thiazolyl |
| 1535 | 4-HOC$_6$H$_4$CH$_2$ | 2-pyrazolyl |
| 1536 | 4-HOC$_6$H$_4$CH$_2$ | 5-isoquinolyl |
| 1537 | 4-HOC$_6$H$_4$CH$_2$ | 3,4-methylenedioxyC$_6$H$_3$ |
| 1538 | 4-HOC$_6$H$_4$CH$_2$ | 3,4-ethylenedioxyC$_6$H$_3$ |
| 1539 | 4-HOC$_6$H$_4$CH$_2$ | 2-imidazolyl |
| 1540 | 4-HOC$_6$H$_4$CH$_2$ | 2-oxazolyl |
| 1541 | 4-HOC$_6$H$_4$CH$_2$ | 4-isoxazolyl |
| 1542 | 4-HOC$_6$H$_4$CH$_2$ | 4-HOC$_6$H$_4$ |
| 1543 | 4-HOC$_6$H$_4$CH$_2$ | 3-HOC$_6$H$_4$ |
| 1544 | 4-HOC$_6$H$_4$CH$_2$ | 3,4-diHOC$_6$H$_4$ |
| 1545 | 4-HOC$_6$H$_4$CH$_2$ | 4-NH$_2$CH$_2$C$_6$H$_4$ |
| 1546 | 4-HOC$_6$H$_4$CH$_2$ | 3-NH$_2$CH$_2$C$_6$H$_4$ |
| 1547 | 4-ClC$_6$H$_4$CH$_2$ | 4-MeOC$_6$H$_4$ |
| 1548 | 4-ClC$_6$H$_4$CH$_2$ | 3-MeOC$_6$H$_4$ |
| 1549 | 4-ClC$_6$H$_4$CH$_2$ | 4-NH$_2$C$_6$H$_4$ |
| 1550 | 4-ClC$_6$H$_4$CH$_2$ | 3-NH$_2$C$_6$H$_4$ |
| 1551 | 4-ClC$_6$H$_4$CH$_2$ | 2-NH$_2$C$_6$H$_4$ |
| 1552 | 4-ClC$_6$H$_4$CH$_2$ | 4-Me$_2$NC$_6$H$_4$ |
| 1553 | 4-ClC$_6$H$_4$CH$_2$ | 3-Me$_2$NC$_6$H$_4$ |
| 1554 | 4-ClC$_6$H$_4$CH$_2$ | 2-Me$_2$NC$_6$H$_4$ |
| 1555 | 4-ClC$_6$H$_4$CH$_2$ | 4-pyridyl |
| 1556 | 4-ClC$_6$H$_4$CH$_2$ | 3-pyridyl |
| 1557 | 4-ClC$_6$H$_4$CH$_2$ | 2-pyridyl |
| 1558 | 4-ClC$_6$H$_4$CH$_2$ | 2-thiazolyl |
| 1559 | 4-ClC$_6$H$_4$CH$_2$ | 2-pyrazolyl |
| 1560 | 4-ClC$_6$H$_4$CH$_2$ | 5-isoquinolyl |
| 1561 | 4-ClC$_6$H$_4$CH$_2$ | 3,4-methylenedioxyC$_6$H$_3$ |
| 1562 | 4-ClC$_6$H$_4$CH$_2$ | 3,4-ethylenedioxyC$_6$H$_3$ |
| 1563 | 4-ClC$_6$H$_4$CH$_2$ | 2-imidazolyl |
| 1564 | 4-ClC$_6$H$_4$CH$_2$ | 2-oxazolyl |
| 1565 | 4-ClC$_6$H$_4$CH$_2$ | 4-isoxazolyl |
| 1566 | 4-ClC$_6$H$_4$CH$_2$ | 4-HOC$_6$H$_4$ |
| 1567 | 4-ClC$_6$H$_4$CH$_2$ | 3-HOC$_6$H$_4$ |
| 1568 | 4-ClC$_6$H$_4$CH$_2$ | 3,4-diHOC$_6$H$_4$ |
| 1569 | 4-ClC$_6$H$_4$CH$_2$ | 4-NH$_2$CH$_2$C$_6$H$_4$ |
| 1570 | 4-ClC$_6$H$_4$CH$_2$ | 3-NH$_2$CH$_2$C$_6$H$_4$ |
| 1571 | 2-NH$_2$CH$_2$C$_6$H$_4$CH$_2$ | 4-MeOC$_6$H$_4$ |
| 1572 | 2-NH$_2$CH$_2$C$_6$H$_4$CH$_2$ | 3-MeOC$_6$H$_4$ |
| 1573 | 2-NH$_2$CH$_2$C$_6$H$_4$CH$_2$ | 4-NH$_2$C$_6$H$_4$ |
| 1574 | 2-NH$_2$CH$_2$C$_6$H$_4$CH$_2$ | 3-NH$_2$C$_6$H$_4$ |
| 1575 | 2-NH$_2$CH$_2$C$_6$H$_4$CH$_2$ | 2-NH$_2$C$_6$H$_4$ |
| 1576 | 2-NH$_2$CH$_2$C$_6$H$_4$CH$_2$ | 4-Me$_2$NC$_6$H$_4$ |
| 1577 | 2-NH$_2$CH$_2$C$_6$H$_4$CH$_2$ | 3-Me$_2$NC$_6$H$_4$ |
| 1578 | 2-NH$_2$CH$_2$C$_6$H$_4$CH$_2$ | 2-Me$_2$NC$_6$H$_4$ |
| 1579 | 2-NH$_2$CH$_2$C$_6$H$_4$CH$_2$ | 4-pyridyl |
| 1580 | 2-NH$_2$CH$_2$C$_6$H$_4$CH$_2$ | 3-pyridyl |
| 1581 | 2-NH$_2$CH$_2$C$_6$H$_4$CH$_2$ | 2-pyridyl |
| 1582 | 2-NH$_2$CH$_2$C$_6$H$_4$CH$_2$ | 2-thiazolyl |
| 1583 | 2-NH$_2$CH$_2$C$_6$H$_4$CH$_2$ | 2-pyrazolyl |
| 1584 | 2-NH$_2$CH$_2$C$_6$H$_4$CH$_2$ | 5-isoquinolyl |
| 1585 | 2-NH$_2$CH$_2$C$_6$H$_4$CH$_2$ | 3,4-methylenedioxyC$_6$H$_3$ |
| 1586 | 2-NH$_2$CH$_2$C$_6$H$_4$CH$_2$ | 3,4-ethylenedioxyC$_6$H$_3$ |
| 1587 | 2-NH$_2$CH$_2$C$_6$H$_4$CH$_2$ | 2-imidazolyl |
| 1588 | N-NH$_2$CH$_2$C$_6$H$_4$CH$_2$ | 2-oxazolyl |
| 1589 | 2-NH$_2$CH$_2$C$_6$H$_4$CH$_2$ | 4-isoxazolyl |
| 1590 | 2-NH$_2$CH$_2$C$_6$H$_4$CH$_2$ | 4-HOC$_6$H$_4$ |
| 1591 | 2-NH$_2$CH$_2$C$_6$H$_4$CH$_2$ | 3-HOC$_6$H$_4$ |
| 1592 | 2-NH$_2$CH$_2$C$_6$H$_4$CH$_2$ | 3,4-diHOC$_6$H$_4$ |
| 1593 | 2-NH$_2$CH$_2$C$_6$H$_4$CH$_2$ | 4-NH$_2$CH$_2$C$_6$H$_4$ |

TABLE 3-continued

| Example Number | R¹ | R² |
|---|---|---|
| 1594 | 2-NH$_2$CH$_2$C$_6$H$_4$CH$_2$ | 3-NH$_2$CH$_2$C$_6$H$_4$ |
| 1595 | 3-NH$_2$CH$_2$C$_6$H$_4$CH$_2$ | 4-MeOC$_6$H$_4$ |
| 1596 | 3-NH$_2$CH$_2$C$_6$H$_4$CH$_2$ | 3-MeOC$_6$H$_4$ |
| 1597 | 3-NH$_2$CH$_2$C$_6$H$_4$CH$_2$ | 4-NH$_2$C$_6$H$_4$ |
| 1598 | 3-NH$_2$CH$_2$C$_6$H$_4$CH$_2$ | 3-NH$_2$C$_6$H$_4$ |
| 1599 | 3-NH$_2$CH$_2$C$_6$H$_4$CH$_2$ | 2-NH$_2$C$_6$H$_4$ |
| 1600 | 3-NH$_2$CH$_2$C$_6$H$_4$CH$_2$ | 4-Me$_2$NC$_6$H$_4$ |
| 1601 | 3-NH$_2$CH$_2$C$_6$H$_4$CH$_2$ | 3-Me$_2$NC$_6$H$_4$ |
| 1602 | 3-NH$_2$CH$_2$C$_6$H$_4$CH$_2$ | 2-Me$_2$NC$_6$H$_4$ |
| 1603 | 3-NH$_2$CH$_2$C$_6$H$_4$CH$_2$ | 4-pyridyl |
| 1604 | 3-NH$_2$CH$_2$C$_6$H$_4$CH$_2$ | 3-pyridyl |
| 1605 | 3-NH$_2$CH$_2$C$_6$H$_4$CH$_2$ | 2-pyridyl |
| 1606 | 3-NH$_2$CH$_2$C$_6$H$_4$CH$_2$ | 2-thiazolyl |
| 1607 | 3-NH$_2$CH$_2$C$_6$H$_4$CH$_2$ | 2-pyrazolyl |
| 1608 | 3-NH$_2$CH$_2$C$_6$H$_4$CH$_2$ | 5-isoquinolyl |
| 1609 | 3-NH$_2$CH$_2$C$_6$H$_4$CH$_2$ | 3,4-methylenedioxyC$_6$H$_3$ |
| 1610 | 3-NH$_2$CH$_2$C$_6$H$_4$CH$_2$ | 3,4-ethylenedioxyC$_6$H$_3$ |
| 1611 | 3-NH$_2$CH$_2$C$_6$H$_4$CH$_2$ | 2-imidazolyl |
| 1612 | 3-NH$_2$CH$_2$C$_6$H$_4$CH$_2$ | 2-oxazolyl |
| 1613 | 3-NH$_2$CH$_2$C$_6$H$_4$CH$_2$ | 4-isoxazolyl |
| 1614 | 3-NH$_2$CH$_2$C$_6$H$_4$CH$_2$ | 4-HOC$_6$H$_4$ |
| 1615 | 3-NH$_2$CH$_2$C$_6$H$_4$CH$_2$ | 3-HOC$_6$H$_4$ |
| 1616 | 3-NH$_2$CH$_2$C$_6$H$_4$CH$_2$ | 3,4-diHOC$_6$H$_4$ |
| 1617 | 3-NH$_2$CH$_2$C$_6$H$_4$CH$_2$ | 4-NH$_2$CH$_2$C$_6$H$_4$ |
| 1618 | 3-NH$_2$CH$_2$C$_6$H$_4$CH$_2$ | 3-NH$_2$CH$_2$C$_6$H$_4$ |
| 1619 | 4-NH$_2$CH$_2$C$_6$H$_4$CH$_2$ | 4-MeOC$_6$H$_4$ |
| 1620 | 4-NH$_2$CH$_2$C$_6$H$_4$CH$_2$ | 3-MeOC$_6$H$_4$ |
| 1621 | 4-NH$_2$CH$_2$C$_6$H$_4$CH$_2$ | 4-NH$_2$C$_6$H$_4$ |
| 1622 | 4-NH$_2$CH$_2$C$_6$H$_4$CH$_2$ | 3-NH$_2$C$_6$H$_4$ |
| 1623 | 4-NH$_2$CH$_2$C$_6$H$_4$CH$_2$ | 2-NH$_2$C$_6$H$_4$ |
| 1624 | 4-NH$_2$CH$_2$C$_6$H$_4$CH$_2$ | 4-Me$_2$NC$_6$H$_4$ |
| 1625 | 4-NH$_2$CH$_2$C$_6$H$_4$CH$_2$ | 3-Me$_2$NC$_6$H$_4$ |
| 1626 | 4-NH$_2$CH$_2$C$_6$H$_4$CH$_2$ | 2-Me$_2$NC$_6$H$_4$ |
| 1627 | 4-NH$_2$CH$_2$C$_6$H$_4$CH$_2$ | 4-pyridyl |
| 1628 | 4-NH$_2$CH$_2$C$_6$H$_4$CH$_2$ | 3-pyridyl |
| 1629 | 4-NH$_2$CH$_2$C$_6$H$_4$CH$_2$ | 2-pyridyl |
| 1630 | 4-NH$_2$CH$_2$C$_6$H$_4$CH$_2$ | 2-thiazolyl |
| 1631 | 4-NH$_2$CH$_2$C$_6$H$_4$CH$_2$ | 2-pyrazolyl |
| 1632 | 4-NH$_2$CH$_2$C$_6$H$_4$CH$_2$ | 5-isoquinolyl |
| 1633 | 4-NH$_2$CH$_2$C$_6$H$_4$CH$_2$ | 3,4-methylenedioxyC$_6$H$_3$ |
| 1634 | 4-NH$_2$CH$_2$C$_6$H$_4$CH$_2$ | 3,4-ethylenedioxyC$_6$H$_3$ |
| 1635 | 4-NH$_2$CH$_2$C$_6$H$_4$CH$_2$ | 2-imidazolyl |
| 1636 | 4-NH$_2$CH$_2$C$_6$H$_4$CH$_2$ | 2-oxazolyl |
| 1637 | 4-NH$_2$CH$_2$C$_6$H$_4$CH$_2$ | 4-isoxazolyl |
| 1638 | 4-NH$_2$CH$_2$C$_6$H$_4$CH$_2$ | 4-HOC$_6$H$_4$ |
| 1639 | 4-NH$_2$CH$_2$C$_6$H$_4$CH$_2$ | 3-HOC$_6$H$_4$ |
| 1640 | 4-NH$_2$CH$_2$C$_6$H$_4$CH$_2$ | 3,4-diHOC$_6$H$_4$ |
| 1641 | 4-NH$_2$CH$_2$C$_6$H$_4$CH$_2$ | 4-NH$_2$CH$_2$C$_6$H$_4$ |
| 1642 | 4-NH$_2$CH$_2$C$_6$H$_4$CH$_2$ | 3-NH$_2$CH$_2$C$_6$H$_4$ |
| 1643 | 2-Me$_2$NCH$_2$C$_6$H$_4$CH$_2$ | 4-MeOC$_6$H$_4$ |
| 1644 | 2-Me$_2$NCH$_2$C$_6$H$_4$CH$_2$ | 3-MeOC$_6$H$_4$ |
| 1645 | 2-Me$_2$NCH$_2$C$_6$H$_4$CH$_2$ | 4-NH$_2$C$_6$H$_4$ |
| 1646 | 2-Me$_2$NCH$_2$C$_6$H$_4$CH$_2$ | 3-NH$_2$C$_6$H$_4$ |
| 1647 | 2-Me$_2$NCH$_2$C$_6$H$_4$CH$_2$ | 2-NH$_2$C$_6$H$_4$ |
| 1648 | 2-Me$_2$NCH$_2$C$_6$H$_4$CH$_2$ | 4-Me$_2$NC$_6$H$_4$ |
| 1649 | 2-Me$_2$NCH$_2$C$_6$H$_4$CH$_2$ | 3-Me$_2$NC$_6$H$_4$ |
| 1650 | 2-Me$_2$NCH$_2$C$_6$H$_4$CH$_2$ | 2-Me$_2$NC$_6$H$_4$ |
| 1651 | 2-Me$_2$NCH$_2$C$_6$H$_4$CH$_2$ | 4-pyridyl |
| 1652 | 2-Me$_2$NCH$_2$C$_6$H$_4$CH$_2$ | 3-pyridyl |
| 1653 | 2-Me$_2$NCH$_2$C$_6$H$_4$CH$_2$ | 2-pyridyl |
| 1654 | 2-Me$_2$NCH$_2$C$_6$H$_4$CH$_2$ | 2-thiazolyl |
| 1655 | 2-Me$_2$NCH$_2$C$_6$H$_4$CH$_2$ | 2-pyrazolyl |
| 1656 | 2-Me$_2$NCH$_2$C$_6$H$_4$CH$_2$ | 5-isoquinolyl |
| 1657 | 2-Me$_2$NCH$_2$C$_6$H$_4$CH$_2$ | 3,4-methylenedioxyC$_6$H$_3$ |
| 1658 | 2-Me$_2$NCH$_2$C$_6$H$_4$CH$_2$ | 3,4-ethylenedioxyC$_6$H$_3$ |
| 1659 | 2-Me$_2$NCH$_2$C$_6$H$_4$CH$_2$ | 2-imidazolyl |
| 1660 | 2-Me$_2$NCH$_2$C$_6$H$_4$CH$_2$ | 2-oxazolyl |
| 1661 | 2-Me$_2$NCH$_2$C$_6$H$_4$CH$_2$ | 4-isoxazolyl |
| 1662 | 2-Me$_2$NCH$_2$C$_6$H$_4$CH$_2$ | 4-HOC$_6$H$_4$ |
| 1663 | 2-Me$_2$NCH$_2$C$_6$H$_4$CH$_2$ | 3-HOC$_6$H$_4$ |
| 1664 | 2-Me$_2$NCH$_2$C$_6$H$_4$CH$_2$ | 3,4-diHOC$_6$H$_4$ |
| 1665 | 2-Me$_2$NCH$_2$C$_6$H$_4$CH$_2$ | 4-NH$_2$CH$_2$C$_6$H$_4$ |
| 1666 | 2-Me$_2$NCH$_2$C$_6$H$_4$CH$_2$ | 3-NH$_2$CH$_2$C$_6$H$_4$ |
| 1667 | 3-Me$_2$NCH$_2$C$_6$H$_4$CH$_2$ | 4-MeOC$_6$H$_4$ |
| 1668 | 3-Me$_2$NCH$_2$C$_6$H$_4$CH$_2$ | 3-MeOC$_6$H$_4$ |
| 1669 | 3-Me$_2$NCH$_2$C$_6$H$_4$CH$_2$ | 4-NH$_2$C$_6$H$_4$ |
| 1670 | 3-Me$_2$NCH$_2$C$_6$H$_4$CH$_2$ | 3-NH$_2$C$_6$H$_4$ |
| 1671 | 3-Me$_2$NCH$_2$C$_6$H$_4$CH$_2$ | 2-NH$_2$C$_6$H$_4$ |
| 1672 | 3-Me$_2$NCH$_2$C$_6$H$_4$CH$_2$ | 4-Me$_2$NC$_6$H$_4$ |
| 1673 | 3-Me$_2$NCH$_2$C$_6$H$_4$CH$_2$ | 3-Me$_2$NC$_6$H$_4$ |
| 1674 | 3-Me$_2$NCH$_2$C$_6$H$_4$CH$_2$ | 2-Me$_2$NC$_6$H$_4$ |
| 1675 | 3-Me$_2$NCH$_2$C$_6$H$_4$CH$_2$ | 4-pyridyl |
| 1676 | 3-Me$_2$NCH$_2$C$_6$H$_4$CH$_2$ | 3-pyridyl |
| 1677 | 3-Me$_2$NCH$_2$C$_6$H$_4$CH$_2$ | 2-pyridyl |
| 1678 | 3-Me$_2$NCH$_2$C$_6$H$_4$CH$_2$ | 2-thiazolyl |
| 1679 | 3-Me$_2$NCH$_2$C$_6$H$_4$CH$_2$ | 2-pyrazolyl |
| 1680 | 3-Me$_2$NCH$_2$C$_6$H$_4$CH$_2$ | 5-isoquinolyl |
| 1681 | 3-Me$_2$NCH$_2$C$_6$H$_4$CH$_2$ | 3,4-methylenedioxyC$_6$H$_3$ |
| 1682 | 3-Me$_2$NCH$_2$C$_6$H$_4$CH$_2$ | 3,4-ethylenedioxyC$_6$H$_3$ |
| 1683 | 3-Me$_2$NCH$_2$C$_6$H$_4$CH$_2$ | 2-imidazolyl |
| 1684 | 3-Me$_2$NCH$_2$C$_6$H$_4$CH$_2$ | 2-oxazolyl |
| 1685 | 3-Me$_2$NCH$_2$C$_6$H$_4$CH$_2$ | 4-isoxazolyl |
| 1686 | 3-Me$_2$NCH$_2$C$_6$H$_4$CH$_2$ | 4-HOC$_6$H$_4$ |
| 1687 | 3-Me$_2$NCH$_2$C$_6$H$_4$CH$_2$ | 3-HOC$_6$H$_4$ |
| 1688 | 3-Me$_2$NCH$_2$C$_6$H$_4$CH$_2$ | 3,4-diHOC$_6$H$_4$ |
| 1689 | 3-Me$_2$NCH$_2$C$_6$H$_4$CH$_2$ | 4-NH$_2$CH$_2$C$_6$H$_4$ |
| 1690 | 3-Me$_2$NCH$_2$C$_6$H$_4$CH$_2$ | 3-NH$_2$CH$_2$C$_6$H$_4$ |
| 1691 | 4-Me$_2$NCH$_2$C$_6$H$_4$CH$_2$ | 4-MeOC$_6$H$_4$ |
| 1692 | 4-Me$_2$NCH$_2$C$_6$H$_4$CH$_2$ | 3-MeOC$_6$H$_4$ |
| 1693 | 4-Me$_2$NCH$_2$C$_6$H$_4$CH$_2$ | 4-NH$_2$C$_6$H$_4$ |
| 1694 | 4-Me$_2$NCH$_2$C$_6$H$_4$CH$_2$ | 3-NH$_2$C$_6$H$_4$ |
| 1695 | 4-Me$_2$NCH$_2$C$_6$H$_4$CH$_2$ | 2-NH$_2$C$_6$H$_4$ |
| 1696 | 4-Me$_2$NCH$_2$C$_6$H$_4$CH$_2$ | 4-Me$_2$NC$_6$H$_4$ |
| 1697 | 4-Me$_2$NCH$_2$C$_6$H$_4$CH$_2$ | 3-Me$_2$NC$_6$H$_4$ |
| 1698 | 4-Me$_2$NCH$_2$C$_6$H$_4$CH$_2$ | 2-Me$_2$NC$_6$H$_4$ |
| 1699 | 4-Me$_2$NCH$_2$C$_6$H$_4$CH$_2$ | 4-pyridyl |
| 1700 | 4-Me$_2$NCH$_2$C$_6$H$_4$CH$_2$ | 3-pyridyl |
| 1701 | 4-Me$_2$NCH$_2$C$_6$H$_4$CH$_2$ | 2-pyridyl |
| 1702 | 4-Me$_2$NCH$_2$C$_6$H$_4$CH$_2$ | 2-thiazolyl |
| 1703 | 4-Me$_2$NCH$_2$C$_6$H$_4$CH$_2$ | 2-pyrazolyl |
| 1704 | 4-Me$_2$NCH$_2$C$_6$H$_4$CH$_2$ | 5-isoquinolyl |
| 1705 | 4-Me$_2$NCH$_2$C$_6$H$_4$CH$_2$ | 3,4-methylenedioxyC$_6$H$_3$ |
| 1706 | 4-Me$_2$NCH$_2$C$_6$H$_4$CH$_2$ | 3,4-ethylenedioxyC$_6$H$_3$ |
| 1707 | 4-Me$_2$NCH$_2$C$_6$H$_4$CH$_2$ | 2-imidazolyl |
| 1708 | 4-Me$_2$NCH$_2$C$_6$H$_4$CH$_2$ | 2-oxazolyl |
| 1709 | 4-Me$_2$NCH$_2$C$_6$H$_4$CH$_2$ | 4-isoxazolyl |
| 1710 | 4-Me$_2$NCH$_2$C$_6$H$_4$CH$_2$ | 4-HOC$_6$H$_4$ |
| 1711 | 4-Me$_2$NCH$_2$C$_6$H$_4$CH$_2$ | 3-HOC$_6$H$_4$ |
| 1712 | 4-Me$_2$NCH$_2$C$_6$H$_4$CH$_2$ | 3,4-diHOC$_6$H$_4$ |
| 1713 | 4-Me$_2$NCH$_2$C$_6$H$_4$CH$_2$ | 4-NH$_2$CH$_2$C$_6$H$_4$ |
| 1714 | 4-Me$_2$NCH$_2$C$_6$H$_4$CH$_2$ | 3-NH$_2$CH$_2$C$_6$H$_4$ |

TABLE 4

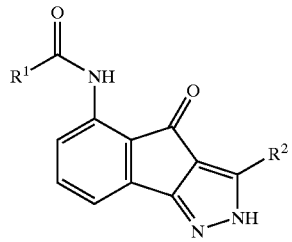

| Example Number | R¹ | R² |
|---|---|---|
| 1715 | Methyl | 4-MeOC₆H₄ |
| 1716 | ClCH₂ | 4-MeOC₆H₄ |
| 1717 | Cyclopropyl | 4-MeOC₆H₄ |
| 1718 | Isopropyl | 4-MeOC₆H₄ |
| 1719 | Ethyl | 4-MeOC₆H₄ |
| 1720 | Cyclopentyl | 4-MeOC₆H₄ |
| 1721 | Cyclobutyl | 4-MeOC₆H₄ |
| 1722 | Benzyl | 4-MeOC₆H₄ |
| 1723 | n-propyl | 4-MeOC₆H₄ |
| 1724 | 4-ClC₆H₄CH₂ | 4-MeOC₆H₄ |
| 1725 | 3-MeOC₆H₄CH₂ | 4-MeOC₆H₄ |
| 1726 | 4-MeOC₆H₄CH₂ | 4-MeOC₆H₄ |
| 1727 | 3,4-diMeOC₆H₄CH₂ | 4-MeOC₆H₄ |
| 1728 | 2,5-diMeOC₆H₄CH₂ | 4-MeOC₆H₄ |
| 1729 | Methyl | 2-MeOC₆H₄ |
| 1730 | Methyl | 3,4-diMeOC₆H₄ |
| 1731 | 3,4-(OCH₂O)C₆H₄CH₂ | 4-MeOC₆H₄ |
| 1732 | 3-thiophenylCH₂ | 4-MeOC₆H₄ |
| 1733 | 2-MeOC₆H₄CH₂ | 4-MeOC₆H₄ |
| 1734 | 3,4-diClOC₆H₄CH₂ | 4-MeOC₆H₄ |
| 1735 | 2,4-diClOC₆H₄CH₂ | 4-MeOC₆H₄ |
| 1736 | 2-ClC₆H₄CH₂ | 4-MeOC₆H₄ |
| 1737 | H₂NCH₂ | 4-MeOC₆H₄ |
| 1738 | HOCH₂NHCH₂CH₂ | 4-MeOC₆H₄ |
| 1739 | Me₂NCH₂ | 4-MeOC₆H₄ |
| 1740 | PiperazinylCH₂ | 4-MeOC₆H₄ |
| 1741 | 4-Me-piperazinylCH₂ | 4-MeOC₆H₄ |
| 1742 | 4-HOCH₂CH₂-piperazinylCH₂ | 4-MeOC₆H₄ |
| 1743 | PiperidinylCH₂ | 4-MeOC₆H₄ |
| 1744 | 4-NH₂CH₂-piperidinylCH₂ | 4-MeOC₆H₄ |
| 1745 | CH₃CH₂NHCH₂ | 4-MeOC₆H₄ |
| 1746 | ThiomorpholinylCH₂ | 4-MeOC₆H₄ |
| 1747 | MorpholinylCH₂ | 4-MeOC₆H₄ |
| 1748 | PyyrolidinylCH₂ | 4-MeOC₆H₄ |
| 1749 | 4-pyridylCH₂NHCH₂ | 4-MeOC₆H₄ |
| 1750 | 4-CH₃CONHC₆H₄CH₂ | 4-MeOC₆H₄ |
| 1751 | 4-CH₃OCONHC₆H₄CH₂ | 4-MeOC₆H₄ |
| 1752 | 4-NH₂CH₂CONHC₆H₄CH₂ | 4-MeOC₆H₄ |
| 1753 | 4-Me₂NCH₂CONHC₆H₄CH₂ | 4-MeOC₆H₄ |
| 1754 | 4-N₃C₆H₄CH₂ | 4-MeOC₆H₄ |
| 1755 | 4-NH₂C₆H₄CH₂ | 4-MeOC₆H₄ |
| 1756 | C₆H₅NH | 4-MeOC₆H₄ |
| 1757 | CH₃CH₂CH₂NH | 4-MeOC₆H₄ |
| 1758 | 4-NH₂C₆H₄CH₂NH | 4-MeOC₆H₄ |
| 1759 | 4-pyridyCH₂NH | 4-MeOC₆H₄ |
| 1760 | Methyl | 4-HOC₆H₄ |
| 1761 | H | 4-MeOC₆H₄ |
| 1762 | Methyl | 3-pyridyl |
| 1763 | Methyl | 4-pyridyl |
| 1764 | H | 4-pyridyl |
| 1765 | Methyl | C₆H₅ |
| 1766 | Methyl | 4-MeSC₆H₄ |
| 1767 | Methyl | 4-MeSO₂C₆H₄ |
| 1768 | Methyl | 4-Me₂NC₆H₄ |
| 1769 | MorpholinylCH₂ | 4-Me₂NC₆H₄ |
| 1770 | Me₂NCH₂ | 4-Me₂NC₆H₄ |
| 1771 | Me₂NCH₂ | 4-(piperdinyl)C₆H₄ |
| 1772 | Me₂NCH₂ | 4-(morpholinyl)C₆H₄ |
| 1773 | Me₂NCH₂ | 4-CH₃CH₂OC₆H₄ |
| 1774 | Me₂NCH₂ | 4-CH₃CH₂CH₂CH₂C₆H₄ |
| 1775 | Me₂NCH₂ | 4-CH₃CH₂C₆H₄ |
| 1776 | Me₂NCH₂ | 4-CH₃CH₂CH₂C₆H₄ |

What is claimed is:

1. A compound according to the formula:

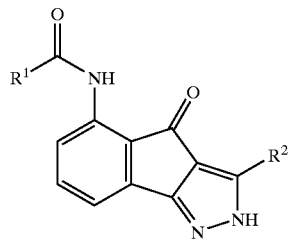

or a stereoisomer or pharmaceutically acceptable salt form thereof, wherein:

X is selected from the group consisting of O and S;

R¹ is NHR₄;

R⁴ is NR³R³ᵃ;

R³ᵃ is H or C₁₋₄ alkyl;

R³ is COR⁵;

R⁵ is phenyl; and

R² is phenyl substituted with C₁₋₄ alkoxy.

2. A compound according to claim 1, wherein the compound is 3-(4-methoxyphenyl)-5-(2-benzoylhydrazinecarboxamido)indeno[1,2-c]pyrazol-4-one.

3. A pharmaceutical composition comprising a pharmaceutically acceptable carrier and a therapeutically effective amount of a compound of the following formula:

or a stereoisomer or pharmaceutically acceptable salt form thereof, wherein:

X is selected from the group consisting of O and S;

R¹ is NHR₄;

R⁴ is NR³R³ᵃ;

R³ᵃ is H or C₁₋₄ alkyl;

R³ is COR⁵;

R⁵ is phenyl; and

R² is phenyl substituted with C₁₋₄ alkoxy.

4. A method of treating cancer and proliferative diseases comprising: administering to a host in need of such treatment a therapeutically effective amount of a compound of the following formula:

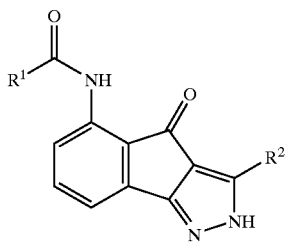

or a pharmaceutically acceptable salt or prodrug form thereof, wherein:

X is selected from the group consisting of O and S;

$R^1$ is $NHR_4$;

$R^4$ is $NR^3R^{3a}$;

$R^{3a}$ is H or $C_{1-4}$ alkyl;

$R^3$ is $COR^5$;

$R^5$ is phenyl; and $R^2$ is phenyl substituted with $C_{1-4}$ alkoxy.

* * * * *